(12) United States Patent
Steinbrecher et al.

(10) Patent No.: US 7,700,572 B2
(45) Date of Patent: Apr. 20, 2010

(54) SMAD7 INHIBITORS FOR THE TREATMENT OF CNS DISEASES

(75) Inventors: Andreas Steinbrecher, Regensburg (DE); Gerhard Giegerich, Koefering (DE); Ingo Kleiter, Regensburg (DE); Markus Horn, Sinzing (DE); Rainer Apfel, Sinzing (DE); Roland Kreutzer, Weidenberg (DE); Stefan Limmer, Kulmbach (DE); Hans-Peter Vornlocher, Bayreuth (DE)

(73) Assignee: Giuliani International, Ltd., Dublin (IE)

( * ) Notice: Subject to any disclaimer, the term of this patent is extended or adjusted under 35 U.S.C. 154(b) by 583 days.

(21) Appl. No.: 10/494,333

(22) PCT Filed: Oct. 31, 2002

(86) PCT No.: PCT/EP02/12221

§ 371 (c)(1),
(2), (4) Date: Apr. 30, 2004

(87) PCT Pub. No.: WO03/037368

PCT Pub. Date: May 8, 2003

(65) Prior Publication Data

US 2005/0119203 A1 Jun. 2, 2005

(30) Foreign Application Priority Data

Nov. 2, 2001 (EP) .................................. 01126140

(51) Int. Cl.
*A61K 48/00* (2006.01)
*C07H 21/04* (2006.01)
*C07H 21/02* (2006.01)

(52) U.S. Cl. ..................... 514/44; 536/23.1; 536/24.31; 536/24.33; 536/24.5

(58) Field of Classification Search ........................ None
See application file for complete search history.

(56) References Cited

U.S. PATENT DOCUMENTS

2003/0049662 A1* 3/2003 Monia et al. .................... 435/6

FOREIGN PATENT DOCUMENTS

| WO | WO 97/30065 | * | 8/1997 | ................... | 514/44 |
|---|---|---|---|---|---|
| WO | WO 98/53068 A | | 11/1998 | | |
| WO | WO 01/53313 A | | 7/2001 | | |

OTHER PUBLICATIONS

Scherer et al., Approaches for the sequence-specific knockdown of mRNA, 2003, Nat. Biotechnol., 21(12), pp. 1457-1465.*
Mahato et al., Modulation of gene expression by antisense and antigene oligodeoxynucleotides and small interfering RNA, Jan. 2005, Expert Opinion on Drug Delivery, vol. 2, No. 1, pp. 3-28.*
Nguyen et al., RNAi therapeutics: An update on delivery, 2008, Current Opinion in Molecular Therapeutics, 10(2), pp. 158-167.*
Zhang et al., Targeted Gene SIlencing by Small Interfering RNA-Based Knock-Down Technology, 2004, Current Pharmaceutical Biotechnology, vol. 5, p. 1-7.*
Rayburn et al., Antisense, RNAi, and gene silencing strategies for therapy: Mission possible or impossible?, 2008, Drug Discovery Today, vol. 13, Nos. 11/12, pp. 513-520.*
Zhang et al., microRNAs: a new emerging class of players for disease diagnostics and gene therapy, 2008, J. Cell. Mol. Med., vol. 12, No. 1, pp. 3-21.*
Souchelnytskyi et al., Physical and Functional Interaction of Murine and Xenopus Smad7 with Bone Morphogenetic Protein Receptors and Transforming Growth Factor-β Receptors, 1998, The Journal of Biological Chemistry, vol. 273, No. 39, pp. 25364-25370.*
Mokhtarian et al., Defective Production of Anti-Inflammatory Cytokine, TFG-β by T Cell Lines of Patients with Active Multiple Sclerosis, 1994, Journal of Immunology, 152(12), pp. 6003-6010.*
Monteleone et al., "blocking Smad7 restores TGF-beta1 signaling in chronic inflammatory bowel disease", Journal of Clinical Investigation, vol. 108, No. 4, Aug. 2001, pp. 601-609, XP001152527, ISSN: 0021-9739.
Kiefer et al., "Sequential expression of transforming growth factor-beta1 by T-cells, macrophages, and microglia in rat spinal cord during autoimmune inflammation", Journal of Neuropathology & Experimental Neurology, vol. 57, No. 5, May 1998, pp. 385-395, XP009012626, ISSN: 0022-3069.
Steinbrecher et al., "Targeting dipeptidyl peptidase IV (CD26) suppresses autoimmune encephalomyelitis and up-regulates TGF-beta 1 secretion in vivo", Journal of Immunology, vol. 166, No. 3, Feb. 1, 2001, pp. 2041-2048, XP002241939, ISSN: 0022-1767.
Calabresi et al., "Phase 1 trial of transforming growth factor beta 2 in chronic progressive MS", Neurology, vol. 51, No. 1, Jul. 1998, pp. 289-292, XP009011224, ISSN: 0028-3878.
Landstrom et al., "Smad7 mediates apoptosis induced by transforming growth factor beta in prostatic carcinoma cells", Current Biology, vol. 10, No. 9, May 4, 2000, pp. 535-538, XP002252297, ISSN: 0960-9822.
Database EMBL 'Online!, Jun. 1, 2001, "*Homo sapiens* MAD-related gene SMAD7 (SMAD7) mRNA, complete cds", Database accession No. AF010193, XP002252298.
Prud'Homme et al., "The Inhibitory Effects of Transforming Growth Factor-Beta-1 (TGF-β1) in Autoimmue Diseases," *Journal of Autoimmunity* (2000) 14, pp. 23-42.
Soilu-Hänninen et al., "Treatment of Experimental Autoimmune Encephalomylitis With Antisense Oligonucleotides Against the Low Affinity Neurotrophin Receptor," *Journal of Neuroscience Research* 59:712-721 (2000).

(Continued)

Primary Examiner—Amy Bowman
(74) *Attorney, Agent, or Firm*—Goodwin Procter LLP

(57) ABSTRACT

The present invention relates to the use of a specific inhibitor of Smad7 expression or function for the preparation of a pharmaceutical composition for the prevention, amelioration or treatment of a disease of the central nervous system and/or diseases related and/or caused by said disease of the central nervous system. Furthermore, methods for preventing, ameliorating and/or treating such diseases are disclosed.

4 Claims, 39 Drawing Sheets

OTHER PUBLICATIONS

Massagué, "How Cells Read TGF-β Signals," *Nature Reviews—Molecular Cell Biology*, Dec. 2000, pp. 169-178, vol. 1.

Hohlfeld et al., "The Ups and Downs of Multiple Sclerosis Therapeutics," *Annals of Neurology*, Mar. 2001, pp. 281-284, vol. 49, No. 3, Wiley-Liss, Inc.

Wiendl et al., "Multiple Sklerose, Aktuelle Übersicht zu fehlgeschlagenen und abgebrochenen Therapiestudien," *Nervenarzt*, Aug. 2000, pp. 597-610, vol. 71, Springer-Verlag.

Miyazono et al., "Divergence and Convergence of TGF-β/BMP Signaling," *Journal of Cellular Physiology*, 2001, pp. 265-276, vol. 187, Wiley-Liss, Inc.

Kiefer et al., "Sequential Expression of Transforming Growth Factor-β1 by T-cells, Macrophages, and Microglia in Rat Spinal Cord during Autoimmune Inflammation," *Journal of Neuropathology and Experimental Neurology*, May 1998, pp. 385-395, vol. 57, American Association of Neuropathologists.

\* cited by examiner

Figure 1:
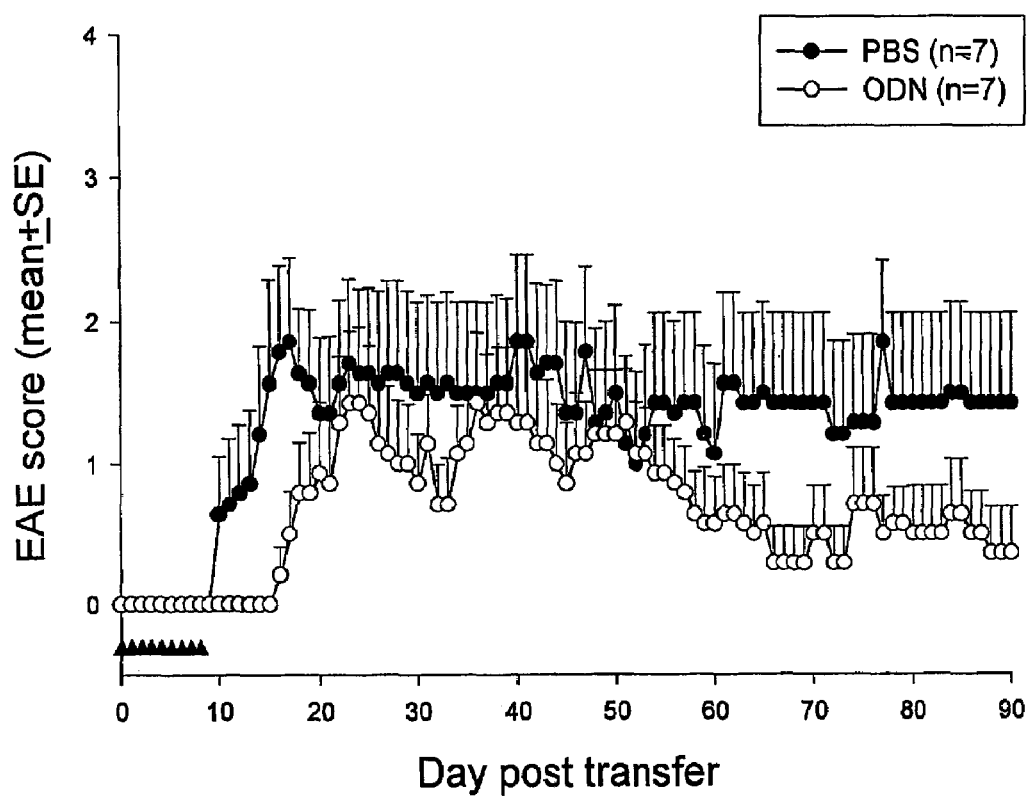

Fig. 1: Smad7-as-ODN-treatment delays onset and alleviates clinical severity in at-EAE Fig. 2: Long-term effect of Smad7-as-ODN treatment on clinical disease Fig.3: Graded therapeutic effect of different Smad7-as-ODN sequences on EAE Fig. 4: Therapeutic effect of Smad7as-ODN-treatment on ongoing CNS disease Fig. 5: Autoreactive lymph node cells do not induce EAE after Smad7-as-ODN-treatment in vitro Fig. 6: Suppressive effect of Smad7-as2-ODN on the proliferation of PLP-activated LNC in vitro Fig. 7: Smad7-as-ODN diminishes the proliferation of activated LNC in vitro Fig. 8: Absence of toxicity of Smad7-as/2-ODN against activated LNC Fig. 9: Smad7-as2-ODN are not toxic against activated LNC Fig. 10: Inhibition of priming of autoreactive LNC by in vivo Smad7-as-ODN-treatment Reduced inflammation in Smad7-as-treated mice No organ toxicity of smad7 as2-therapy

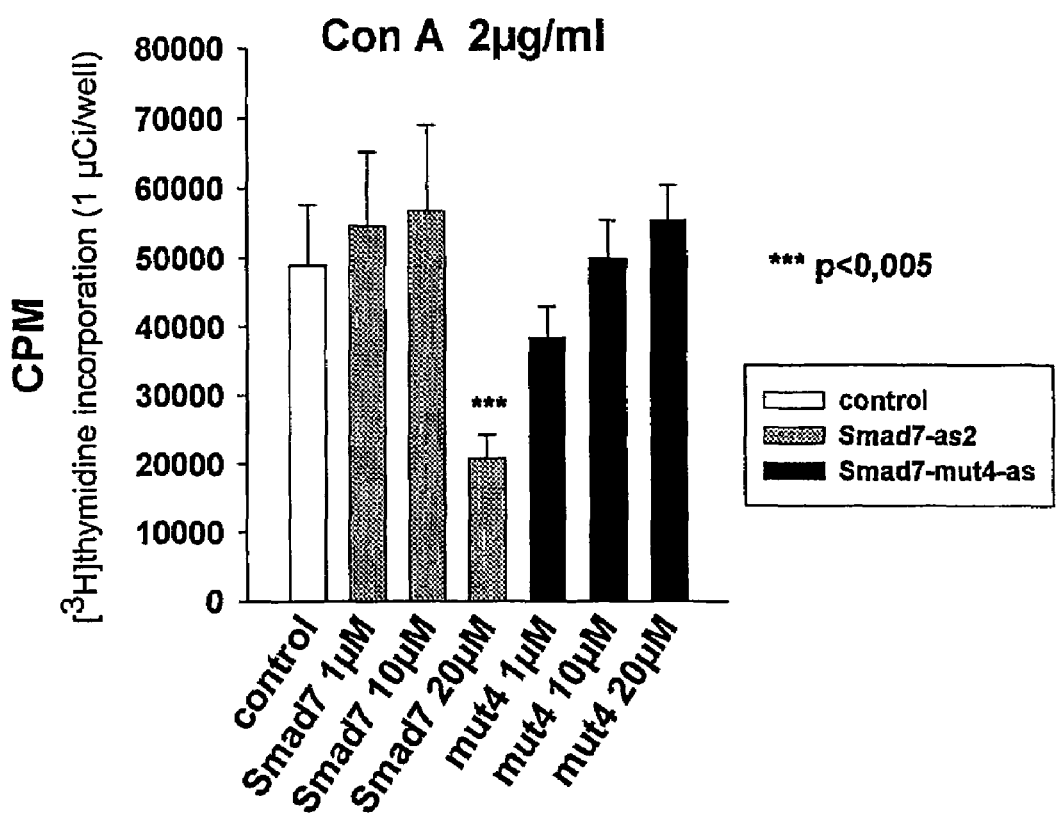
Fig. 14: Smad7-as2-ODN diminishes the proliferation of mitogenically activated spleen cells

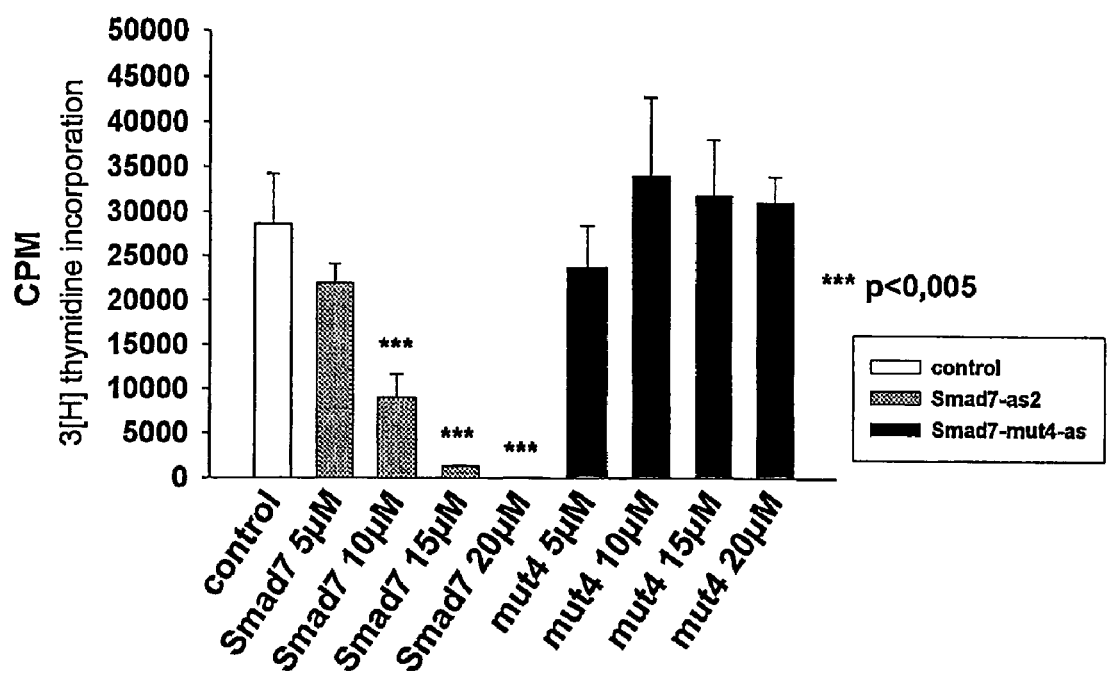
Fig. 15a: Ficoll enriched spleen cells, anti-CD3-stimulation: suppression by Smad7-as2-ODN

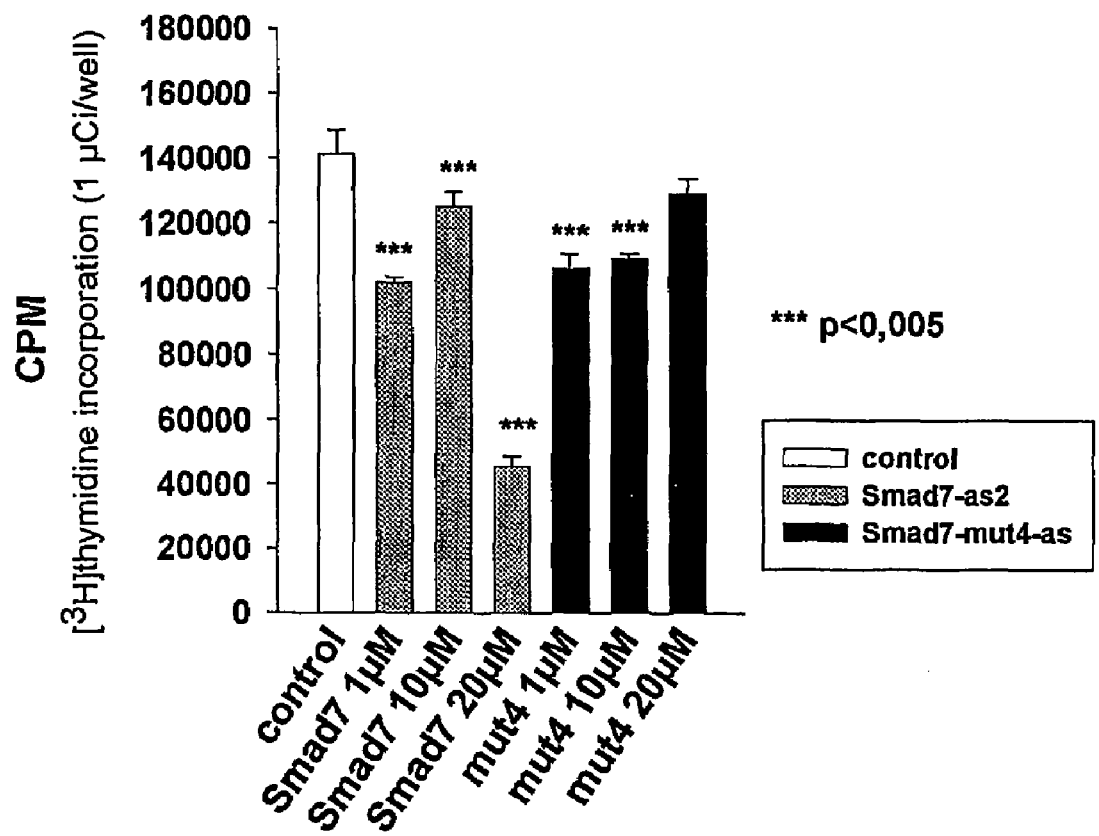
Fig. 15b: CD4+ T cells: anti-CD3-stimulation: suppression by Smad7-as2-ODN

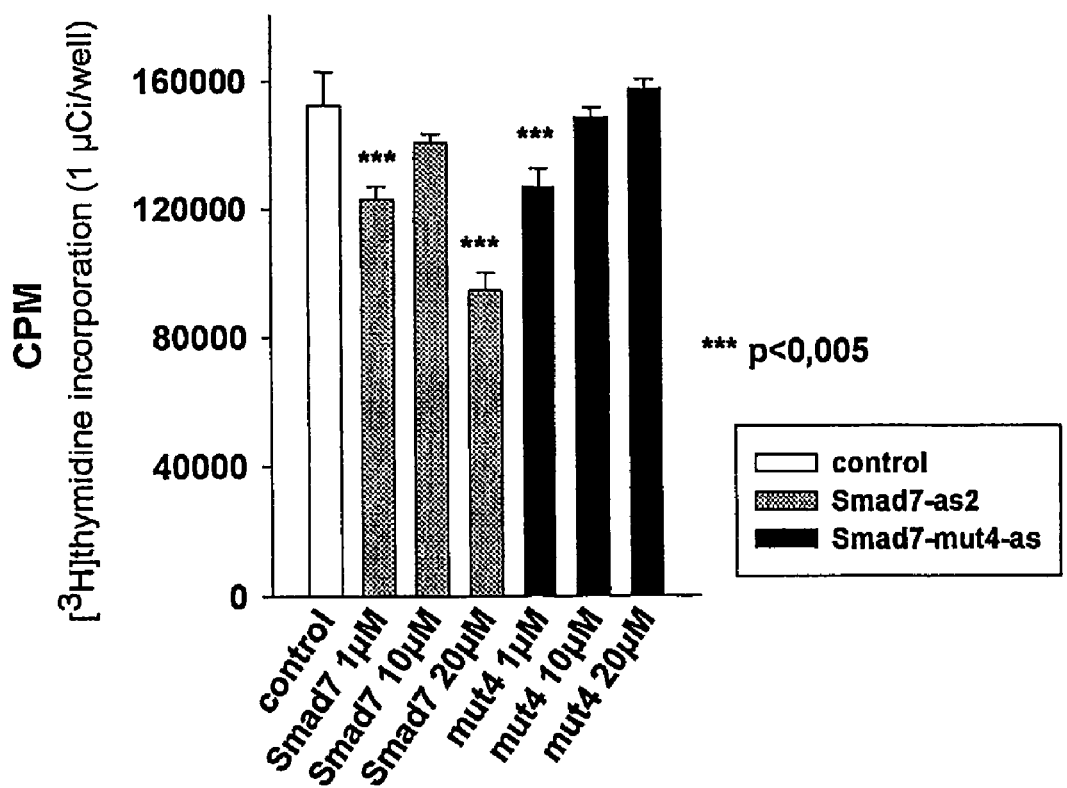
Fig. 15c: CD8+ T cells: anti-CD3-stimulation: suppression by Smad7-as2-ODN

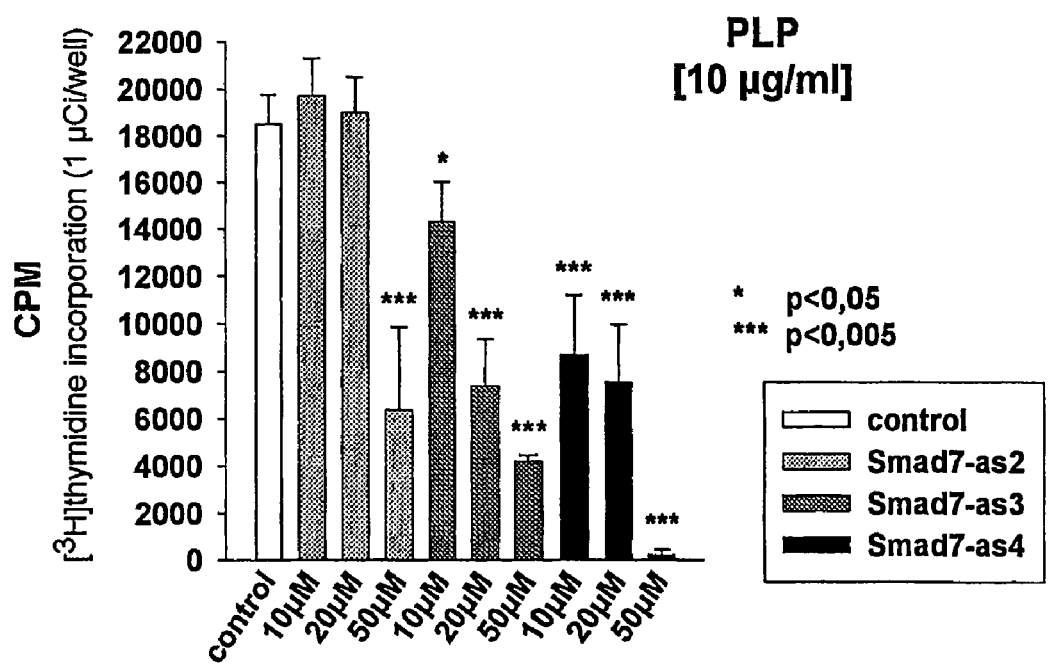
Fig. 16: Effects of diverse Smad7 antisense-ODN on T cell proliferation in vitro

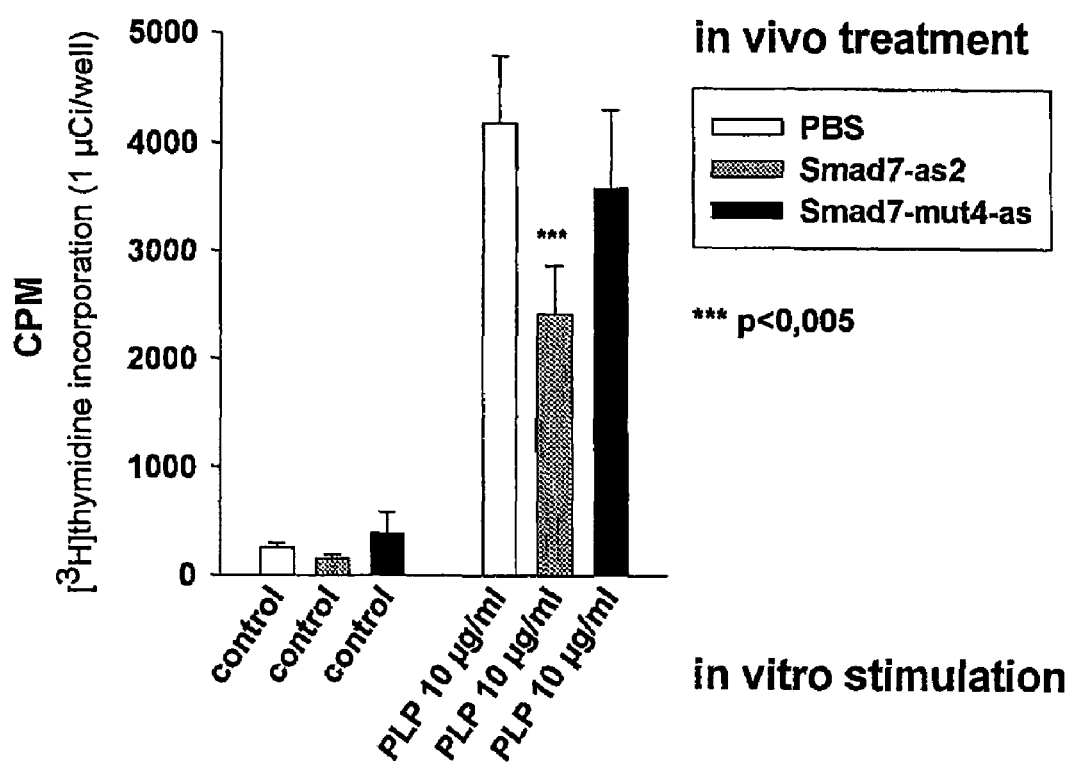
Fig. 17: Smad7-as2-ODN-treatment in vivo inhibits antigenic priming responses.

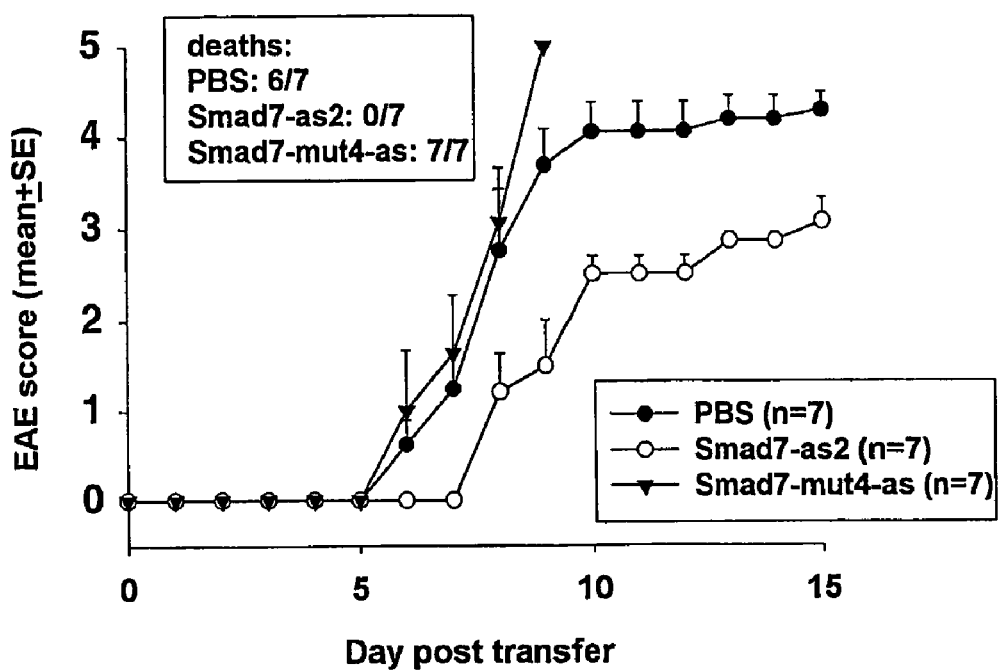
Fig. 18a: In vivo-treatment with Smad7-as2-ODN reduces encephalitogenicy of antigen-restimulated LNC

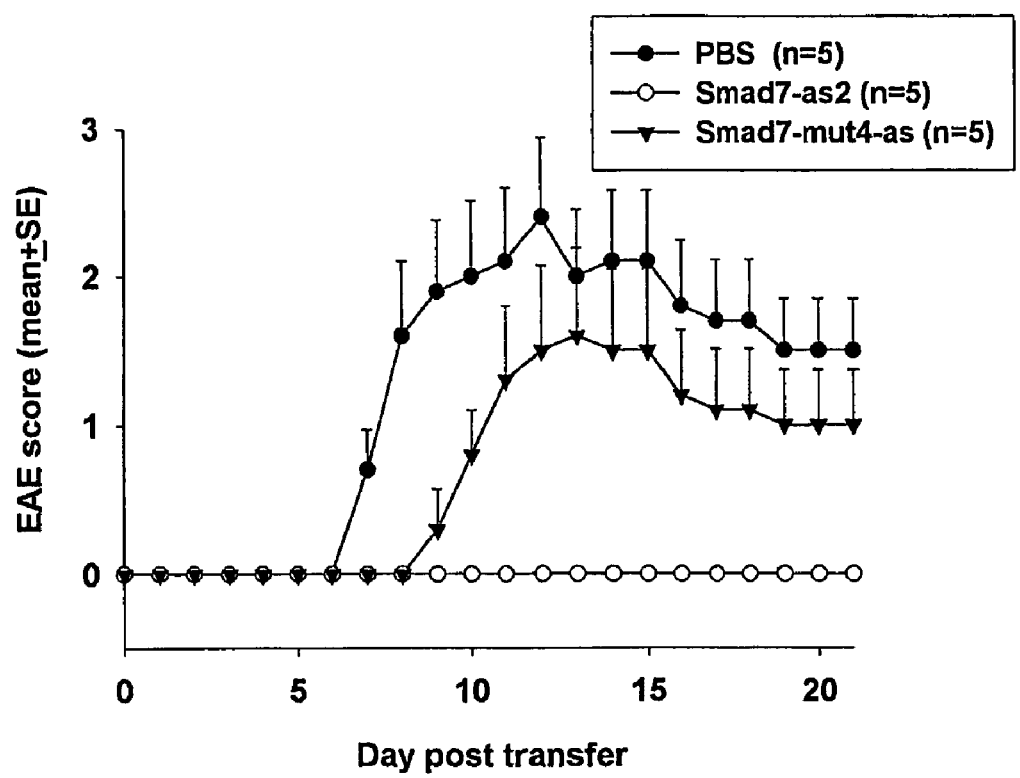
Fig. 18b: In vivo-treatment with Smad7-as2-ODN reduces encephalitogenicy of antigen-restimulated LNC

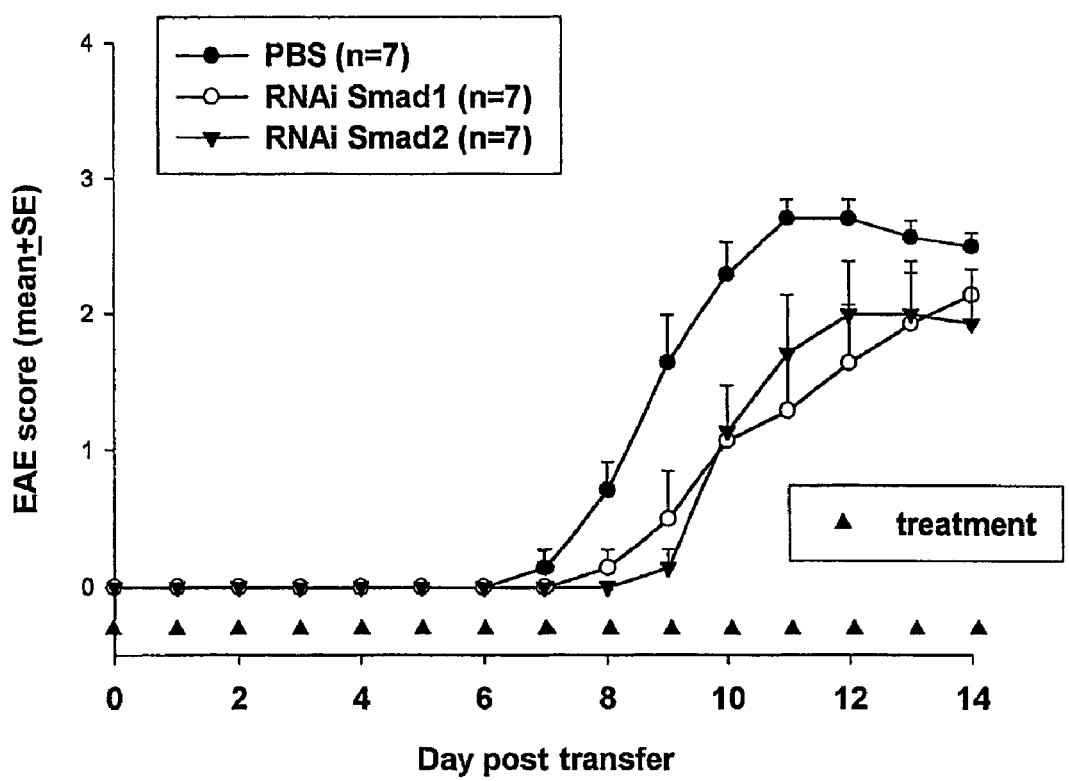
Fig. 19: Preventive treatment with Smad7-specific short interfering RNAs (RNAis)

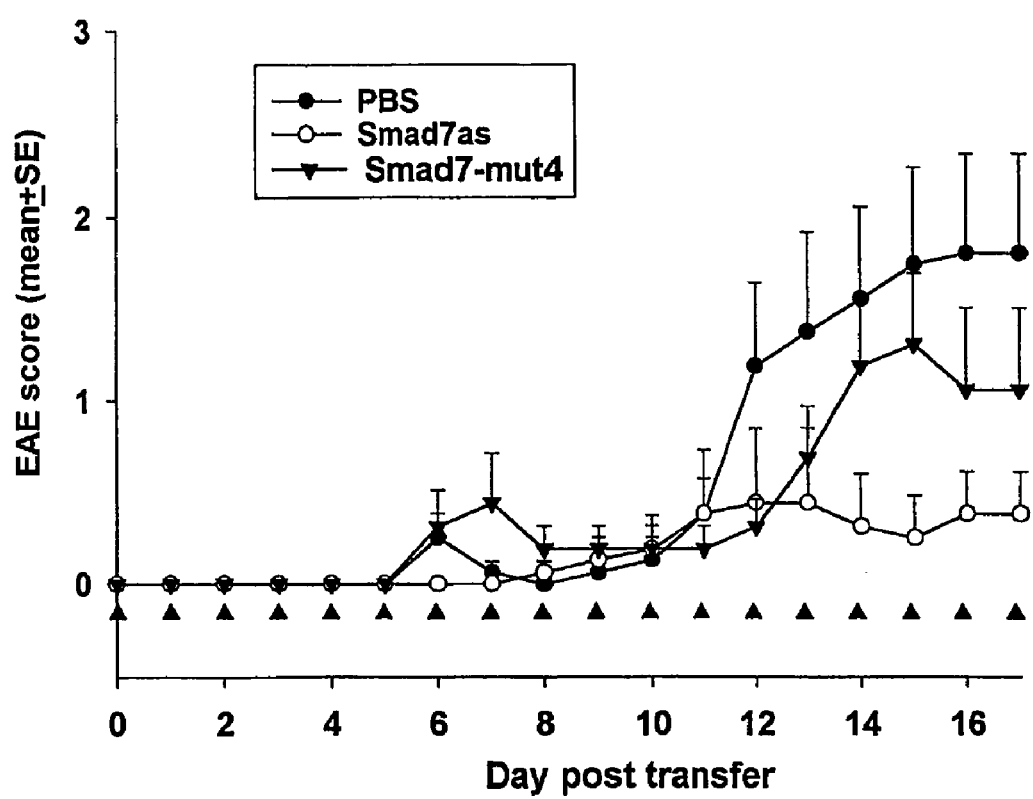
Fig. 20: Preventive Smad7-antisense treatment in MOG-induced EAE in the rat

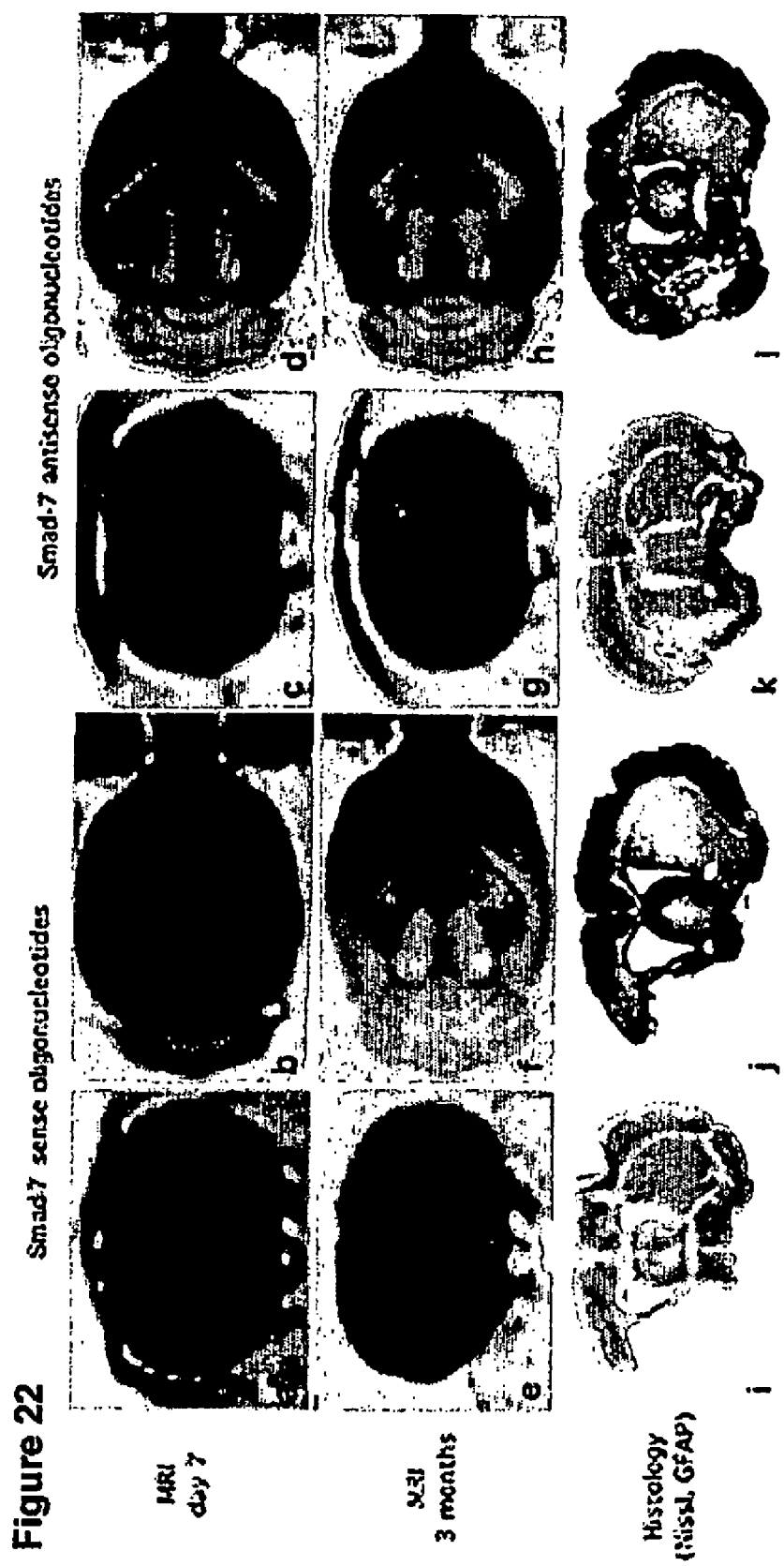

Fig. 23a

SEQ ID NO:1, human Smad7 mRNA

```
   1  ggcacgagcg gagagccgcg cagggcgcgg gccgcgcggg gtgggcagc cggagcgcag
  61  gccccgatc cccggcgggc gccccccggc gccccggcct gcccggcc ccggagact
 121  ggcgcatgcc acggagcgcc cctcggccg ccgcgctcc tgcccggcc cctgctgctg
 181  ctgctgtcgc ctgcgcctgc tgcccaact cggcgcccga cttcttcatg gtgtgcggag
 241  gtcatgttcg ctccttagca ggcaaacgac tttctcctc gcctcctcgc cccgcatgtt
 301  caggaccaaa cgatctgcgc tcgtccggcg tctctggagg agccgtgcgc ccggcggcga
 361  ggacgaggag gagggcgcag gggaggtgg aggaggagc cggccccg gagctgcggg gagaagggc
 421  gacggacagc cgagcgcatg ggcgcgaggg cggcgcccg caccatccc gagctgcctg gatgctgcct
 481  gggcaaggcg gtgcgagttg ccaaagtca ccaaagtca ccaccgccag ccgcgggcgc
 541  cggcgcgggc ggggcgccg aggcggatct gaaggcgctc acgcactcgg tgctcaagaa
 601  actgaaggag cggcagctgg agctgctgct ccaggccgtg gagtccgcg gcggacgcg
 661  caccgcgtgc ctcctgctgc ccgcgcagc gactgcagg ctggccccgg gggcccccgc
 721  cggcgcgcag cctgcgcagc cgccctcgtc ctactcgtc cccctcctgc tgtgcaaagt
 781  gttcaggtgg ccggatctca ggcattccte ggaagtcaag aggctgtgtt gctgtgaatc
 841  ttacgggaag atcaacccg agctgtgtg ctgcaaccce catcaccta gccgactctg
 901  cgaactagag tctccccccc cagatacccg cgctgaaaca atgggattttc tcaaaccaac
 961  tgcagactgt ccagatgctg tgccttcctc cgctgaaaca tctgagcct ggggatcggt attatctggc
1021  ccctggggg ctttcagatt cccaacttct tctgagcct ggggatcggt cacactggtg
1081  cgtggtggca tactgggagg agaagacgag agtggggagg ctctactgtg tccaggagcc
1141  ctctctggat atcttctatg atctacctca gggaatggc tttgccttgc gacagctcaa
```

Fig. 23b

```
1201 ttcggacaac aagagtcagc tggtgcagaa ggtgcggagc aaaatcggct gcggcatcca
1261 gctgacgcgg gaggtggatg gtgtgtgggt gtacaaccgc agcagttacc ccatcttcat
1321 caagtccgcc acactggaca acccggactc caggacgctg ttggtacaca aggtgttccc
1381 cggtttctcc atcaaggctt tcgactacga gaaggcgtac agcctgcagc ggcccaatga
1441 ccacgagttt atgcagcagc cgtggacggg ctttaccgtg cagatcagct ttgtgaaggg
1501 ctggggtcag tgctacaccc gccagttcat cagcagctgc ccgtgctggc tagagtcat
1561 cttcaacagc cggtagccgc gtgcggaggg gacagagcgt gagctgagca ggccacactt
1621 caaactactt tgctgctaat atttcctcc tgagtgcttg ctttcatgc aaactctttg
1681 gtcgttttt tttgttttgt tggttgttt tcttcttctc gtcctcgttt gtgttctgtt
1741 ttgtttcgct ctttgagaaa tagcttatga aaagaattgt tgggggttt tttgaagaa
1801 ggggcaggta tgatcggcag gacaccctga taggaagagg ggaagcagaa atccaagcac
1861 caccaaacac agtgtatgaa gggggcggt catcatttca cttgtcagga gtgtgtgtga
1921 gtgtgagtgt gcggctgtgt gtgcagcgcg gtgcaggagc ggcagatggg gagacaacgt
1981 gctctttgtt ttgtctctct tatgatgtc cccagcagag aggtttgcag tcccaagcgg
2041 tgtctctcct gccccttga cacgctcagt ggggcagagg cagtacctgg gcaagctggc
2101 ggctggggtc ccagcagctg ccaggagcac ggctctgtcc ccagcctgtg aaagcccctg
2161 cccctcctct ccctcatcaa ggacacgggc ctgtccacag gcttctgagc agcgagcctg
2221 ctagtggccg aaccagaacc aattattttc atccttgtct tattccctc ctgccagccc
2281 ctgccattgt agcgtctttc tttttggcc atctgctcct ggatctccct gagatgggct
2341 tcccaagggc tgcggggca gcccccctcac agtattgctc acccagtgcc ctctccctc
```

Fig. 23c

```
2401 agcctctccc ctgcctgccc tggtgacatc aggtttttcc cggacttaga aaaccagctc
2461 agcactgcct gctcccatcc tgtgtgttaa gctctgctat taggccagca agcggggatg
2521 tccctgggag ggacatgctt agcagtcccc ttccctccaa gaaggatttg gtccgtcata
2581 acccaaggta ccatcctagg ctgacaccta actctctttt catttcttct acaactcata
2641 cactcgtatg atacttcgac actgttctta gctcaatgag catgtttaga ctttaacata
2701 agctattttt ctaactacaa aggtttaaat gaacaagaga agcattctca ttgaaaattt
2761 agcattgtag tgctttgaga gagaaaggac tcctgaaaaa aaacctgaga tttattaaag
2821 aaaaaaatgt attttatgtt atatataaat atattattac ttgtaaatat aaagacgttt
2881 tataagcatc attatttatg tattgtgcaa tgtgtataaa caagaaaaat aaagaaaaga
2941 tgcactttgc tttaatataa atgcaaataa caaatgccaa attaaaaaag ataaacacaa
3001 gattggtgtt tttcctatg ggtgttatca cctagctgaa tgttttctta aaggagttta
3061 tgttccatta aacgattttt aaaatgtaca cttgaaaaaa aaaaaaaaaa a
```

Target sequences of human Smad7-Antisense Oligonucleotides SEQ ID No: 16-29 are underlined, one partially overlapping sequence, corresponding to SEQ ID NO: 21, is shown in italics.

Fig. 24

SEQ ID NO:2, human Smad7 AminoAcid Sequence

CDS        296..1576
           /gene="SMAD7"
           /codon_start=1
           /product="MAD-related gene SMAD7"

/translation="MFRTKRSALVRRLWRSRAPGGEDEEEGAGGGGGGELRGEGATD
           SRAHGAGGGGPGRAGCCLGKAVRGAKGHHHPHPPAAGAGAAGGAEADLKALTHSVLKK
           LKERQLELLLQAVESRGGTRTACLLLPGRLDCRLGPGAPAGAQPAQPPSSYSLPLLLC
           KVFRWPDLRHSSEVKRLCCCESYGKINPELVCCNPHHLSRLCELESPPPPYSRYPMDF
           LKPTADCPDAVPSSAETGGTNYLAPGGLSDSQLLLEPGDRSHWCVVAYWEEKTRVGRL
           YCVQEPSLDIFYDLPQGNGFCLGQLNSDNKSQLVQKVRSKIGCGIQLTREVDGVWVYN
           RSSYPIFIKSATLDNPDSRTLLVHKVFPGFSIKAFDYEKAYSLQRPNDHEFMQQPWTG
           FTVQISFVKGWGQCYTRQFISSCPCWLEVIFNSR"

Fig. 25a

SEQ ID NO:3, Mouse Smad7 mRNA

```
   1  cgagtgcggc gcggcgagcc cccagcgcgcg gcagaaggac tcgagcgcca ggagagggcg
  61  gacggggac gaggagctc cggggcgcga cgaagagagt ctccgagaa gaggctgcga
 121  gaggacaccc gggcctcctg ccgccactgt cgggtcgggg ccagcagctc atgagagcag
 181  ccccgcgcgc caccccgcgc caggagaagg agcaccggag agcccgcgc gccccacac tagcctgtgc
 241  cctcgggggc gagagcttgc gaccccgcgg agcccgcgc cgcgccgcgc tccccgcgc
 301  tgacagcccc ccggggcgca gccgcgcgcg cagcatcttc tgtccctgct tccccagcgc
 361  ggaggaagtc cccgccgagg acctgagcgc ccggaaacgc aggagaaag accagagact
 421  ctaaaacacc cagatacgca agattgaagc agcctagcca gaccttttctg tggattaaaa
 481  gaaatacgat tttttttttt tttttttggc agaagaaaag gaaagctgggt
 541  tcagcaagga aaaaaagggg gatgtaactc gtggatacgg ttttttcccc ccaccccttcc
 601  aacatcttgt tttattttgt aaacattttc tcttttaaac ccggctcca tccggtgcc
 661  tccagacctc cgaggtgcga ggaggtggtg tgtttttttca ttgggggctt tgcatattttt
 721  ggttttgggg gttttgagag accctccaga catctcacga ggggtgaagt ctactcggtc
 781  ccctcccgca agtcttcgcg tgcacagaat tcgaggagat cggttacta aggatataga
 841  agaaaaaaaa taaatcgtgc ctgccttttt ttttaattg cctgcttctc cccaccccca
 901  aattaagttg cttagcaagg gggaaagagg cttttttcctc cctttagtag ctcagcctaa
 961  cgtcttttcgt tttttttttt tttttgcccc tttttcgccc gaggatcttc catgtaggaa
1021  gccgaggctg gcgagcccga cactcgggag ccactgtagg gggccttttt ttggggagg
1081  cgtctaccgg ggttgcctcg gccgcccca gggaagcggc ggccgcgttc ctccagggca
1141  cgccggggcc gcaagcgc gcagggcgcg ggccgcgcg gtgggcag ccgaagcgca
```

Fig. 25b

```
1201  gcccccgat  ccccggcagg  cgccctggg  ccccgcgcg  cgccccggcc  tctgggagac
1261  tggcgcatgc  cacggagcgc  ccctcgggcc  gccgccgctt  ctgcccgggc  ccctgctgtt
1321  gctgctgtcg  cctgcgcctg  ctgcccaac  tcggcgcccg  acttcttcat  ggtgtgcgga
1381  ggtcatgttc  gctccttagc  cggcaaacga  cttttctcct  cgcctcctcg  cccgcatgt
1441  tcaggaccaa  acgatctgcg  ctcgtccggc  gtctctggag  gagccgtgcg  ccggcggcg
1501  aggacgagga  ggaggcgtg  ggggtggcg  gcggaggagg  cgagctgcgg  ggagaagggg
1561  cgacggacgg  ccgggcttat  gggcggttg  gcgcaggct  gggcaggget  ggctgctgcc
1621  tgggcaaggc  agtccgaggt  gccaaaggtc  accaccatcc  ccatccccca  acctcgggtg
1681  ccggggcggc  cggggggcgc  gaggcggatc  tgaaggcgct  cacgcactcg  gtgctcaaga
1741  aactcaagga  gcggcagctg  gagctgctgc  ttcaggccgt  ggactcccgc  ggcggtacgc
1801  gcaccgcgtg  cctcctgctg  cccgcccgcc  tggactgcag  gctgggcccg  gggcgcccg
1861  ccagcgcgca  gcccgcgcag  cgccctctgt  cctactcgct  cccctcctg  ctgtgcaaag
1921  tgttcaggtg  gccgatctc  aggcattcct  cggaagtcaa  gaggctgtgt  tgctgtgaat
1981  cttacggaa  gatcaaccc  gagctgtgt  gctgcaaccc  ccatcacctt  agtcgactct
2041  gtgaactaga  gtctcccct  cctccttact  ccagataccc  aatgatttt  ctcaaaccaa
2101  ctgcaggctg  tccagatgct  gtaccttcct  ccggcgaaac  cggcgggaacg  aattatctgg
2161  ccctggggg  gctttcagat  tcccaacttc  ttctggagcc  tggggatcgg  tcacactggt
2221  gcgtggtggc  atactgggag  gagaagactc  gcgtgggag  gctctactgt  gtccaagagc
2281  cctccctga  tatcttctat  gatctaccct  agggaaatgg  cttttgcctc  ggacagctca
2341  attcggacaa  caagagtcag  ctggtacaga  aagtgcggag  caagatcggc  tgtggcatcc
```

Fig. 25c

```
2401 agctgacgcg ggaagtggat ggcgtgtggg tttacaaccg cagcagttac cccatcttca
2461 tcaagtccgc cacactggac aacccggact ccaggacgct gttggtgcac aaagtgttcc
2521 ctgtttctc catcaaggct tttgactatg agaaagccta cagcctgcag cggcccaatg
2581 accacgagtt catgcagcaa ccatgacgg gtttcaccgt gcagatcagc tttgtgaagg
2641 gctggggcca gtgctacacc cgccagttca tcagcagctg cccgtgctgg ctgaggtca
2701 tcttcaacag ccggtagtcg gtcgtgtggt ggggagaaga ggacaggcg gatcgtgagc
2761 cgagcaggcc acgttcaaa ctacttgctg ctaatctttc ccgagtgatt gctttcatg
2821 caaactcttt ggttgtgtt gttattgcca ttcattgttg gtttgttt gttctgttct
2881 ggtttgtttt tttttttttt ctcccccaag ggctgccggg acagcccag tcacagtatt
2941 gctacccag tacctctca ggcccttcca ccggtccca gcgtggtgg tttttcatc
3001 aggtttctc cagatgtgga aagtcagctc agcatcccat ccccccatcct gtgtgctgag
3061 ctctgtagac cagcgagggg catcaggag ggacctgcgc agtgccccc cttcctgctg
3121 agaagggtgt agcccgtca caacaaagt accatccctt ggctggctcc cagccttct
3181 ctcagctcat acgctcgctc gtatgatact ttgacactgt tcttagctca atgagcatgt
3241 ttagaattta acataagcta ttttctaac tacaaaggtt taaatgaaca agagaagcat
3301 tctcattgga aatttagcat tgtagtgctt tgagagagga aaggactcct taaaagaaaa
3361 aaaaagctga gatttattaa agaaaaatgt atttattgtt atatataaat atattattac
3421 ttgtaaatat aaagacgttt tataagcatc attattatg tattgtgcaa tgtgtataaa
3481 cgagaagaat aaagaaaaga tgcactttgc ttttaataa atgtaaataa catgccaaat
3541 taaaaaaaa aagataaaca caagattggt gttttttct atgggtgtta tcacctagct
3601 gaatgttttt ctaaaggagt ttatgttcca ttaaacaatt tttaaaatgt taaaaaaaa
3661 aaaaaaaaaa aaaaaaaaa a
```

Target sequences of mouse Smad7-Antisense Oligonucleotides SEQ ID No: 7-15 are underlined, one partially overlapping sequence, corresponding to SEQ ID NO: 11, is shown in italics.

Fig. 26

SEQ ID NO:4, mouse Smad7 Amino Acid sequence

CDS     1437..2717
        /gene="Madh7"
        /codon_start=1

/translation="MFRTKRSALVRRLWRSRAPGGEDEEEGVGGGGGGELRGEGATD
        GRAYGAGGGAGRAGCCLGKAVRGAKGHHHPHPPTSGAGAAGGAEADLKALTHSVLKK
        LKERQLELLLQAVESRGGTRTACLLLPGRLDCRLGPGAPASAQPAQPPSSYSLPLLLC
        KVFRWPDLRHSSEVKRLCCCESYGKINPELVCCNPHHLSRLCELESPPPYSRYPMDF
        LKPTAGCPDAVPSSAETGGTNYLAPGGLSDSQLLLEPGDRSHWCVVAYWEEKTRVGRL
        YCVQEPSLDIFYDLPQGNGFCLGQLNSDNKSQLVQKVRSKIGCGIQLTREVDGVWVYN
        RSSYPIFIKSATLDNPDSRTLLVHKVFPGFSIKAFDYEKAYSLQRPNDHEFMQQPWTG
        FTVQISFVKGWGQCYTRQFISSCPCWLEVIFNSR"

Fig. 27a

SEQ ID NO:5, Rat Smad7 mRNA

```
   1 tgagtgcggc gcggcgagcc cccagcggcg gcagaaggac tcgagcgcca ggagagggcg
  61 gacggggggac gaggagctc cggggcgcga cgaagagagt ctcggaggaa gaggctgcga
 121 gaggacaccc gggcctcctg cgccactgt cgggtcgggg ccagcagctt atgcgagcag
 181 cccccagcgac caccctcggc caggagaagg ggcaccggca gccccacgc tagctagcct
 241 gccgcctgtg ccctcggggg cgagagcttg cgacccgccg gagcccgccg ccgcgccgcc
 301 ctccccgcg ctgacagccc ccgggcgc agccgccgcc gcagcatctt ctgtccctgc
 361 ttccccagcg cggaggaagt cccgccgag gacctgggc cccgggagcg caggaggaaa
 421 gaccagagac tctaaaacac ccagatacgc aagattgaag cagcctaacc agaccttct
 481 gtggattaaa agaaatacga tttttttttt gacagaagaa aaggaaagaa agaccggcgg
 541 ggttcagcaa ggaaaaaaag gggatgtaac tcgtggatac ggttttttccc cccaccttc
 601 caacatcttg ttctactttg taaacatttt ctctttttaa acccccggctc catccggtgc
 661 cctccagacc tcgaggtgc gagaaggtgg tgtgttttt cactggggggc tttgcatatt
 721 tggttttggg gttttgaga gaccctccag acatctcacg aggggtgaag tctactcggc
 781 ccctccctc aagtcttcgc gtgcacagaa ttcgaggaga tccggttact aaggatatag
 841 aagaaaaaa taaatcgtgt gcctgccttt tttttttta attgcctgct tctcccacc
 901 cccaaattaa gttgcttagc aaggggaaa gaggcttttt cctcccttca gtagctcagc
 961 ctaacgtctt tcgttttttg ccctgagga tcttccatgt aggaagccga ggctgcgag
1021 cccgacactc gggagccact gtaggggggc cttttgggg agaggcgtcg accgggctg
1081 cctcggccgc ccccaggaa gcggcgccg cgttcctcag gggcacgccg gggcccgaga
1141 gcgcgcagg gcggggccg cgccgggtgg ggcagccgaa gcgcaggccc ccgatccccg
```

Fig. 27b

```
1201 gcgggcgccc ctgggccccc gcgcgcgccc cggcctccgg gagactggcg catgccacgg
1261 agcgcccctc gggccgccgc cgcttctgcc cgggcccctg ctgttgttgc tgtcgcctgc
1321 gcctgctgcc ccaactcggc gcccgacttc ttcatggtgt gcggaggtca tgttcgctcc
1381 ttagccggca aacgactttt ctcctcgcct cctcgccccg catgttcagg accaaacgat
1441 ctgcgctcgt ccggcgtctc tggaggagcc gtgcgcccgg cggcgaggac gaggaggagg
1501 gcgtggggg tggcggcggc ggaggcgacc tgcggggaga agggcgacg gacggccggg
1561 cttatggggc tggtggcggc ggtgcgggca gggctgctg ctgcctgggt aagcagtcc
1621 gaggtgccaa agtcaccac catcccatc cccatcctc gggtgccggg gcggccgggg
1681 gcgccgaggc ggatctgaag gcgctcacgc actcggtgct caagaaactc aaggagcggc
1741 agctgagct gctgcttcag gccgtggagt cccgcgggc gccgcccacc gcgtgcctcc
1801 tgctgccgg cgcctggac tgcaggctgg gcccggggc tcctgctgtg caaagtgttc gcgcagccg
1861 cgcagccgcc ctcgtcctac tcgtccccc tgtgttgctg acttagtcg agttgccgg
1921 atctcaggca ttcctcggaa gtcaagaggc acctcccatc actctgtgaa gggaagatca
1981 acccgagct ggtgtgctgc aaccccata atttctcaa accaactgca ctagagtctc
2041 cccctcctcc ttactccaga tacccgatgg gaacgaatta tctgccccct gactgtccag
2101 acgctgtacc ttcctccgat acttcttctg gagcctgggg atcggtcaca ctggtgcgtg gggggctttt
2161 cagattccca acttcttctg gagcctgggg atcggtcaca ctggtgcgtg gtgcatact
2221 gggaggagaa gactcgagtg gggaggctct actgtgtcca agagccctcc ctggatatct
2281 tctatgatct acctcagggg aatgcttt gcctcggaca gctcaattcg gacaacaaga
2341 gtcagctggt acagaaagtg tcggctgtgg catccagctg acaagggaag
2401 tggatggcgt gtgggtttac aaccgcagca gttacccat cttcatcaag tccgccacac
```

Fig. 27c

```
2461 tggacaaccc ggactccagg acgctgttgg tgcacaaagt gttccctggt ttctccatca
2521 aggcttttga ctatgaaaag gcctacagcc tgcagcggcc caatgaccac gagttcatgc
2581 agcagccatg gacgggcttc accgtgcaga ttagcttcgt gaagggctgg ggccagtgct
2641 acacccgcca gttcatcagc agttgcccgt gctggctgga ggtcatcttc aacagccggt
2701 agtctcccgg tgtggggaga agaggacagg acggaggggt gagccgagca ggccaccgtt
2761 caaactactt gctgctaatc tttcatgcaa aactctttcg gtcggttttg ttgtttgcca
2821 ttcattgttg gttctgtttt gttttgtttt cctttttttt tttcttcct tctttttttt
2881 cctccttcct tgtcactctt gtgtcctgtg tgtctcgttc tttgagaaaa tatgatgcgg
2941 atttttggtt gtgtgttttt ttttttcgtt tgttttgtttt ttgttgttgt ttgtgttttg
3001 agtggtggt gggtgcggtt ggcaggacac cccgatacaa aaacgggaag caagagtcag
3061 cactgccaag cgtggtgtgc gaaagtgggt accaccttcc cctttgatc agcatttcag
3121 ttgtcagtgt gtgtgtgtgta cgtgaatgac agatgggga atggcgtgct
3181 ttttttgtgt tctttatgga tgtcccagc tgagaggctt gcagttccaa gctgtgtgtc
3241 tctcactgtg tgtctctctc atgagccttt cggacatgct cggtgggca gaggcgtac
3301 ctggcagac tggcagcagg tgtccagca ggtgccgagc tctgtccgc tgaagctccc
3361 ccgccccgc cccctccccc acaggacacg ggcctatcca tttcatccct gtcctgtcac agaagccagc
3421 ctgctagaag gctgaaccag aaccaattgt tttcatccct gtcctgtcac ctcctgtcac
3481 ccgctgccat tgtcgaaggc tgtcttttt ggccatctgc tcctgatct ctcttgagat
3541 gggcttccca agggctgccg ggacagcccc agtcacagta ttgctacccc agtaccttct
3601 caggccttc caccggtccc agccgtggtt tttcatcag gttctcccca gatctgaaa
```

Fig. 27d

```
3661 gtcagctcag cacccatcc cccagcctgt gtgctgagct ctgtagacca gcgagggca
3721 tcagggaggg acctgctcag tgcccacca tcgtaggctg cccccttc ccgctgagaa gggtgtagcc
3781 ccgtcataac aaggtacca tcgtaggctg gctcccagcc cttctctcgg ctcatacact
3841 cgtatgatac tctgacactg ttcttggctc aatgagcatg ctcacacttt aatataagct
3901 attttctaa ctacaaaggt ttaaatgaac agagaggcg ttctcatcgg aaatttagca
3961 tcgtagtgct ttgagagagg aaaggactcc ttaaaagaga aaaaaaaag ctgagattta
4021 ttaaagaaaa aaatgtattt tatgtttatat ataaatatat tattacttgt aaatataaag
4081 acgttttata agcatcatta tttatgtatt gtgcaatgtg tataaacgag aataaagaaa
4141 agatgcactt tgcttttaata taaacgcaaa taacatgcca aattaaaaaa aaaaaagata
4201 aacacaagat tggtgtttt ttctatgggt gttatcacct agctgaatgt ttttctaaag
4261 gagtttatgt tccattaaac aattttttaaa atgtataaaa aaaaaaaaaa a
```

Target sequences of rat Smad7-Antisense Oligonucleotides SEQ ID No: 30-38 are underlined, one partially overlapping sequence, corresponding to SEQ ID NO: 34, is shown in italics.

Fig. 28

SEQ ID NO:6, rat Smad7 Amino Acid sequence

CDS     1422..2702
        /gene="Madh7"
        /codon_start=1

/translation="MFRTKRSALVRRLWRSRAPGGEDEEEGVGGGGGGDLRGEGATD
        GRAYGAGGGGAGRAGCCLGKAVRGAKGHHHPHPPSSGAGAAGGAEADLKALTHSVLKK
        LKERQLELLLQAVESRGGTRTACLLLPGRLDCRLGPGAPASAQPAQPPSSYSLPLLLC
        KVFRWPDLRHSSEVKRLCCCESYGKINPELVCCNPHHLSRLCELESPPPPYSRYPMDF
        LKPTADCPDAVPSSDETGGTNYLAPGGLSDSQLLEPGDRSHWCVVAYWEEKTRVGRL
        YCVQEPSLDIFYDLPQGNGFCLGQLNSDNKSQLVQKVRSKIGCGIQLTREVDGVWVYN
        RSSYPIFIKSATLDNPDSRTLLVHKVFPGFSIKAFDYEKAYSLQRPNDHEFMQQPWTG
        FTVQISFVKGWGQCYTRQFISSCPCWLEVIFNSR"

SMAD7 INHIBITORS FOR THE TREATMENT OF CNS DISEASES

The present invention relates to the use of a specific inhibitor of Smad7 expression or function for the preparation of a pharmaceutical composition for the prevention, amelioration or treatment of a disease of the central nervous system and/or diseases related and/or caused by said disease of the central nervous system. Furthermore, methods for preventing, ameliorating and/or treating such diseases are disclosed.

Several documents are cited throughout the text of this specification. The disclosure content of each of the documents cited herein (including any manufacturer's specifications, instructions, etc.) are hereby incorporated by reference.

The current model for the initiation of T cell-mediated inflammatory disease of the CNS includes peripheral antigen-specific T cell activation and Th1 differentiation (Martin, 1992; Miller, 1994; Zamvil, 1990). A peripheral T cell activation step appears to be required for autoreactive T cells to enter the CNS via the blood-brain barrier (Wekerle, 1986). The process of lesion formation is further governed by a complex pattern of cyto- and chemokine expression upon restimulation of autoreactive T cells in situ (Hoffman, 1998; Karpus, 1999). It is widely accepted that Th1 cells, critical for cell-mediated immunity by their production of IL-2, IFN-gamma, TNF-alpha and lymphotoxin are involved in the immunopathology of organ-specific autoimmune disease (Liblau, 1995; Raine, 1995 Steinman, 1997). A role as regulators has been suggested for Th2 cells (Mathisen, 1997; Nicholson, 1995; Racke, 1994) and cells producing Transforming-growth-factor-beta (TGF-beta) (Chen, 1996; 1994; O'Garra, 1997; Weiner, 1994).

TGF-beta belongs to a family of peptides with pleiotropic effects widely distributed throughout the body (Sporn, 1989) and in particular in the immune system (Letterio, 1998). In addition to the TGF-betas, bone morphogenetic proteinis (BMP) and activin make up the BMP-superfamily (Miyazono, 2001).

The three isotypic TGF-betas are extremely well conserved across species with a greater than 99% identity between the mature TGF-beta1 sequences of various mammalian species (Derynck, 1986; 1987). TGF-betas have important roles in cell growth and differentiation, organ development, matrix formation, wound repair and immune function (Blobe, 2000; Chen, 2001; Letterio, 2000).

TGF-beta regulates cellular processes by binding to three high-affinity cell-surface receptors known as types I, II and III. The type III receptors are the most abundant receptor type. They bind TFG-beta and transfer it to its signaling receptors, the type I (RI) and II (RII) receptors. Upon binding of a ligand to a type II receptor, type II receptor kinases phosphorylate serine and threonine residues within the intracellular GS (glycine-serine-rich) domain of type I receptors, leading to activation of the type I receptor. The activated TGF-betaRI then interacts with an adaptor molecule SARA (Smad anchor for receptor activation) (Tsukazaki, 1998), which facilitates the access of particular members of the Smad family of proteins, called receptor-regulated Smads (R-Smads) to activated TGF-beta receptors. The activated type I receptor kinases then phosphorylate R-Smads differentially at two serine residues at their extreme C termini (summarized in Itoh, 2000). R-Smads include Smad1, -2, -5 and -8 proteins. Smad2 and -3 mediate the signaling of TGF-beta and activins; and Smad8 mediates the signaling of ALK-2 receptor kinases (Baker, 1996; Lagna, 1996; Liu, 1996; Zhang, 1996, 1997).

Inhibitory Smads (I-Smads) consist of vertebrate Smad6 and Smad7 and Drosophila daughters against dpp (Dad). Unlike R-Smads, which augment the signaling of TGF-beta molecules, I-Smads inhibit TGF-beta superfamily signaling. Whereas Smad6 appears to inhibit BMP signaling preferentially, Smad7 acts as a general inhibitor of TGF-beta family signaling (Itoh, 1998; Souchelnytskyi, 1998; Ishisaki, 1999). I-Smads can bind stably to the intracellular domain of activated type I receptors, thereby inhibiting further signal transduction by preventing the phosphorylation of R-Smads by the receptor (Imamura, 1997; Inoue, 1998; Souchelnytskyi, 1998).

The expression of I-Smads appears to be part of a negative feedback loop. The expression of Smad6 and -7 can be induced rapidly and in some cases directly by BMP, activin and/or TGF-beta in cultured cells. In addition, Smad3 and -4 can directly bind to the Smad7 promoter to mediate activation of this promoter by activin or TGF-beta. (Nagarajan, 1999; von Gersdorff, 2000). In addition to stimulation through the TGF-beta-Smad pathway, Smad7 expression can also be induced by IFN-gamma through the Jak/Stat pathway (Ulloa, 1999), by TNF-alpha through activation of NF-kappaB (Bitzer, 2000), and by norepinephrine also through NF-kappaB (Kanamaru, 2001).

In addition to the function of Smad7 as an inhibitor of the phosphorylation of R-Smads by type I receptors at the cytoplasm/cell membrane border, Smad7 was also found to occur abundantly in the nuclei of certain cells and to be exported from the nucleus upon TGF-beta stimulation or a change in cell substrate (Itoh, 1998; Zhu, 1999). Pulaski (2001) showed that mutation in a major phosphorylation site of Smad7 at Ser-249 did not affect the inhibitory effect of Smad7 on TGF-beta or BMP7 signalling and did not interfere with nuclear localization of Smad7. Instead, phosphorylation of Smad7 at Ser-249 was shown to be important for its ligand-independent ability to regulate transcription.

Mice overexpressing Smad7 exhibit defective T cell responses to TGF-beta1, show markedly greater cytokine production in vitro, and show enhanced antigen-induced airway inflammation (Nakao, 2000). Smad7 has been shown to be overexpressed in inflammatory bowel disease (IBD) mucosa and purified mucosal T cells. In an in vitro system specific antisense oligonucleotides for Smad7 reduced Smad7 protein expression in cells isolated from IBD patients, permitting the cells to respond to exogenous TGF-beta (Monteleone, 2001).

WO 97/30065 identifies a cDNA (fchd540) encoding for Smad7 and discusses the upregulation of Smad7 in cardiovascular disease states. Diseases targeted by methods described in WO 97/30065 relate to cardiovascular disorders, in particular artherosclerosis, ischemia/reperfusion, hypertension, restenosis and arterial inflammation, as well as fibroproliferative oncogenic disorders, including diabetic retinopathy, cancer, tumorigenesis, vascularization of tumors, angiogenesis, artherosclerosis, inflammation and fibrosis.

WO 98/53068 also describes nucleic acid molecules encoding Smad7 and provides methods for decreasing or increasing TGFbeta superfamily signal transduction in mammalian cells based on targeting smad7 genes, gene products or interacting partners. Furthermore, methods for treating a subject suffering from lung cancer characterized by elevated expression of a Smad6 gene or a Smad7 gene are described. These methods involve administering to the subject an amount of an antisense nucleic acid which binds to the expression product of the Smad 6 or Smad7 gene effective to reduce the expression of the gene.

In addition, medical methods for reducing eye defects in a developing mammalian embryo are disclosed. These methods include contacting the cells of the embryo with an agent which reduces the expression or activity of a Smad7 nucleic acid molecule or an expression product thereof.

WO 01/53313 describes antisense compounds, compositions and methods are provided for modulating the expression of Smad7. The invention describes a method of treating a human having a disease or condition associated with Smad7 comprising administering to said animal a therapeutically or prophylactically effective amount of the antisense compound so that expression of Smad7 is inhibited. In the following "sub-claims" said disease or condition is a developmental disorder, a cardiovascular disorder, a hyperproliferative disorder or a wound healing disorder.

WO 01/21794 describes Smad associating polypeptides identified by yeast two hybrid screening. It is said that this invention further provides methods for reducing or increasing TGF-beta family signal transduction in a cell. It is mentioned that, in vivo, such methods are useful for modulating growth, e.g., to treat cancer and fibrosis. In addition it is stated that such methods are also useful in the treatment of conditions which result from excessive or deficient TGF-signal transduction. In WO 00177168 antagonists of BMP and TGF-β signaling pathways are disclosed whereby these antagonists relate to Smurf1 and Smurf2, capable of interacting with Smad1, 5 and 7. Smurf1 and Smurf2 are HECT type E3 ubiquitin ligases, containing the N-terminal C2 domain, followed by WW domains and the C-terminal HECT domain. The HECT domain is responsible for the E3 ligase activities of Smurfs. Interaction of Smurfs with I-Smads leads to nuclear export of the latter. In the cytoplasm, the C2 domain might target I-Smads to the cell membrane, and facilitate the interaction of I-Smads with TGFbeta receptors. Smurfs do not only recognize I-Smads as substrates, but also capture TGFbeta receptors as their targets, thereby leading to the degradation of both I-Smads and the receptor complexes (Ebisawa, 2001, Kavsak, 2000, Suzuki, 2002).

WO 00/77168 describes a protein Smurf2 which induces degradation of TGF-beta-receptors and Smad7. According to said application Smurf2 directly interacts with Smad7 via a PPXY motif in Smad7. Smurf2 is involved with TGF-beta receptor degradation acting in partnership with Smad7 as an antagonist or negative regulator of TGF-beta signalling. Activation of TGF-beta signalling results in Smad7-dependent recruitment of Smurf2 to the TGF-beta receptor complex. In the absence of activated TGF-beta receptor complex, Smurf2 does not alter the steady state level and turnover of Smad7. Recruitment of Smurf2 to the TGF-beta receptor by Smad7 promotes the degradation of the Smad7-TGF-beta receptor complex by both proteasomal and lysosomal pathways. It is stated that overexpression of Smurfs by gene therapy may be used to correct clinical conditions that result from excessive Smad signaling.

Other proteins found to interfere with Smad7 comprise YAP65 and TIEG. Yes-Associated Protein (YAP65) is a proline rich phosphoprotein originally identified as a protein binding to the SH3 domain of the Yes proto-oncogene product (Sudol, 1994). Ferrigno et al. identified YAP65 as novel Smad7-interacting protein through yeast two hybrid screening (Ferrigno, 2002). They showed in COS-7 cells that YAP65 potentiates the inhibitory activity of Smad7 against TGFbeta-induced, Smad3/4 dependent, gene transactivation. Furthermore, YAP65 was shown to augment the association of Smad7 to activated TGFbeta receptor type 1 molecules. TGF-beta inducible early gene (TIEG) is a zinc finger Krüppel-like transcription factor (KLF) and is induced by TGFbeta in many cell types (Subramaniam, 1995, Subramaniam, 1998). Overexpression of TIEG mimics effects of TGFbeta in many cell types (Chalaux, 1999, Hefferan, 2000, Ribeiro, 1999, Tachibana, 1997). TIEG has been shown to modulate the TGFbeta/Smad signaling pathway by binding to the Smad7 promoter and thereby repressing the Smad7 transcription. In addition TIEG increases transcription of the Smad2 gene. An E3 ubiquitin ligase, Seven in Absentia homologue-1 (SIAH1), acts as a TIEG1 interacting protein and induces degradation of TIEG1, thereby limiting the duration and/or magnitude of TGFbeta responses (Johnsen, 2002a, Johnsen, 2002b, Johnsen, 2002c).

Other TGF-β pathway genes are described in WO 98145467 and WO 01/16604 describes a method for screening for agents which are capable of modulating TGF-β cell signalling.

Relevant to autoimmune disease in the central nervous system (CNS) such as multiple sclerosis (MS) the immunosuppressive effects of TGF-beta were extensively investigated in vitro using myelin-specific autoimmune T cells, and in vivo, taking advantage of experimental autoimmune encephalomyelitis (EAE), which is the prime model for the human disease MS.

EAE can be induced in susceptible animal strains (e.g. rodents and primates) either by immunization (=active EAE) with a myelin antigen in complete or incomplete Freund's adjuvant (CFA) or by adoptive systemic transfer of autoreactive T cells obtained from animals previously immunized and activated in vitro with the respective autoantigen (at-EAE) (Brocke, 1996; Zamvil, 1990).

The endogenous TGF-beta production was shown by most authors to be upregulated in the CNS and presumably play a downmodulatory role during the recovery phase of acute EAE (Khoury, 1992; Racke, 1992; Issazadeh, 1995; Issazadeh, 1998). No upregulation of TGF-beta was found by Okuda (1995). In later work, however, a reduction of TGF-beta expression in the preclinical and acute phase in lymph node cells of mice immunized with myelin antigen in CFA (Complete Freunds Adjuvant) as compared to control mice treated with CFA alone was found (Okuda, 1998). Immunizing DA-rats (dark agouti rats) with rat spinal cord in incomplete Freund's adjuvant causes a prolonged chronic and relapsing course of EAE featuring extensive demyelination. While TGF-beta expression was described to be upregulated in the CNS of Lewis rats during the remission phase of (monophasic) EAE, a significant expression of regulatory cytokines such as TGF-beta (and IL-4 and IL-10) was not found in the DA rat CNS or lymphoid tissues at various time points (Issazadeh, 1996). Cytokine analysis demonstrated that the mRNA expression of IL-10 and TGF-beta1 was generally low in both acute EAE and the first attack of chronic EAE and upregulated at later stages of chronic EAE. It was suggested that anti-inflammatory cytokines play only a minor role in the relapse (Tanuma, 2000).

Recovery of disease in mice transgenic for an MBP-specific T cell receptor induced to develop EAE was associated with an immune deviation of Th1 T cells towards cells that secreted IL4, IL-10, and TGF-beta both in the periphery and in the CNS [Chen, 1998]. Kiefer and colleagues carried out a systematic study of TGF-beta expression (Kiefer, 1998). In actively induced monophasic EAE in the Lewis-rat, in situ hybridization revealed strong expression of TGF-beta1 in meningeal and perivascular mononuclear infiltrates at onset of the disease, continued expression in perivascular infiltrates and scattered mononuclear cells at maximal disease severity, and expression in scattered parenchymal cells during recovery. Cellular expression of TGF-beta1 by T-cells, macrophages, and microglia summed up to a long-lasting elevation of TGF-beta1 mRNA extending well into the recovery phase. While TGF-beta1 expressed early in the disease by T-cells was thought to contribute to inflammatory lesion development, its expression by microglial cells was suggested to potentially contribute to recovery (Kiefer, 1998).

Recombinant human TGF-beta1 administered at 2 µg daily. i.p. for two weeks after the last of several immunizations of SJL-mice with spinal cord homogenate in CFA delayed but did not prevent or significantly ameliorate the severity of the first disease episode in this EAE-model. Treatment after the first attack during a repeat immunization protocol reduced the severity of booster-immunization induced second episodes. Injections of TGF-beta1 initiated after the onset of an acute episode of EAE did not noticeably influence the course of that episode (Kuruvilla, 1991). However, in the same model spontaneous relapses were very efficiently blocked by daily treatment initiated 35 days after the onset of the first attack and maintained for 4 weeks (Kuruvilla, 1991). Using TGF-beta1 purified from human platelets it was subsequently shown that 1 pg of TGF-beta1 administered i.v. on days 1-5 after transfer of encephalitogenic lymph node cells in SJL-mice partially prevented EAE and significantly ameliorated disease scores mainly during the first and second disease attacks (Racke, 1991). Histology of TGF-beta1-treated mice sacrificed at day 7 post transfer revealed markedly reduced inflammation and absence of demyelination as opposed to mice treated with placebo. When TGF-beta1 treatment was initiated at the earliest signs of clinical disease and continued for 5 days the severity of subsequent relapses was reduced (Racke, 1991; Johns 1991). Treatment with recombinant simian TGF-beta 2 resulted in similar inhibition of T cell activation and proliferation in vitro.

Recent studies showed that adoptive transfer of activated MBP-specific Th1 clones transduced to secrete latent TGF-beta1 delayed and ameliorated EAE-signs in mice immunized with PLP (Chen, 1998). This strategy allowed for site-specific local delivery of therapeutic active TGF-beta1 to the CNS inflammatory infiltrates, was antigen-specific, yet apparently allowed bystander immunosuppression by T cells activated in situ (Chen, 1998; Thorbecke, 2000).

EAE was also successfully inhibited by a single injection of a cytokine (IL-4, IFN-beta, or TGF-beta) DNA-cationic liposome complex directly into the central nervous system (Croxford, 1998). In another study a prolonged continous TGF-beta delivery was reached by injection of a naked plasmid DNA expression vector encoding TGF-beta1 intramuscularly. This resulted in production of TGF-beta1 and protection from clinical and histopathological signs of MBP-induced EAE (Piccirillo and Prud'homme, 1999). Low doses of TGF-beta1 administered nasally inhibited development and relapses of chronic-relapsing EAE in DA rats.

Anti-TGF-beta1 antibody treatment in vivo aggravated EAE-severity (Miller, 1992; Racke, 1992; Santambrogio, 1993; Johns, 1993; Santambrogio, 1998).

TGF-beta 1 and 2 mRNA-expression in CNS tissue from MS cases, demonstrated by in situ hybridization, was found mainly in perivascular rather than parenchymal cells, suggesting circulating inflammatory cells as the major source (Woodroofe, 1993). In summary, they found both a stronger expression and a differently localized cellular distribution in MS (active demyelinating and chronic active and inactive lesions) as opposed to control tissue.

In a bioassay from peripheral blood cultures, TGF-beta like activity was found to be increased in patients with active disease as opposed to those with inactive disease and healthy donors and was found in particular in the subgroup tested during the regression of symptoms (Beck, 1991). Decreased TGF-beta production by lymphocytes of patients with MS correlated directly with disease activity. MS patients with active disease produced less TGF-beta than MS patients with stable disease. The cells producing TGF-beta were primarily CD8+ T cells and CD45RA+T cells (Mokhtarian, 1994).

Using a semiquantitative PCR the expression of TGF-beta and IL-10 was reported to decrease prior to a relapse while the expression of TNF-alpha and lymphotoxin increased (Rieckmann, 1995).

In an open-label phase 1 trial of 11 patients with secondary progressive (SP) MS the safety of recombinant active TGF-beta2 was assessed (Calabresi, 1998).

There is increasing evidence that the powerful anti-inflammatory properties of TGF-beta as a negative regulator of T-cell immune response play a key role in the pathophysiology of cerebral ischemia and other CNS pathologies (Benveniste, 1998, Kulkarni, 1993). Increased expression of TGF-beta was demonstrated in post mortem brain tissue of human stroke victims (Krupinski, 1996), and in brain biopsies from patients suffering from various acute or chronic neurodegenerative disorders including stroke, Parkinson's disease, or Alzheimer disease (Mattson, 1997, Pratt, 1997). Therefore, this cytokine is regarded as an injury-related peptide and a potential target for therapeutic intervention (Kriegistein, 1998).

In vitro data support a neuroprotective role of the TGF-beta pathway with particular reference to NMDA-induced neuronal death in excitotoxic paradigms such as hypoxia-ischemia (Buisson, 1998, Choi, 1996, Prehn, 1993). On the contrary, findings from in vivo-studies consistently describe induction of TGF-beta1 mRNA expression within hours after focal brain ischemia and upregulation persisting for several weeks after the insult (Lehrmann, 1998, Ruocco, 1999, Wang, 1995). More detailed data by Ali and coworkers(Ali, 2001) localized the significantly enhanced expression of TGF-beta1 to the ischemic penumbra, i.e. to the transitional metabolic zone between the ischemic core and the periinfarct zone. As blocking of the biological activity of TGF-beta by a specific antagonist increased both excitotoxic and ischemic lesions, data derived from rodent stroke models suggest that activation of the TGF-beta signaling pathway may be associated with neuroprotection (Ali, 2001, Ruocco, 1999).

In vivo data from a stroke model in rat identifying the cellular source of TGF-beta1 production after focal cerebral ischemia, demonstrated early induction as well as long-term upregulation of TGF-beta1 mRNA expression confined to activated microglia and macrophages. Therefore, TGF-beta1 mediated functions represent an immediate and persistent response in the acute ischemic brain lesion and are involved in the phase of tissue remodeling after stroke (Lehrmann, 1998). More detailed, a biphasic expression of TGF-beta1 with a first peak at 12 hours and at 7 days after permanent MCA occlusion in the infarcted tissue has been reported, the latter most probably linked to the downregulation of inflammatory tissue response, the induction of neoangiogenesis, and glial scar formation (Logan, 1994, Yamashita, 1999). The upregulation of TGF-beta1 gene expression extends from 3 hours to 4 days after transient forebrain ischemia (Zhu, 2000), up to 15 days after permanent MCA occlusion (Wang, 1995), and from 6 hours to 21 days after global brain ischemia (Lehrmann, 1995), respectively.

Data from in vivo studies concerning the intraarterial or the intracerebroventricular application of TGF-beta1 showed both treatment before (Gross, 1993) and after induction of pathology (Gross, 1994, McNeill, 1994) to be associated with a significant reduction of neuronal loss and infarct size in a rabbit model of thromboembolic stroke or a rat model of severe hypoxic-ischemic brain injury, respectively. In transient global ischemia in rats, Henrich-Noack and colleagues were able to show significant protection of pyramidal CA1 cells by intrahippocampal injection of TGF-beta1 prior to ischemia (Henrich-Noack, 1996). In mice overexpressing TGF-beta1 after adenoviral gene transfer Pang and coworkers (2001) demonstrated a reduction of infarct volume, associated with an inhibition of the inflammatory response to MCA occlusion in terms of reduced leukocyte and monocyte/macrophage infiltration into the ischemic brain tissue (Pang, 2001).

Highly elevated levels of TGF-beta1 mRNA were also reported for the ischemic penumbra in brain samples of human stroke victims (Krupinski, 1996). Furthermore, the enhanced expression of several TGF-beta isoforms and of the type I receptor protein in reactive processes surrounding ischemic brain lesions was demonstrated in human autopsy and biopsy material (Ata, 1997). While TGF-beta1 serum levels were not significantly different in stroke patients and healthy volunteers, a close correlation between TGF-beta1 levels and both clinical and neuroradiological parameters of brain injury have been reported (Kim, 1996, Slevin, 2000, Stanzani, 2001).

Experimental traumatic brain injury (TBI) results in a rapid and significant necrosis of cortical tissue at the site of injury. In the following hours and days, secondary injury exacerbates the primary damage resulting in significant tissue destruction and neurological dysfunction (Faden, 1993). Alterations in excitatory amino acids, increased oxidative stress and increased apoptosis contribute to progressive neuronal death following TBI. (summarized in (Sullivan, 2002) and ref. therein). Rimaniol et al. described a biphasic production of TGFbeta following cerebral trauma, with a first peak after 30 min. and a second peak 48 h after the lesion (Rimaniol, 1995). Lindholm et al. showed increased production of TGFbeta1 mRNA in the rat cerebral cortex after a penetrating brain injury (Lindholm, 1992). In this paper they argued that TGF-beta1 expressed in the lesioned brain may play a role in nerve regeneration by stimulating nerve growth factor (NGF) production and by controlling the extent of astrocyte proliferation and scar formation Logan et al. showed a diffuse increase of TGFbeta1 mRNA and protein around the cerebral stab wound at 1, 2 and 3 days; at 7 and 14 d after lesion the distribution was more localized to the region of the glial scar (Logan, 1992). They suggested to use TGFbeta1 antagonists to limit the pathogenesis associated with matrix deposition in the CNS wound. Kriegelstein et al. showed that the survival promoting effect of Glial cell line-derived neurotrophic factor (GDNF) in vivo and in vitro requires the presence of TGFbeta (Krieglstein, 1998). In a very recent study, Peterziel et al. demonstrated that the TGFbeta induced GDNF responsiveness in neurons is caused by the TGFbeta induced recruitment of the gycosyl-phosphatidyl-inositol-anchored GDNF receptor (GFR)alpha1 to the plasma membrane (Peterziel, 2002).

TGF-beta is present in senile amyloid plaques found in the CNS and is overexpressed in Alzheimer's disease brain compared with controls (Finch, J. Cell Biochem 53 (1993), 314-322). TGF-beta has been implicated in Alzheimer's disease pathogenesis (Wyss-Coray, Nature 389 (1997), 603-606; Flanders, Neurology 45(8) (1995), 1561-1569; van der Wal, Neuroreport 4 (1993), 69-72) for the following reasons: It accelerates amyloid deposition in an animal model of Alzheimer's disease; i.e. transgenic mice coexpressing human TGF-beta1 and mutated amyloid precursor protein (APP) (Finch, (1993) loc. cit.; Wyss-Coray, (1997), loc. cit.; Wyss-Coray, Ann. N.Y. Acad. Sci. 903 (2000), 317-323). TGF-beta drives astrocytic overexpression of mRNA encoding for the APP. On a molecular level, TGF-beta activation of Smad protein complexes promotes transcription of the APP gene (Burton, Biochem. Biophys. Res. Commun. 295 (2002), 702-712; Burton, Biochem. Biophys. Res. Commun. 295 (2002); 713-723). However, it has been shown in contrast by Wyss-Coray and coworkers (2001) that a modest increase in astroglial TGF-beta1 production in aged transgenic mice expressing the human beta-APP significantly reduces the number of parenchymal amyloid plaques and the overall cortical amyloid-beta load and decreases the number of dystrophic neuritis (Wyss-Coray, Nat. Med. 7(5) (2001), 612-618). In human APP/TGF-beta1-expressing mice, amyloid beta accumulated substantially in cerebral blood vessels, but not in parenchymal plaques (Wyss-Coray, (2001) loc. cit.). In human Alzheimer cases, plaque-associated amyloid beta immunoreactivity was inversely correlated with vascular amyloid beta and cortical TGF-beta1 mRNA levels. The reduction of parenchymal plaques in human APP/TGF-beta1 mice was associated with a strong activation of microglia and an increase in inflammatory mediators. Recombinant TGF-beta1 stimulated amyloid-beta clearance in microglial cell cultures (Wyss-Coray, (2001), loc. cit.).

However, research on TGF-beta uncovered ambiguous or detrimental effects of TGF-beta, last but not least from the perspective of autoimmune therapy; TGF-beta is considered in the art as a "two-edged sword". Kiefer (1998), analyzing TGF-beta expression in monophasic EAE of the Lewis rat, found evidence for early expression in T cells, possibly contributing to inflammatory lesion development while the later occurring expression within microglia was suggested to play a downmodulatory role. When Ag-specific murine T cell lines and clones were cultured in the presence of TGF-beta the effector function of these autoreactive cells and demyelinating lesion formation upon adoptive transfer in experimental autoimmune encephalomyelitis were markedly enhanced (Weinberg 1992). In another EAE model it was shown that the effects of TGF-beta on autoimmune disease expression vary depending on the timing of treatment with respect to disease induction. Daily i.p. injections of 0.2-2 µg TGF-beta 1 or TGF-beta 2 on days 5 to 9 after immunization were highly protective, while injections on days 1-5 or 9-13 were not. TGF-beta treatment on days 5-9 prevented the accumulation of T cells in brain and spinal cord, as assayed on days 15 to 20. Anti-TGF-beta accelerated and aggravated EAE when administered on days 5 and 9, but not on day 12. It was concluded that the protective effect of TGF-beta is exerted at the level of the target organ, CNS and/or its vascular endothelium and that there was a small window of 4 days in which TGF-beta exerts its protective effect (Santambrogio, 1993).

Mice genetically targeted to overexpress bioactive TGF-beta1 specifically within astrocytes were reported to show a phenotype with severe CNS pathology at high levels of expression. While unmanipulated heterozygous transgenic mice from a low expressor line showed no such alterations, increasing TGF-beta 1 expression in this line by injury-induced astroglial activation or generation of homozygous offspring did result in the abnormal phenotype (Wyss-Coray, 95). Astroglial overexpression of TGF-beta 1 was not associated with obvious. CNS infiltration by hematogenous cells (Wyss-Coray, 1995). However, these mice were more susceptible to EAE-induction with earlier and more severe CNS inflammation. Thus, local expression of TGF-beta 1 within the CNS parenchyma can enhance immune cell infiltration and intensify the CNS impairment resulting from peripherally triggered autoimmune responses (Wyss-Coray 1997). An Alzheimer's disease-like pathology with perivascular astrocytosis and deposition of amyloid in cerebral blood vessels was observed in older mice expressing low-levels of transgenic active TGF-beta (Wyss-Coray, 2000).

Various strategies that were successful in modulating EAE and suggested TGF-beta as part of the protective effect proved not to be effective or showed considerable toxicity in clinical trials. In an open-label phase 1 trial of 11 patients with secondary progressive (SP) MS the safety of recombinant active TGF-beta2 was assessed (Calabresi, 1998). Groups of patients were treated in a dose-escalation scheme with 0.2 μg/kg, 0.6 μg/kg or 2.0 μg/kg. Treatment was administered i.v., three times weekly for four weeks unless discontinued earlier. A reversible decline in the glomerular filtration rate developed in five patients (three with 0.6 μg/kg, both with 2.0 μg/kg), transient mild to moderate anemia in seven, hypertension in two and a maculopathy in one patient. The nephrotoxicity and anemia were likely to be related to TGF-beta-treatment. A beneficial effect or an effect on clinical or imaging parameters was not observed (Calabresi, 1998).

These indications of systemic side-effects considerably lessened the interest in TGF-beta as a therapeutic tool for MS (Calabresi 1998; Wiendl 2000). In addition, in a phase III clinical trial of oral myelin tolerization in RRMS neither clinical nor MRI outcome parameters were significantly different between myelin and placebo-treated patients (Panitch 97, Francis 97).

However, it has also been shown that it is considerably more difficult to treat ongoing EAE by mucosal tolerization (discussion in Xu 2000) or TGF-beta itself (discussion in Thorbecke 2000) than to prevent disease.

While TGF-beta is one of the most potent growth-inhibitory substances known for most cell types, it stimulates proliferation of fibroblasts and osteoblasts. It is also a potent stimulator of extracellular matrix production by fibroblasts and osteoblasts (Massague, 1987; Sporn, 1987), inhibits matrix degradation and upregulates receptors for matrix interaction TGF-beta1 has been implicated as a key causative factor in the pathogenesis of liver fibrosis (Border, 1994; Friedman, 1993) and at least as one crucial mediator of both the beneficial and detrimental effects of cyclosporine A on the immune system and the kidney (reviewed in (Khanna, 1999)). In addition, various chronic progressive fibrotic kidney disorders in humans and experimental models—be they glomerular or tubulointerstitial—have been shown to be associated with stimulation of the TGF-beta system (Bitzer, 1998). Administration of a neutralizing anti-TGF-beta-antibody resulted in the prevention of renal failure, excess matrix gene expression and glomerular mesangial matrix expansion in db/db diabetic mice (Ziyadeh, 2000).

Chronic TGF-beta upregulation plays a central role in progressive matrix accumulation and renal insufficiency observed in diabetic nephropathy (reviewed in Sharma and McGowan, 2000). The pathology of systemic multidose administration of recombinant human TGF-beta1 in rats and rabbits was described by Terrell (1993): A 14 day pilot study was performed in rats using rhTGF-beta1 produced in human A293 cells. After administration of 1000 μg/kg i.v. two rats died after 5 days. The remaining rats were sacrificed at that point. The mid-dose and low-dose-groups group received 100 μg/kg and 10 μg/kg i.v. daily for 14 days, respectively. Adverse events were most striking in the high-dose group but qualitatively similar changes were seen at the mid-dose level albeit less severe and delayed in onset. Besides certain histopathological changes, the rats displayed reduced body weight (from day 3) and an increased hematocrit on day 3 with a subsequent decrease. In the discussion of their findings Terrell and associates stated that the relative severity and rapidity with which some of the observed changes—both clinical and histopathological such as the hepatic involution and the enostosis—occurred in the high-dose preparations was remarkable (Terrell, 1993).

The use of TGF-beta for immunomodulation in humans is severely limited by its toxicity, including excessive stimulation of matrix production, nephrotoxicity and other detrimental effects. TGF-beta has oncogenic potential and has been implicated in glomerulopathies, pulmonary fibrosis, scleroderma and chronic graft versus host disease. In addition, while TGF-beta is an extremely potent immunosuppressive cytokine, several lines of evidence indicate that chronic stimulation of TGF-beta expression—both disease-related or in transgenic animal models—can paradoxically lead to or enhance autoimmune inflammation.

Recently, a potential explanation has been put forward suggesting that upmodulation of the Smad7 leads to a paralysis of TGF-beta signaling (Monteleone, 2001). The in vitro analysis carried out by Monteleone 2001 proposes that blocking of Smad7 may be beneficial in chronic inflammatory bowel disease, a disorder neither related to nor associated with disorders of the CNS. However, immunologically, chronic inflammatory bowel disease (CIBD) differs in many important aspects from CNS autoimmune inflammation. While the CNS is anatomically separated and protected from most circulating cells and exogenous agents by the blood-brain-barrier conveying the so-called "immunological privilege" of the CNS, the normal gut contains a rich lymphoid compartment maintaining a physiological inflammation induced and sustained by enteric flora and food antigens. The gut's immune system constantly works to tolerize the individual against the ingested food and the normal enteric flora. This function is mediated by the special type of immune reactions induced in the gut, is related to the marked upregulation of TGF-beta after an antigen-specific oral challenge (Gonnella 1998) and represents the immunological background of "oral tolerization" against autoimmunity-inducing antigens from other tissues (such as myelin components) (Garside 2001). The gut's physiological inflammation is transformed in persistent destructive inflammation in chronic inflammatory bowel disease (Fiocchi 1998). Accordingly, while chronic inflammatory bowel diseases develop at the regular interface between the external world and the immune system and frequently cause further manifestations systemically (such as coagulation disorders) or in other organs such as joint or skin disease, the autoimmune inflammation and the manifestations of multiple sclerosis are limited to a rather secluded organ, the CNS. In addition, in TGF-beta1 knockout mice massive inflammatory lesions were found in several organs, including colon, but no significant histological lesions were seen in brain (Kulkarni, 1993).

Therefore, whereas the prior art has proposed the use of TGF-beta or an upregulation of TGF-beta signaling pathways for the treatment of infections, inflammations, or even tumor-formation, a corresponding systemic upregulation of TGF-beta has severe side-effects as described herein above.

There is a need in the art to develop effective drugs for the treatment of disorders of the CNS for in vivo therapy.

The solution to said technical problem is achieved by the embodiments characterized in the claims.

Accordingly, the present invention relates to the use of a specific inhibitor of Smad7 expression or function for the preparation of a pharmaceutical composition for the prevention, amelioration or treatment of a disease of the central nervous system and/or diseases related and/or caused by said disease of the central nervous system.

In accordance with the present invention, it has surprisingly be found that the neutralization or antagonization of Smad7 restores and/or positively modifies TGF-beta signaling pathways in cells in the nervous system without the side effects of TGF-beta treatment. Therefore, a medical intervention comprising Smad7 antagonists/inhibitors as described herein is therapeutically beneficial in the treatment of diseases of the nervous system, in particular of neurodegenerative disorders, autoimmune diseases as described herein, trauma or of stroke. The medical and therapeutical intervention as described herein is surprisingly not associated with the deleterious toxicity in various organs that have been documented in the prior art as being affected by systemic TGF-beta treatment.

The appended examples clearly document the beneficial systemical suppression of Smad7 which leads to a significant amelioration of diseases of the CNS, in particular of autoimmune diseases, like multiple sclerosis (MS) as well as conditions in which an inflammatory response makes a secondary contribution to tissue injury or repair such as trauma or (ischemic) stroke. Furthermore, the Smad7 inhibitors or antagonists as described herein are also useful in the treatment or prevention of neurodegenerative disorders, like Alzheimer's disease or Parkinson's disease.

Without being bound by theory, it is envisaged that pathways like the TGF-beta (BMP)-Smad signal transduction, the targeting of TGF-beta (BMP) receptors for proteolytic degradation via Smurf/ubiquitin ligase pathways, or the nuclear (or cytoplasmic) modulation of transcription events are positively modulated by the use of Smad7 inhibitors/antagonists as described herein. Particularly preferred is the use of these Smad7 antagonists/inhibitors in the treatment of CNS-disorders as described herein below. Most preferred is this use in the preparation of a pharmaceutical composition for the treatment of multiple sclerosis, ischemia, Alzheimer's disease, Parkinson's disease, stroke and trauma.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

In a particular preferred embodiment, the present invention relates to the use as described herein above, wherein said specific Smad7 inhibitor/antagonist is selected from the group consisting of (small) binding molecules, intracellular-binding-partners or receptors, aptamers, intramers, RNAi (double stranded RNA, siRNA) and anti-Smad7 antisense molecules. Furthermore, said specific inhibitor/antagonist to be employed in context of the present invention may comprise truncated and/or mutated Smad7 molecules which interfere with the Smad7 and which, thereby, inhibit Smad7 function.

(Small) binding molecules comprise natural as well as synthetic compounds. The term "compound" in context of this invention comprises single substances or a plurality of substances. Said compound/binding molecules may be comprised in, for example, samples, e.g., cell extracts from, e.g., plants, animals or microorganisms. Furthermore, said compound(s) may be known in the art but hitherto not known to be capable of (negatively) influencing the activity Smad7 or not known to be capable of influencing the expression of the nucleic acid molecule encoding for Smad7, respectively. The plurality of compounds may be, e.g., added to a sample in vitro, to the culture medium or injected into the cell.

If a sample (collection of compounds) containing (a) compound(s) is identified in the art as a specific inhibitory binding molecule of Smad7, then it is either possible to isolate the compound from the original sample identified as containing the compound in question or one can further subdivide the original sample, for example, if it consists of a plurality of different compounds, so as to reduce the number of different substances per sample and repeat the method with the subdivisions of the original sample. It can then be determined whether said sample or compound displays the desired properties, i.e. the inhibition of Smad7, by methods known in the art. Depending on the complexity of the samples, the steps described above can be performed several times, preferably until the sample identified according to the screening method only comprises a limited number of or only one substance(s). Preferably said sample comprises substances of similar chemical and/or physical properties, and most preferably said substances are identical.

Binding molecules/inhibitory molecules for Smad7 may be deduced by methods in the art. Such methods comprise, e.g., but are not limited to methods, where a collection of substances is tested for interaction with Smad7 or with (a) fragment(s) thereof and where substances which test positive for interaction in a corresponding readout system are further tested in vivo, in vitro or in silico for their inhibitory effects on Smad7 expression or function.

Said "test for Smad7 interaction" of the above described method may be carried out by specific immunological, molecular biological and/or biochemical assays which are well known in the art and which comprise, e.g., homogenous and heterogenous assays as described herein below.

Said interaction assays employing read-out systems are well known in the art and comprise, inter alia, two hybrid screenings (as, described, inter alia, in EP-0 963 376, WO 98/25947, WO 00/02911), GST-pull-down columns, co-precipitation assays from cell extracts as described, inter alia, in Kasus-Jacobi, Oncogene 19 (2000), 2052-2059, "interaction-trap" systems (as described, inter alia, in U.S. Pat. No. 6,004, 746) expression cloning (e.g. lamda gtII), phage display (as described, inter alia, in U.S. Pat. No. 5,541,109), in vitro binding assays and the like. Further interaction assay methods and corresponding read out systems are, inter alia, described in U.S. Pat. No. 5,525,490, WO 99/51741, WO 00/17221, WO 00/14271, WO 00/05410 or Yeast Four hybrid assays as described in Sandrok & Egly, JBC 276 (2001), 35328-35333.

Said interaction assays for Smad7 also comprise assays for FRET-assays, TR-FRETs (in "A homogenius time resolved fluorescence method for drug discovery" in: High throughput screening: the discovery of bioactive substances. Kolb, (1997) J.Devlin. NY, Marcel Dekker 345-360) or commercially available assays, like "Amplified Luminescent Proximity Homogenous Assay", BioSignal Packard. Furthermore, the yeast-2-hybrid (Y2H) system may be employed to elucidate further particular and specific interaction, association partners of Smad7. Said interaction/association partners are further screened for their inhibitory effects.

Similarly, interacting molecules (for example) (poly)peptides may be deduced by cell-based techniques well known in the art. These assays comprise, inter alia, the expression of reporter gene constructs or "knock-in" assays, as described, for, e.g., the identification of drugs/small compounds influencing the (gene) expression of Smad7. Said "knock-in" assays may comprise "knock-in" of Smad7 (or (a) fragment(s) thereof) in tissue culture cells, as well as in (transgenic) animals. Examples for successful "knock-ins"

are known in the art (see, inter alia, Tanaka, J. Neurobiol. 41 (1999), 524-539 or Monroe, Immunity 11 (1999), 201-212). Furthermore, biochemical assays may be employed which comprise, but are not limited to, binding of the Smad7 (or (a) fragment(s) thereof) to other molecules/(poly)peptides, peptides or binding of the Smad7 (or (a) fragment(s) thereof) to itself (themselves) (dimerizations, oligomerizations, multimerizations) and assaying said interactions by, inter alia, scintillation proximity assay (SPA) or homogenous time-resolved fluorescence assay (HTRFA).

Said "testing of interaction" may also comprise the measurement of a complex formation. The measurement of a complex formation is well known in the art and comprises, inter alia, heterogeneous and homogeneous assays. Homogeneous assays comprise assays wherein the binding partners remain in solution and comprise assays, like agglutination assays. Heterogeneous assays comprise assays like, inter alia, immuno assays, for example, ELISAs, RIAs, IRMAs, FIAs, CLIAs or ECLs.

As discussed below the interaction of the inhibiting molecules of Smad7 mRNA and Smad7 protein or fragments thereof may also be tested by molecular biological methods, like two-, three- or four-hybrid-assays, RNA protection assays, Northern blots, Western blots, micro-, macro- and Protein- or antibody arrays, dot blot assays, in situ hybridization and immunohistochemistry, quantitative PCR, coprecipitation, far western blotting, phage based expression cloning, surface plasmon resonance measurements, yeast one hybrid screening, DNAse I, footprint analysis, mobility shift DNA-binding assays, gel filtration chromatography, affinity chromatography, immunoprecipitation, one- or two dimensional gel electrophoresis, aptamer technologies, as well as high throughput synthesis and screening methods.

The compounds identified and/or obtained according to the above described method(s), in particular inhibitors of Smad7 or (a) fragment(s) thereof, are expected to be very beneficial as agents in pharmaceutical settings disclosed herein and to be used for medical purposes, in particular, in the treatment of the CNS-disorders described herein.

Compounds which may function as specific inhibition of Smad7 also comprise (small) organic compounds, like compounds which can be used in accordance with the present invention include, inter alia, peptides, proteins, nucleic acids including cDNA expression libraries, small organic compounds, ligands, PNAs and the like. Said compounds can also be functional derivatives or analogues. Methods for the preparation of chemical derivatives and analogues are well known to those skilled in the art and are described in, for example, Beilstein, "Handbook of Organic Chemistry", Springer Edition New York, or in "Organic Synthesis", Wiley, N.Y. Furthermore, said derivatives and analogues can be tested for their effects, i.e. their inhibitory effects of Smad7 according to methods known in the art. Furthermore, peptidomimetics and/or computer aided design of appropriate inhibitors of Smad7 can be used. Appropriate computer systems for the computer aided design of, e.g., proteins and peptides are described in the prior art, for example, in Berry, Biochem. Soc. Trans. 22 (1994), 1033-1036; Wodak, Ann. N. Y. Acad. Sci. 501 (1987), 1-13; Pabo, Biochemistry 25 (1986), 5987-5991. The results obtained from the above-described computer analysis can be used in combination with the method of the invention for, e.g., optimizing known compounds, substances or molecules. Appropriate compounds can also be identified by the synthesis of peptidomimetic combinatorial libraries through successive chemical modification and testing the resulting compounds, e.g., according to the methods described herein. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Furthermore, the three-dimensional and/or crystallographic structure of inhibitors of Smad7 can be used for the design of (peptidomimetic) inhibitors of Smad7 (Rose, Biochemistry 35 (1996), 12933-12944; Rutenber, Bioorg. Med. Chem. 4 (1996), 1545-1558).

As mentioned herein above, the inhibitor of Smad7 expression or function may also comprise an aptamer.

In the context of the present invention, the term "aptamer" comprises nucleic acids such as RNA, ssDNA (ss=single stranded), modified RNA, modified ssDNA or PNAs which bind a plurality of target sequences having a high specificity and affinity. Aptamers are well known in the art and, inter alia, described in Famulok, Curr. Op. Chem. Biol. 2 (1998), 320-327. The preparation of aptamers is well known in the art and may involve, inter alia, the use of combinatorial RNA libraries to identify binding sites (Gold, Ann. Rev. Biochem. 64 (1995), 763-797).

Accordingly, aptamers are oligonucleotides derived from an in vitro evolution process called SELEX (systematic evolution of ligands by exponential enrichment). Pools of randomized RNA or single stranded DNA sequences are selected against certain targets. The sequences of tighter binding with the targets are isolated and amplified. The selection is repeated using the enriched pool derived from the first round selection. Several rounds of this process lead to winning sequences that are called 'aptamers' or 'ligands'. Aptamers have been evolved to bind proteins which are associated with a number of disease states. Using this method, many powerful antagonists of such proteins can be found. In order for these antagonists to work in animal models of disease and in humans, it is normally necessary to modify the aptamers. First of all, sugar modifications of nucleoside triphosphates are necessary to render the resulting aptamers resistant to nucleases found in serum. Changing the 2'OH groups of ribose to 2° F. or 2'NH2 groups yields aptamers which are long lived in blood. The relatively low molecular weight of aptamers (8000-12000) leads to rapid clearance from the blood. Aptamers can be kept in the circulation from hours to days by conjugating them to higher molecular weight vehicles. When modified, conjugated aptamers are injected into animals, they inhibit physiological functions known to be associated with their target proteins. Aptamers may be applied systemically in animals and humans to treat organ specific diseases (Ostendorf, 2001). The first aptamer that has proceeded to phase I clinical studies is NX-1838, an injectable angiogenesis inhibitor that can be potentially used to treat macular degeneration-induced blindness. (Sun, 2000). Cytoplasmatic expression of aptamers ("intramers") may be used to inhibit intracellular targets (Blind, 1999; Mayer, 2001). Said intramers are also envisaged to be employed in context of this invention.

Said (other) receptors of Smad7 may, for example, be derived from (an) antibody(ies) against Smad7 by peptidomimetics. The specificity of the recognition implies that other known proteins, molecules are not bound. Further, Smad7-receptors which may function in context of this invention are SARA (Wu, 2000), STRAP (Datta, 2000), TGF-beta- or BMP-receptors or Smad2 (Kavasak, 2000). It is in particular envisaged that peptide fragments of such "natural" Smad7-receptors are employed.

The RNAi-approach is also envisaged in context of this invention for use in the preparation of a pharmaceutical composition for the treatment of CNS-diseases disclosed herein.

The term RNA interference (RNAi) describes the use of double-stranded RNA to target specific mRNAs for degradation, thereby silencing their expression. Double-stranded RNA (dsRNA) matching a gene sequence is synthesized in vitro and introduced into a cell. The dsRNA feeds into a natural, but only partially understood process including the highly conserved nuclease dicer (Hutvagner, 2001; Grishok, 2001), which cleaves dsRNA precursor molecules into short interfering RNAs (siRNAs). The generation and preparation of siRNA(s) as well as the method for inhibiting the expression of a target gene is, inter alia, described in WO 021055693, Wei (2000) Dev. Biol. 15, 239-255; La Count (2000), Biochem. Paras. 111, 67-76, Baker (2000) Curr. Biol. 10, 1071-1074, Svoboda (2000), Development 127, 4147-4156 or Marie (2000) Curr. Biol. 10, 289-292. These siRNAs built then the sequence specific part of an RNA-induced silencing complex (RISC), a multicomplex nuclease that destroys messenger RNAs homologous to the silencing trigger. One protein-part of the ribonucleoprotein complex has been identified as Argonaute2 (Hammond, 2001). Elbashir (2001) showed that duplexes of 21 nucleotide RNAs may be used in cell culture to interfere with gene expression in mammalian cells.

Methods to deduce and construct siRNAs are in the art and are described in Elbashir et al., 2002, at the internet web sites of commercial vendors of siRNA, e.g. Xeragon Inc. (www.xeragon.com/siRNA support.html); Dharmacon (www.dharmacon.com;); Xeragon Inc. (www.xeragon.com;), and Ambion (www.ambion.com), or at the web site of the research group of Tom Tuschl (http://www.mpibpc.gwdg.de/abteilungen/100/105/sirna.html). In addition, programs are available online to deduce siRNAs from a given mRNA sequence (e.g. http://www.ambion.com/techlib/misc/siRNA finder.html or http://katahdin.cshl.org:9331/RNAi/). These were used to deduce the siRNA molecules listed below (RNAi 1-20, SEQ ID NO: 44-83). Uridine residues in the 2-nt 3' overhang can be replaced by 2'deoxythymidine without loss of activity, which significantly reduces costs of RNA synthesis and may also enhance resistance of siRNA duplexes when applied to mammalian cells (Elbashir, 2001). This modification is also incorporated in citing SEQ Ids 44-83 (see below) of the present application. The siRNAs may also be sythesized enzymatically using T7 or other RNA polymerases (Donze, 2002). Short RNA duplexes that mediate effective RNA interference (esiRNA) may also be produced by hydrolysis with Escherichia coli Rnase III (Yang, 2002) Furthermore, expression vectors have been developed to express double stranded siRNAs connected by small hairpin RNA loops in eukaryotic cells (e.g. (Brummelkamp, 2002)). All of these constructs may by developed with the help of the programs named above. In addition, commercially available sequence prediction tools incorporated in sequence analysis programs or sold separately, e.g. the siRNA Design Tool offered by www.oligoEngine.com (Seattle, Wash.) may be used for siRNA sequence prediction.

Accordingly, the present invention also provides for the use of specific interfering RNAs as inhibitors of Smad7 expression and/or function. Preferably, said (small) interfering RNAs (siRNAs) comprise at least 10, more preferably at least 12, more preferably at least 14, more preferably at least 16, more preferably at least 18 nucleotides. In a particular preferred embodiment these siRNAs are selected from the group consisting of

| | | | | |
|---|---|---|---|---|
| RNAi1: | nt 298-318 | 5'-GUUCAGGACCAAACGAUCUGC-3', | (SEQ ID NO:44) |
| | nt 318-296 | 5'-GCAGAUCGUUUGGUCCUGAACAU-3', | (SEQ ID NO:45) |
| RNAi2: | nt 578-598 | 5'-CUCACGCACUCGGUGCUCAAG-3', | (SEQ ID NO:46) |
| | nt 598-576 | 5'-CUUGAGCACCGAGUGCGUGAGCG-3'; | (SEQ ID NO:47) |
| RNAi3: | nt 209-227 | 5'-CUCGGCGCCCGACUUCUUCuu-3', | (SEQ ID NO:48) |
| | nt 227-207 | 5'-GAAGAAGUCGGGCGCCGAGUU-3', | (SEQ ID NO:49) |
| RNAi4: | nt 266-284 | 5'-ACGACUUUUCUCCUCGCCUuu-3', | (SEQ ID NO:50) |
| | nt 284-264 | 5'-AGGCGAGGAGAAAAGUCGUUU-3'; | (SEQ ID NO:51) |
| RNAi5: | nt 310-328 | 5'-ACGAUCUGCGCUCGUCCGGuu-3', | (SEQ ID NO:52) |
| | nt 328-308 | 5'-CCGGACGAGCGCAGAUCGUUU-3'; | (SEQ ID NO:53) |
| RNAi6: | nt 574-592 | 5'-GGCGCUCACGCACUCGGUGuu-3', | (SEQ ID NO:54) |
| | nt 592-572 | 5'-CACCGAGUGCGUGAGCGCCUU-3'; | (SEQ ID NO:55) |
| RNAi7: | nt 607-625 | 5'-GGAGCGGCAGCUGGAGCUGuu-3', | (SEQ ID NO:56) |
| | nt 625-605 | 5'-CAGCUCCAGCUGCCGCUCCUU-3', | (SEQ ID NO:57) |
| RNAi8: | nt 778-796 | 5'-AGUGUUCAGGUGGCCGGAUuu-3', | (SEQ ID NO:58) |
| | nt 796-776 | 5'-AUCCGGCCACCUGAACACUuu-3', | (SEQ ID NO:59) |
| RNAi9: | nt 815-833 | 5'-GUCAAGAGGCUGUGUUGCUuu-3', | (SEQ ID NO:60) |
| | nt 833-813 | 5'-AGCAACACAGCCUCUUGACUU-3', | (SEQ ID NO:61) |
| RNAi10: | nt 820-838 | 5'-GAGGCUGUGUUGCUGUGAAuu-3', | (SEQ ID NO:62) |
| | nt 838-818 | 5'-UUCACAGACACACAGCCUCUU-3', | (SEQ ID NO:63) |

```
RNAi11:  nt 839-857    5'-UCUUACGGGAAGAUCAACCuu-3',    (SEQ ID NO:64)

nt 857-837    5'-GGUUGAUCUUCCCGUAAGAUU-3',    (SEQ ID NO:65)

RNAi12:  nt 850-868    5'-GAUCAACCCCGAGCUGGUGuu-3',    (SEQ ID NO:66)

nt 868-848    5'-CACCAGCUCGGGGUUGAUCUU-3',    (SEQ ID NO:67)

RNAi13:  nt 856-874    5'-CCCCGAGCUGGUGUGCUGCuu-3',    (SEQ ID NO:68)

nt 874-854    5'-GCAGCACACCAGCUCGGGGUU-3',    (SEQ ID NO:69)

RNAi14:  nt 1008-1026  5'-CGAAUUAUCUGGCCCCUGGuu-3',    (SEQ ID NO:70)

nt 1026-1006  5'-CCAGGGGCCAGAUAAUUCGUU-3',    (SEQ ID NO:71)

RNAi15:  nt 1046-1064  5'-CUUCUUCUGGAGCCUGGGGuu-3',    (SEQ ID NO:72)

nt 1064-1044  5'-CCCCAGGCUCCAGAAGAAGUU-3',    (SEQ ID NO:73)

RNAi16:  nt 1177-1195  5'-UGGCUUUUGCCUCGGACAGuu-3',    (SEQ ID NO:74)

nt 1195-1175  5'-CUGUCCGAGGCAAAAGCCAUU-3,     (SEQ ID NO:75)

RNAi17:  nt 1201-1219  5'-UUCGGACAACAAGAGUCAGuu-3',    (SEQ ID NO:76)

nt 1219-1199  5'-CUGACUCUUGUUGUCCGAAUU-3',    (SEQ ID NO:77)

RNAi18:  nt 1297-1315  5'-CCGCAGCAGUUACCCCAUCuu-3',    (SEQ ID NO:78)

nt 1315-1295  5'-GAUGGGGUAACUGCUGCGGUU-3',    (SEQ ID NO:79)

RNAi19:  nt 1324-1342  5'-GUCCGCCACACUGGACAACuu-3',    (SEQ ID NO:80)

nt 1342-1322  5'-GUUGUCCAGUGUGGCGGACUU-3',    (SEQ ID NO:81)

RNAi20:  nt 1342-1360  5'-CCCGGACUCCAGGACGCUGuu-3',    (SEQ ID NO:82)

nt 1360-1340  5'-CAGCGUCCUGGAGUCCGGGUU-3',    (SEQ ID NO:83)
``` sRNAi are used in pair combinations. The above pairs comprise SEQ ID NO:44 combined with SEQ ID NO:45 (RNAi1), and SEQ ID NO:46 combined with SEQ ID NO:47 (RNAi2), and are useful for the treatment of human patients. Further pairs envisonaged are: SEQ ID NO:48 combined with SEQ ID NO:49, SEQ ID NO:50 combined with SEQ ID NO:51, SEQ ID NO:52 combined with SEQ ID NO:53, SEQ ID NO:54 combined with SEQ ID NO:55, SEQ ID NO:56 combined with SEQ ID NO:57, SEQ ID NO:58 combined with SEQ ID NO:59, SEQ ID NO:60 combined with SEQ ID NO:61, SEQ ID NO:62 combined with SEQ ID NO:63, SEQ ID NO:64 combined with SEQ ID NO:65, SEQ ID NO:66 combined with SEQ ID NO:67, SEQ ID NO:68 combined with SEQ ID NO:69, SEQ ID NO:70 combined with SEQ ID NO:71, SEQ ID NO:72 combined with SEQ ID NO:73, SEQ ID NO:74 combined with SEQ ID NO:75, SEQ ID NO:76 combined with SEQ ID NO:77, SEQ ID NO:78 combined with SEQ ID NO:79, SEQ ID NO:80 combined with SEQ ID NO:81, SEQ ID NO:82 combined with SEQ ID NO:83.

As illustrated in the appended examples siRNAs are a powerfull approach in the treatment of CNS disorders.

In addition, novel methods to identify molecules useful to inhibit smad7 RNA or smad7 RNA/protein (smad7 RNP complexes), including nuclear magnetic resonance (NMR) and fluorescence binding assays, have been summarized in (Hermann, 2000) and (DeJong, 2002), and in the references cited therein.

In a preferred embodiment of the invention the intracellular binding partner or receptor of Smad7 expression and/or function is an intracellular antibody.

Intracellular antibodies are known in the art and can be used to neutralize or modulate the functional activity of the target molecule. This therapeutic approach is based on intracellular expression of recombinant antibody fragments, either Fab or single chain Fv, targeted to the desired cell compartment using appropriate targeting sequences (summarized in Teillaud, 1999).

As mentioned herein above, preferably the inhibitor of Smad7 expression and/or function is an antisense molecule. Preferably said anti-Smad7 antisense molecule comprises a nucleic acid molecule which is the complementary strand of a reversed complementary strand of the coding region of Smad7.

Coding regions of Smad7 are known in the art and comprise, inter alia, the Smad7 GenBank entries for mouse Smad7 NM_008543, AJ00551, AJ000550, the Smad7 rat sequences NM_030858, AH008243, AF156730, AF156729, AF156728, AF156727, AF156726, AF042499 or the human Smad7 sequences entries in GenBank as XM_033746, XM_008803, AF015261 or AF010193. The person skilled in the art may easily deduce the relevant coding region of Smad7 in these GenBank entries, which may also comprise the entry of genomic DNA as well as mRNA/cDNA.

Furthermore, it is also envisaged that the antisense molecules against Smad7 expression or function interfere specifically with promoter regions of Smad7. Such promoter regions are known in the art and comprise, inter alia, GenBank entries AF254791 (human), AF156731 (human) or AF188834 (mouse).

It is envisaged that the antisense molecules to be used in accordance with the present invention inhibit the expression or function of Smad7, in particular of human Smad7 and interact with Smad7 as expressed by the coding regions, mRNAs/cDNAs as deposited under the above mentioned GenBank accession numbers as well as with Smad7 as expressed by isoforms and variants of said Smad7. Said isoforms or variants may, inter.alia, comprise allelic variants or splice variants.

The term "variant" means in this context that the Smad7 nucleotide sequence and the encoded Smad7 amino acid sequence, respectively, differs from the distinct sequences available under said GenBank Accession numbers, by mutations, e.g. deletion, additions, substitutions, inversions etc.

Therefore, the antisense-molecule to be employed in accordance with the present invention specifically interacts with/hybridizes to one or more nucleic acid molecules encoding Smad7. Preferably said nucleic acid molecule is RNA, i.e. pre m-RNA or mRNA. The term "specifically interacts with/ hybridizes to one or more nucleic acid molecules encoding Smad7" relates, in context of this invention, to antisense molecules which are capable of interfering with the expression of Smad7. As illustrated in the appended examples, antisense constructs, like "Smad7-mut4-as" (an antisense construct comprising 4 mutations) is not capable of specifically interacting with and/or hybridizing to one or more nucleic acid sequences encoding Smad7. Accordingly, highly mutated anti-Smad7 antisense constructs, which are not capable of hybridizing to or specifically interacting with Smad7-coding nucleic acid molecules are not to be employed in the uses of the present invention. The person skilled in the art can easily deduce whether an antisense construct specifically interacts with/hybridizes to Smad7 encoding sequences. These tests comprise, but are not limited to hybridization assays, RNAse protection assays, Northern Blots, Northwestern blots, nuclear magnetic resonance and fluorescence binding assys, dot blots, micro- and macroarrays and quantitative PCR. In addition, such a screening may not be restricted to Smad7 mRNA molecules, but may also include Smad7 mRNA/protein (RNP) complexes (Hermann, 2000; DeJong et al., 2002). Furthermore, functional tests as provided in the appended examples are envisaged for testing whether a particular antisense construct is capable of specifically interacting with/hybridizing to the Smad7 encoding nucleic acid molecules. These functional assays comprise in vitro T-cell activation assays; see, inter alia, example 11. These functional tests may also include Western blots, immunohistochemistry, immunoprecipitation assay, and bioassays based on TGFbeta responsive promoters.

Yet, as also documented in the appended examples mutated and/or modified antisense constructs may also be employed in accordance with this invention, provided that said mutated and/or modified antisense constructs are capable of specifically interacting with and/or hybridizing to the coding sequences of Smad7.

Antisense molecules of Smad7 have been described in the prior art. For example, U.S. Pat. No. 6,159,697 describes antisense compounds comprising such antisense-molecules. Yet, U.S. Pat. No. 6,159,697 employs said compounds in the treatment of diseases which are associated with Smad7 expression. In contrast, the present invention provides for a specific medical/therapeutic intervention, where no diseases/ conditions associated with Smad7 expression are to be treated, but specific disorders of the central nervous system where the systemic administration of TGF-beta was shown to be detrimental.

The term "antisense-molecule" as used herein comprises in particular antisense oligonucleotides. Said antisense oligonucleotides may also comprise modified nucleotides as well as modified internucleoside-linkage, as, inter alia, described in U.S. Pat. No. 6,159,697.

Most preferably, the antisense oligonucleotides of the present invention comprise at least 8, more preferably at least 10, more preferably at least 12, more preferably at least 14, more preferably at least 16 nucleotides. The deduction as well as the preparation of antisense molecules is very well known in the art. The deduction of antisense molecules is, inter alia, described in Smith, 2000. Usual methods are "gene walking", RnaseH mapping, RNase L mapping (Leaman and Cramer, 1999), combinatorial oligonucleotide arrays on solid support, determination of secondary structure analysis by computational methods (Walton, 2000), aptamer oligonucleotides targeted to structured nucleic acids (aptastruc), thetered oligonucleotide probes, foldback triplex-forming oligonucleotides (FTFOs) (Kandimalla, 1994) and selection of sequences with minimized non-specific binding (Han, 1994).

Preferably, the antisense molecules of the present invention are stabilized against degradation. Such stabilization methods are known in the art and, inter alia, described in U.S. Pat. No. 6,159,697. Further methods described to protect oligonucleotides from degradation include oligonucleotides bridged by linkers (Vorobjev, 2001), minimally modified molecules according to cell nuclease activity (Samani, 2001), 2'O-DMAOE oligonucleotides (Prakash, 2001), 3'5'-Dipeptidyl oligonucleotides (Schwope, 1999), 3'methylene thymidine and 5-methyluridine/cytidine h-phosphonates and phosphonamidites (An, 2001), as well as anionic liposome (De Oliveira, 2000) or ionizable aminolipid (Semple, 2001) encapsulation.

In a preferred embodiment of the invention, the antisense molecule is a nucleic acid molecule which is the complementary strand of a reversed complementary strand of the coding region of Smad7 is selected from the group consisting of SEQ ID NO: 1, SEQ ID NO: 3 or SEQ ID NO: 5. Sequences as depicted in SEQ ID NOs: 1, 3 or 5 represent illustrative coding regions (mRNA) of human, mouse or rat Smad7. SEQ ID NOs: 2, 4 and 6 represent translated Smad7 of human, mouse or rat, respectively. Accordingly, in context of this invention and as stressed herein above, the Smad7 inhibitors to be employed in the uses described herein, preferably, interact with promoter and/or coding regions of nucleic acid molecules which code for or lead to the expression of Smad7 molecules or shown in SEQ ID NOs: 2, 4 or 6. It is also envisaged that, e.g., antisense constructs designed and used in accordance with this invention inhibit the expression of functional homologues, variants (for example allelic variants) or isoforms of Smad7-molecules as shown in SEQ ID NOs: 2, 4 or 6.

In context of this invention, the term "coding region of Smad7" comprises not only the translated region of Smad7 cds, but also comprises untranslated regions. Accordingly, the anti-Smad7 antisense molecule to be used and employed in accordance with this invention may be antisense molecules which bind to/interact with mRNA sequences comprising untranslated region. Accordingly, the "coding region of Smad7" as depicted in SEQ ID NO: 1, 3 and 5 comprises the full mRNA sequences of Smad7.

In a most preferred embodiment of the present invention, the anti-Smad7 antisense molecule to be employed in the uses of the invention or the methods described herein is selected from a nucleic acid molecule as shown in the following table:

Preferably, Smad7-Antisense Oligonucleotides, derived from mouse sequences (5'-3'-direction) are:

| | | |
|---|---|---|
| cttcggctgccccacccg | (SEQ ID NO: 7) | NM_008543, nt 1179-1196, 5'UT |
| atcgtttggtcctgaacat | (SEQ ID NO: 8) | NM_008543, nt 1437-1455, cds |
| ccctcctcctcgtcctcg | (SEQ ID NO: 9) | NM_008543, nt 1499-1516, cds |
| gtcgcccttctccccgcag | (SEQ ID NO. 10) | NM_008543, nt 1545-1564, cds |
| gccgtccgtcgcccttc | (SEQ ID NO: 11) | NM_008543, nt 1554-1571, cds |
| agcaccgagtgcgtgagc | (SEQ ID NO: 12) | NM_008543, nt 1718-1735, cds |
| agttcacagagtcgacta | (SEQ ID NO: 13) | NM_008543, nt 2030-2047, cds |
| ggcaaaagccattcccct | (SEQ ID NO: 14) | NM_008543, nt 2311-2328, cds |
| gccgatcttgctccgcac | (SEQ ID NO: 15) | NM_008543, nt 2373-2430, cds, cds |

Relevant mouse Smad7 Genbank entries are NM_008543 (mRNA sequence) and AJ000551 (mRNA, variation Smad7B, lacks "cag" (nt 2104-2106 in NM_008543).

Most preferably Smad7-Antisense Oligonucleotides of Human sequences (5'-3'-direction) are:

| | | |
|---|---|---|
| ctccggctgccccacccc | (SEQ ID NO: 16) | AF010193, nt 38-54, 5'UT |
| cgaacatgacctccgcac | (SEQ ID NO: 17) | AF010193, nt 243-250, 5'UT |
| atcgtttggtcctgaacat | (SEQ ID NO: 18) | AF010193, nt 296-314, cds |
| ccctcctcctcgtcctcg | (SEQ ID NO: 19) | AF010193, nt 358-375, cds |
| gtcgcccttctccccgcag | (SEQ ID NO: 20) | AF010193, nt 404-423, cds |
| gctgtccgtcgcccttc | (SEQ ID NO: 21) | AF010193, nt 413-430, cds |
| agcaccgagtgcgtgagc | (SEQ ID NO: 22) | AF010193, nt 577-594, cds |
| agttcgcagagtcggcta | (SEQ ID NO: 23) | AF010193, nt 889-906, cds |
| ggcaaaagccattcccct | (SEQ ID NO: 24) | AF010193, nt 1170-1187, cds |
| gccgattttgctccgcac | (SEQ ID NO: 25) | AF010193, nt 1232-1249, cds |
| ctgccccttcttccaaaa | (SEQ ID NO: 26) | AF010193, nt 1790-1807, 3'UT |
| actcacacacactcctga | (SEQ ID NO: 27) | AF010193, nt 1905-1928, 3'UT |
| tgcccaggtactgcctct | (SEQ ID NO: 28) | AF010193, nt 2076-2093, 3'UT |
| gagatccaggagcagatg | (SEQ ID NO: 29) | AF010193, nt 2310-2327, 3'UT |

Here, the most relevant human Smad7 Genbank entries are AF010193 (Smad7 mRNA, complete cds), XM_033746 (MADH7 mRNA, variation 1213:/allele="C"/allele="T") and XM_008803 (MADH7 mRNA, variation 1500:/allele="C"/allele="T")

Rat Smad7-Antisense Oligonucleotides (5'-3'-direction) which are preferred are:

| | | |
|---|---|---|
| cttcggctgccccacccg | (SEQ ID NO: 30) | NM_030858, nt 1164-1181, 5'UT |
| atcgtttggtcctgaacat | (SEQ ID NO: 31) | NM_030858, nt 1422-1440, cds |
| ccctcctcctcgtcctcg | (SEQ ID NO: 32) | NM_030858, nt 1484-1501, cds |
| gtcgcccttctccccgcag | (SEQ ID NO: 33) | NM_030858, nt 1530-1549, cds |
| gccgtccgtcgcccttc | (SEQ ID NO: 34) | NM_030858, nt 1539-1556, cds |
| agcaccgagtgcgtgagc | (SEQ ID NO: 35) | NM_030858, nt 1703-1720, cds |

-continued

| | | |
|---|---|---|
| agttcacagagtcgacta | (SEQ ID NO: 36) | NM_030858, nt 2015-2032, cds |
| ggcaaaagccattcccct | (SEQ ID NO: 37) | NM_030858, nt 2296-3013, cds |
| gccgatcttgctcctcac | (SEQ ID NO: 38) | NM_030858, nt 2358-2375, cds |

Here, the relevant rat Smad7 Genbank entry is NM_030858 (mRNA, complete cds).

Furthermore, as documented in the appended examples and explained herein, modified and/or mutated oligonucleotides are envisaged in accordance with this invention, an example of such a oligonucleotide (5'-3'-direction) is gtcgc-cccttctcccccgcag (SEQ ID NO: 39).

Preferably, the antisense molecules to be employed in accordance with the present invention are 100% complementary to the mRNA (coding and/or non-coding region) of Smad7 as shown herein; e.g. SEQ ID NO: 1, 3 or 5 or as shown in GenBank accession numbers NM_008543 (mouse), AF010193 (human), NM_030858 (rat). Yet, it is also envisaged that said antisense molecule comprises additional nucleotides, substituted nucleotides, nucleotide exchanges, nucleotide inversions or nucleotide deletions. However, as documented in the appended examples, functional antisense molecules to be employed in the present invention are preferably more than 85%, more preferably more than 90%, most preferably more than 95% complementary to the Smad7 mRNA (coding region and/or non-coding region). For example, most effective anti-Smad7 molecules/antisense molecules comprise nucleotides which are 100% complementary to the corresponding mRNA. Yet, as also shown in the appended examples, antisense molecules comprising, inter alia, one or two additional nucleotides are functional in context of the invention.

The invention also relates to a method for preventing, ameliorating and/or treating a disease of the central nervous system and/or of diseases related and/or caused by said disease in a subject comprising administering a specific inhibitor of Smad7 expression or function as defined herein above to a subject in need thereof. Preferably, said subject is a mammal, most preferably said mammal is a human.

A "patient" or "subject" for the purposes of the present invention includes both humans and other animals, particularly mammals, and other organisms. Thus, the methods are applicable to both human therapy and veterinary applications. In the preferred embodiment the patient is a mammal, and in the most preferred embodiment the patient is human.

In a most preferred embodiment of the invention, the disease of the CNS to be treated by the pharmaceutical composition comprising a herein defined anti-Smad7 inhibitor is an autoimmune disease of the CNS, trauma or is cerebral ischemic stroke. Preferably, said trauma is traumatic brain injury TBI) or traumatic spinal cord injury and said cerebral ischemic stroke is "focal cerebral ischemia". However, global cerebral ischemia, hypoxic-ischemic brain injury, CNS hypoxia and diseases or conditions related and/or caused by said diseases share pathogenetic features including upregulation of TGF-beta with focal cerebral ischemia and therefore are candidates for the treatment with Smad7 inhibitors. The appended examples illustrate the successful and inventive use of Smad7 inhibitors as defined herein in the treatment of these diseases/disorders. Preferably, said autoimmune disease is multiple sclerosis. Said multiple sclerosis may be selected from the group consisting of relapsing-remitting multiple sclerosis, secondary progressive multiple sclerosis, primary chronic progressive multiple sclerosis, neuromyelitis optica (Devic's syndrome), acute disseminated encephalomyelitis, fulminant multiple sclerosis (Marburg's variant), isolated autoimmune optic neuritis, isolated autoimmune transverse myelitis, Balo's concentric sclerosis. All of the aforementioned diseases are considered subtypes of MS or are CNS autoimmune diseases related to MS or common early stages of MS prior to clinical definite diagnosis of MS according to the art. Cerebral ischemic stroke and CNS trauma involve pathological mechanisms that are shared with MS and subtypes, e.g. leakage of the blood brain barrier, influx of immune cells, and microglial activation, leading to a inflammatory-mediated secondary damage to brain tissue which can be downregulated by application of antiinflammatory molecules like TGF-beta. Stroke, e.g. focal hypoxic-ischemic damage of the brain is characterized by a central necrotic tissue lesion and a surrounding "penumbra" which can be described as "tissue at risk". Neuronal cells within this zone are still prone to die for an extended period of time. TGF-beta expression was reported to be significantly increased in the penumbra (Slevin, Gunsilius, 2001), and interpreted as an indication of the amount of salvageable brain (Ali, 2001). The acute local inflammatory response following cerebral ischemia is thought to cause part of the perifocal brain injury. Adenoviral-mediated overexpression of TGF-beta 1 five days before MCA-occlusion resulted in inhibition of the chemokines MCP-1 and MIP1-alpha and a significantly reduced infarct volume (Pang, 2001). However, when administered after induction of cerebral ischemia via the contralateral carotid artery in a rabbit model of thromboembolic stroke TGF-beta did not have significant effect regarding infarct size or production of excitatory amino acid levels (Gross, 1994). Nevertheless, TGF-beta apparently has neuroprotective effects in vivo, as blockade of TGF-beta interaction with its receptor aggravated the volume of infarction in a rat model of stroke (Ruocco, 1999). Therefore it can be estimated that amplification of signaling via TGF-beta has a beneficial effect in stroke by saving the not lethally damaged surrounding cells and finally reducing the infarct volume. With regard to global brain ischemia the upregulation of TGF-beta1 gene expression in brain tissue extends from 6 hours to 21 days (Lehrmann, 1995). Maximum of TGF-beta1 gene induction was demonstrated to occur between 5 and 7 days after ischemia (Zhu, 2000). The local intraparenchymal injection of TGF-beta1 attenuated apoptosis and improved postischemic neurological outcome (Zhu, 2002). In transient global ischemia in rats, Henrich-Noack and colleagues were able to show significant protection of pyramidal CA1 cells by intrahippocampal injection of TGF-beta1 prior to ischemia. Several in vivo studies analyzed the effect of intraarterial or intracerebroventricular administration of TGF-beta1 before (Gross, 1993) or after induction of ischemia (Gross, 1994, McNeill, 1994) in a rabbit model of thromboembolic stroke or a rat model of severe hypoxic-ischemic brain injury, respectively. These studies showed that either treatment regimen was associated with a significant reduction of neuronal loss and infarct size. In transient global ischemia in rats, Henrich-Noack and colleagues were able to show significant protection of pyramidal CA1 cells by intrahippocampal injection of TGF-beta1 prior to ischemia (Henrich-Noack, 1996). Similar effects of increased lesion sizes after application of TGF-beta antagonists in animal models of excitotoxic damage to the brain suggest that approaches upregulating TFG-beta effects might be used to protect from acute excitotoxic injury occurring in traumatic CNS injury (Hailer, 2001). In some patients with acute traumatic brain injury an intracerebral production of TGF-beta peaking at the first day post trauma and possibly conferring a protection against secondary inflammation-induced brain damage was reported (Morganti-Kossmann, 1999).

As mentioned herein above, further diseases related and/or caused by diseases of the central nervous system may be treated by the use of Smad7 inhibitor, Smad7 antagonist or anti-Smad7 substances as defined herein. These diseases or disorders may be selected from the group consisting of diabetes, in particular type I diabetes mellitus. Type I diabetes mellitus is an organ-specific autoimmune disease and as such comparable to multiple sclerosis. In addition, recent studies have suggested that patients with type I diabetes display increased reactivity of peripheral blood T cells to central nervous system antigens while patients with multiple sclerosis show significant immune responses to pancreatic islet antigens (Winer, 2001a). This pattern of interrelated autoimmune T cell reactivity is also found in animal models of spontaneous insulin-dependent diabetes. In addition there are similarities in the T cell response to environmental antigens such as cow milk protein (Winer, 2001b).

It is also envisaged that the anti-Smad7, Smad7-inhibitor or Smad7 antagonists as defined herein are employed in the treatment or prevention of neurodegenerative disorders, like Alzheimeres disease or Parkinson's disease.

Most preferably, the pharmaceutical composition to be prepared in accordance with this invention and comprising an anti-Smad7 expression and/or function inhibitor(s) is to be administered by one or several of the following modes: Administration can be oral, intravenous, intraarterial, intratracheal, intranasal, subcutaneous, intramuscular, intracranial ( i.e. intraventricular) or intraspinal (intrathecal), epidermal or transdermal, pulmonary (e.g. inhalation or insufflation of aerosol or powder), by delivery to the oral or rectal mucosa as well as ophthalmic delivery.

It is, inter alia, envisaged that Smad7 inhibitors, like the antisense constructs/molecules or siRNAs described herein, are administered in combination with further compounds/medicaments. Said further compound/medicament or molecule may, e.g., induce an upmodulation of TGF-beta or may activate latent TGF-beta. Said further compound/medicament/molecule may also be an immunomodulator or an immunosuppressive drug. Such immunomodulators are known in the art and comprise, inter alia, (recombinant) human interferon-beta 1a, (recombinant) human interferon-beta 1b or glatiramer acetate and other drugs/compounds that modulate the activation, migration, effector function and/or survival of immune cells. Such compounds may be antibodies or antibody fragments directed against molecules expressed on cell surfaces (such as adhesion molecules, cytokine or chemokine receptors, or receptors for ligands contributing to immune cell activation or immune cell effector functions) or against circulating molecules such as cytokines, chemokines, or ligands for receptors mediating immune cell activation or immune cell effector functions. Such compounds may also comprise synthetic agonists or inhibitors for cytokine and chemokine receptors or other endogeneous molecules, such as adhesion molecules or intracellular transcription or activation modulatory molecules. Such compounds may also comprise molecules aimed at modulating antigen specific immune responses (e.g. altered peptide ligands, T-cell receptor vaccination, DNA vaccination, or other strategies to modify immune responses). The substances/drugs to be administered with anti-Smad7 compounds/Smad7 inhibitors described herein may compromise further substances that supress growth or activation of immune cells like azathioprine, mitoxantrone, cyclophosphamide, cyclosporine A, mycophenolate mofetile, rapamycine, minocycline or methotrexate. Other drugs/compounds envisaged of immune cells and/or the activation, migration, effector function and/or survival of immune cells. The immunosuppressive substances/drugs to be administered with the anti-Smad7 compounds/Smad7 inhibitors described herein may comprise azathioprine, mitoxantrone, cyclophosphamide, cyclosporine A, mycophenolate mofetile, cyclosporine A, rapamycine, minocycline or methotrexate.

Dosage and administration regimes for the Smad7-inhibitors may be established by the physician. For example, for antisense compounds, like antisense-nucleotides specific dosage regimes have been established. Such regimes comprise a dosage of 1 mg/kg up to 200 mg/m$^2$ and are, inter alia, described in Schreibner (2001), Gastroenterology 120, 1399-1345; Andrews (2001), J. Clin. Oncol. 19, 2189-2200; Blay (2000), Curr. Op. Mol. Ther. 2, 468-472; Cunnigham (2000), Clin. Cancer Res. 6, 1626-1631; Waters (2000), J. Clin. Oncol. 18, 1809-1811 or Yacyshyn (1998), Gastroenterology 114, 1133-1142. It is, for example, envisaged that the Smad7 inhibitors described herein, e.g. antisense compounds or RNAi and the like, be administered in single doses of 0.1 to 25 mg/kg/die (for example i.v. over 2 to 8 hours), as single or multiple doses every other day or by continuous infusion(s) of 0.5 to 10 mg/kg/die over 14 to 21 days with 7 day rest. It is of particular note that in certain clinical or medical indications it might be desirable to administer the Smad7-inhibitors as disclosed herein in a single dose. For example, in an acute traumatic incident (trauma of brain or spinal cord) or in an ischemic event in the brain (e.g. stroke) a single administration of the Smad7-inhibitors may suffice to ameliorate the condition of the affected patient, preferably human patient. In other disorders of the CNS, like immunological disorders (e.g. MS), a treatment regime of multiple administrations may be desired. Yet, further dosage regimes are envisaged and may easily be established by a physician.

The Figures show:

FIG. 1.

Preventive Smad7-as-ODN-treatment delays onset and alleviates clinical severity of EAE. Naive mice were injected with 30×10$^6$ PLP-specific LNC as described in Materials and Methods. In a preventive setting 100 μg Smad7-as-ODN (5 mg/kg/d) in PBS or an equal volume of PBS were injected i.p. daily from the day of transfer until the onset of clinical signs in the control group (day 8). The onset of disease was significantly delayed from day 14.29±1.10 (mean±SE) to day 27.43±4.28 (p=0.029; Table 1).

FIG. 2.

Smad7-as-ODN treatment effect is potentially long lasting and may be dose dependend. Naive mice were injected with 30×10$^6$ PLP-specific LNC as described in Materials and Methods. 100 μg of Smad7-as-ODN (5 mg/kg/d) in PBS or an equal volume of PBS were injected i.p. daily from the day of transfer for 3 weeks, every other day for the following 2 weeks and twice weekly for the remaining 5 weeks. The difference in median clinical scores between the experimental groups was statistically significant between days 15 and 26, on days 28, 40, 41, 50, 53, and between days 60 and 64 (p≦0.05). At day 40 the EAE-prevalence in the treatment group was 0/6, suggesting a continuous treatment of 5 mg/kg three times weekly to be sufficient for disease suppression.

FIG. 3.

Smad7-as2-ODN-treatment delays onset and alleviates clinical course of EAE. Naive mice were injected with 5×10$^6$ PLP-specific LNC as described in Materials and Methods. 100 µg antisense oligonucleotides (5 mg/kg/d) in PBS or an equal volume of PBS were injected i.p. daily from the day of transfer until the end of experiment. The onset of disease was delayed in the Smad7-as2-ODN group from day 10.4±1.66 (mean+SE) to day 15.8±3.69 (Table 3). Smad7-as2-ODN had a more powerful effect than Smad7-as-ODN, whereas Smad7-mut4-as-ODN (an antisense-construct which is not capable of specifically hybridizing to the relevant Smad7 encoding nucleic acid molecule) deteriorated the clinical course.

FIG. 4.

Smad7-as-ODN suppresses the clinical severity of EAE in a therapeutic manner. Naive mice were injected with 30×10$^6$ PLP-specific LNC as described in Materials and Methods. Mice were divided in treatment groups of equal EAE-incidence and cumulative score at the peak of disease (day 12). 100 µg of Smad7-as-ODN (5 mg/kg/d) in PBS or an equal volume of PBS were injected i.p. daily from day 12 to day 28 and subsequently every other day from day 29 to day 45. The difference in mean EAE-score between the two groups was statistically significant between days 18 and 20 and between days 26 and 32 ($p \leq 0.05$).

FIG. 5.

CNS autoimmune disease is preventable by exposing autoreactive LNC to Smad7-as treatment in vitro. LNC were obtained from PLP-immunized mice as described in Materials and Methods and restimulated for 96 hours with 10 µg/ml PLP and 20 µM Smad7-as-ODN or PBS, respectively. The proliferation was reduced by approximately 30% as measured by $^3$H-cytidine intake (not shown). 5×10$^6$ viable LNC were injected in naive recipient mice i.p. and clinical score was examined for 20 days until the peak of disease in the control group was clearly reached. Mice receiving LNC treated with Smad7-as-ODN did not develop clinical signs of EAE. This suggests that Smad7-as-ODN-treatment can prevent the reactivation of primed autoreactive T cells and block their disease-inducing properties.

FIG. 6.

Smad7-as2-ODN suppresses the proliferation of activated LNC in vitro. PLP-specific LNC were obtained and cultured as described in Materials and Methods over 96 hours and increasing concentrations of Smad7-as2-ODN or Smad7-mut4-as-ODN, respectively. Wells without antisense oligonucleotide or PLP served as controls. The proliferation of LNC is shown as the mean±standard error of quadruplicate cultures. A, Smad7-as2-ODN reduced the proliferation of PLP-restimulated LNC statistically highly significant at concentrations from 20 µM (* $p<0.05$, ** $p<0.005$). B, Smad7-mut4-as-ODN had no effect on LNC-proliferation.

FIG. 7.

Smad7-as-ODN diminishes the proliferation of activated LNC in vitro. PLP-specific LNC were obtained and cultured as described in Materials and Methods. LNC were restimulated with 10 µg/ml PLP or 0.2 µg/ml Con A and various concentrations of Smad7-as-ODN over 96 hours. Wells without antisense oligonucleotide or PLP served as controls. The proliferation of LNC is shown as the mean±standard error of quadruplicate cultures. The effect of Smad7-as-ODN was statistically significant at a concentration of 1 µM ($p<0.05$).

FIG. 8.

Smad7-as-ODN are not toxic against activated LNC. PLP-specific LNC were obtained and cultured as described in Materials and Methods. LNC were restimulated with 10 µg/ml PLP and increasing concentrations of Smad7-as-ODN (initially 8×10$^5$ LNC) or Smad7-as2-ODN (initially 4×10$^5$ LNC) over 96 hours, respectively. Wells without antisense oligonucleotide served as controls. The viability of LNC is shown as the mean±standard error of triplicate cultures. Cell viability was measured by trypan blue exclusion.

FIG. 9.

Absence of toxicity of Smad7-as2-ODN against activated LNC. PLP-specific LNC were obtained and cultured as described in Materials and Methods. 4×10$^5$ LNC were restimulated with 10 µg/ml PLP and increasing concentrations of Smad7-as2-ODN over 96 hours. Wells without antisense oligonucleotide served as controls. Cell viability was measured by propidium iodide staining in Flow-cytometric analysis (2×10$^4$ LNC each). The viability of LNC is shown as the mean±standard error of triplicate cultures.

FIG. 10.

Figure 11:
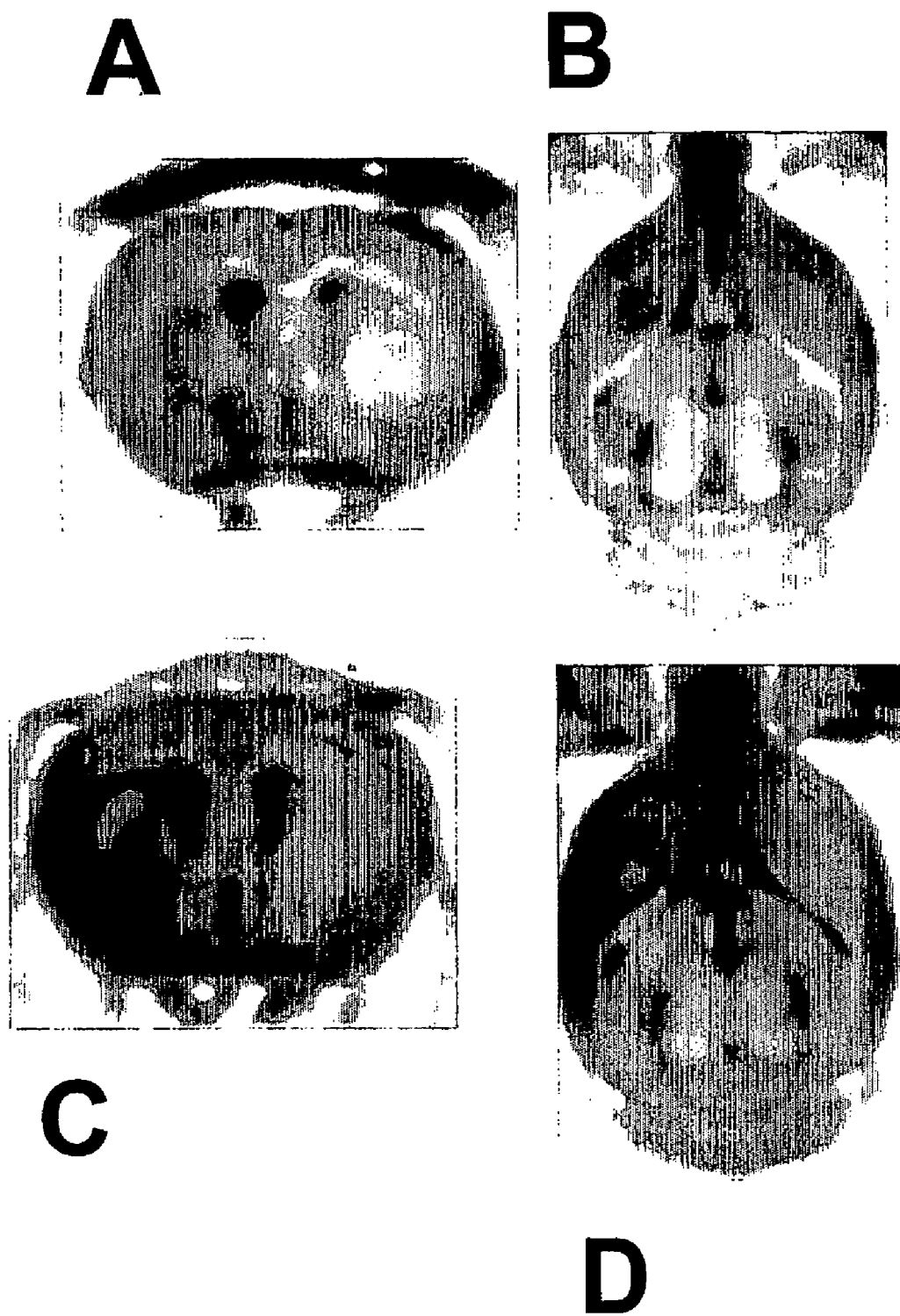
Figure 12:
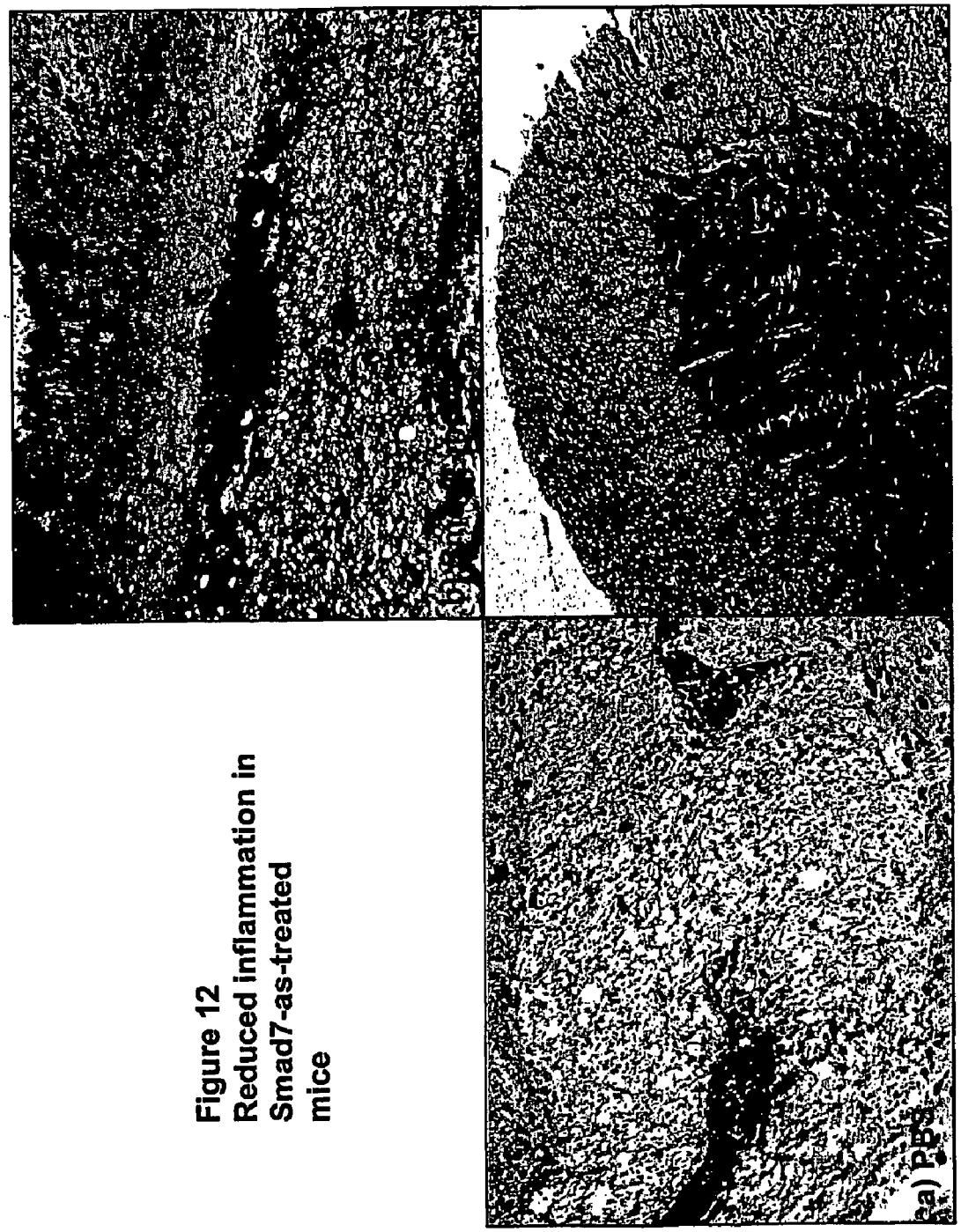

Smad7-as-ODN treatment in vivo inhibits the priming of autoreactive T cells. Mice were immunized with 200 µg PLP s.c. as described above. On days 7, 8, and 9 after immunization the mice were treated i.p. with either 100 µg Smad7-as-ODN or Smad7-as2-ODN in PBS, 100 µg of a control random PTO-Oligonucleotide 5'-atg gac aat atg tct a-3' (SEQ ID NO: 87) in PBS, or an equal volume of PBS. Lymph nodes of treated mice were harvested on day 10 and proliferation from LNC cultures was determined as described above. Cells from PBS-treated mice show a strong antigen-specific proliferation in contrast to the blunted proliferative response of cells from mice treated with antisense molecules (FIG. 11). The cells from the mice treated with random-ODN proliferated in culture even without adding peptide antigen.

FIG. 11.

In-vivo MRI 7 days after stroke (90 minutes occlusion of the right middle cerebral artery) in two individual animals treated either with 400 pmol Smad7-as2-ODN antisense oligonucleotides per kg body weight (FIG. 11a,b) or with the same amount of the respective sense oligonucleotides (FIG. 11c,d; treatment control). Inversion recovery MRI demonstrate a distinct reduction of infarct volume, especially by preservation of the cerebral cortex, in the Smad7-antisense treated animal. Similar MRI findings were obtained in these animals four weeks after ischemia.

FIG. 12

Smad7-as2-ODN-treatment reduces CNS inflammation. Representative mice from the experiment depicted in FIG. 3 were sacrificed on day 49; paraffin sections of the brain and spinal cord were prepared, stained for H.-E. and evaluated as described in Materials and Methods. (a) PBS-treated animal, EAE-grade 2: axial section of the lumbar part of the spinal cord (obj.-magnification 20×). (b) Smad7-mut4-as-ODN-treated animal, EAE-grade 2.5: longitudinal section of the lower thoracic spinal cord (obj.-magnification 10×). (c) Smad7-as2-ODN-treated animal, EAE-grade 0: axial section of the lumbar spinal cord (obj.-magnification: 5×). In (a) and (b) EAE-typical perivascular infiltrates mainly consisting of lymphocytes and monocytes can be seen; in (c) no inflammation is seen.

FIG. 13

No organ toxicity is detected by histopathological evaluation of Smad7-as2-ODN-treated mice: Selected mice from the experiment depicted in FIG. 3 were sacrificed on day 49; paraffin sections of several organs were prepared, stained and evaluated as described in Materials and Methods. The figure shows representative sections of organs susceptible to TGF-beta-induced toxicity from a Smad7-as2-ODN-treated animal; liver (H.-E., obj.-magnification 40×), spleen (H.-E. (obj.-magnification 10×) and kidney (Masson-Goldner, (obj.-magnification 20×). In particular, no significant increase in connective tissue production was detected. In the kidney, a dilatation of the proximal renal tubules and a widening of the glomerular capsular spaces was observed in mice from all treatment groups and represents a perfusion artefact. In the spleen prominent multinucleated macrophages as typical for EAE-animals were seen in all mice irrespective of treatment. In addition to the organs shown here, skin, lymph node, colon, heart and lung were examined.

FIG. 14

Smad7-as2-ODN diminishes the proliferation of mitogenically activated spleen cells.

Spleen cells were obtained from non-immunized mice and cultured as described in Materials and Methods using 2 µg/ml ConA to polyclonally activate T cells and various concentrations of Smad7-as2-ODN or Smad7-mut4-as-ODN over 96 hours. Wells without antisense-ODN or ConA served as controls. The proliferation of spleen cells is shown as the mean±standard error of quadruplicate cultures.

FIG. 15

Smad7-as2-ODN suppress proliferation of splenic CD4$^+$ and CD8$^+$ T cells. 10 days after immunization with 200 µg of PLP$_{139-151}$ spleens were dissected and lymphocytes isolated by Ficoll-Paque Plus. CD4$^+$ and CD8$^+$ T cells were sorted on positive MS-columns using magnetic microbeads coupled to monoclonal antibodies for CD4 or CD8, respectively. The resulting enriched T cell (FIG. 15a), CD4$^+$ (FIG. 15b) and CD8$^+$ T cell (FIG. 15c) populations were stimulated by plate-bound anti-mouse-CD3-antibodies for 72 hours in the presence of varying concentrations of Smad7-as2-ODN or Smad7-mut4-as-ODN as described in Materials and Methods. Uncoated wells or wells without antisense PTO-ODN, respectively, served as controls. Results are given as arithmetic means±standard error from cultures set up at least in triplicate. A strong suppressive effect of Smad7-as2-ODN on proliferation is seen at concentrations of 10 µM (enriched T cells) or 20 µM (CD4$^+$ and CD8$^+$ T cell subpopulations was pronounced at concentrations of 20 µM.

FIG. 16

Effects of Smad7 antisense-treatment on T cell proliferation in vitro do not predict efficacy in vivo. PLP-specific LNC were obtained and cultured as described in Materials and Methods over 96 hours and increasing concentrations of Smad7-as2-ODN, Smad7-as3-ODN and Smad7-as4-ODN, respectively. Wells without antisense ODN or PLP served as controls. The proliferation of LNC is shown as the mean±standard error of at least triplicate cultures. All ODN dose-dependently suppressed proliferation (FIG. 16a). Smad7-as2-ODN and Smad7-as3-ODN were then compared with respect to treatment effect (FIG. 16b): Naïve mice were injected with 5×10$^6$ PLP-specific LNC as described in Materials and Methods. 100 µg (5 mg/kg/d) of Smad7-as2-ODN or Smad7-as3-ODN or Smad7-mut4-as-ODN in PBS or an equal volume of PBS were injected daily from the day of transfer. Smad7-as2-ODN has a stronger beneficial effect on the clinical course than Smad7-as3-ODN while Smad7-mut4-as-ODN rather worsens EAE-signs (FIG. 16b). In the group treated with Smad7-mut4-as three mice died at early timepoints during the experiment. By convention they were given a grade 5 in the disease severity score until the end of the experiment.

FIG. 17

Smad7-as2-ODN-treatment in vivo inhibits antigenic priming responses. Mice immunized with PLP peptide as described in Materials and Methods were treated with 100 µg (5 mg/kg) of Smad7-as2 or Smad7-mut4-as-ODN or an equal amount of PBS daily i.p. from day 6 to day 9 after immunization. LNC from these groups of mice were restimulated with antigen for 96 hours and used for proliferation assays as described in Materials and Methods. LNC from mice treated with Smad7-as2-ODN during antigenic priming proliferated less vigorously upon specific peptide restimulation as compared to LNC from mice treated with Smad7-mut4-as-ODN. This suggests that a blunted primary immune response is the cause for the reduced LNC encephalitogenicity observed in the experiments of FIG. 18.

FIG. 18

Smad7-as2-ODN-treatment in vivo suppresses the induction of, autoreactive encephalitogenic T cells. Mice immunized with PLP peptide as described in Materials and Methods were treated with 100 µg (5 mg/kg) of Smad7-as2 or Smad7-mut4-as-ODN or an equal amount of PBS daily i.p. from day 6 to day 9 after immunization. LNC from these groups of mice were subsequently restimulated with antigen for 96 hours and used for adoptive transfer (5×10$^8$ LNC per recipient mouse) as described in Materials and Methods. Two separate experiments are shown. LNC from mice treated with Smad7-as2-ODN either induced a highly attenuated clinical course (FIG. 18a, compare number of deaths) or did not induce EAE at all (FIG. 18b).

FIG. 19

Preventive treatment with Smad7-specific short interfering RNAs (siRNAs) alleviates the clinical signs of at-EAE. 5×10$^6$ PLP$_{139-151}$-specific LNC, generated as described in Materials and Methods, were adoptively transferred in naïve mice. Recipient mice were treated twice daily with 20 pmol of RNAi1 or RNAi2 or an equal volume of PBS i.p. Mice treated with RNAi1 and RNAi2 show an ameliorated acute disease course as compared to PBS-treated mice.

FIG. 20

Preventive Smad7 antisense-treatment ameliorates the clinical course in a second disease model relevant for multiple sclerosis: MOG-induced EAE in rats. Female DA rats were immunized with 65 µg of recombinant MOG$_{1-125}$ in CFA i.c. as described in Materials and Methods. Rats were treated i.p. with 5 mg/kg Smad7-as2-ODN or Smad7-mut4-as-ODN or an equal amount of PBS (250 µl) daily starting on day -2 prior to immunization. The development of clinical signs is delayed in rats treated with Smad7-as2-ODN as compared to rats treated with PBS.

FIG. 21

Local Smad7-as2-ODN-treatment reduces infarct volume as measured by MR volumetry after transient occlusion of the middle cerebral artery in rat. MR infarct volumetry was performed to measure infarct volumes in rats. Occlusion of the middle cerebral artery was performed as described in Materials and Methods. Infusion of the ODN into the internal carotid artery was initiated beginning with reperfusion after 90 min ischemia; rats were treated with 400 pmol Smad7-as2-ODN per kg body weight (n=8) or Smad7-sense-ODN (n=8) as described in Materials and Methods. In vivo infarct-volumetry by MRI was performed 7 days and 3 months after surgery as described in Materials and Methods. At both time-points the infarct volume in the rats treated with Smad7-as2-ODN as compared to Smad7-sense ODN was significantly reduced (7 days: 1.18±0.26 cm$^3$ vs. 0.49±0.25 cm$^3$ ($p<0.001$); 3 months: 1.36±0.42 cm$^3$ vs. 0.60±0.28 cm$^3$, ($p<0.001$ Student t-test)).

FIG. 22

Infarct size as visualized by MRI and by histopathology is considerably reduced by local Smad7-as2-ODN-treatment after transient occlusion of the middle cerebral artery in rat. MR imaging (inversed recovery sequences; coronal and axial orientation) 7 days and 3 months after ischemia and postmortem histology including immunostaining for GFAP (glial fibrillary acid protein) were performed as described in Materials and Methods in two individual rats either treated with Smad7-sense ODN (a,b,e,f,i,j) or Smad7-as ODN (c,d,g,h,k,l), respectively. Parts of this figure correspond to FIG. 11. (FIG. 22a=11c; 22b=11d; 22c=11a; 22d=11b).

FIG. 23

SEQ ID NO:1, human Smad7 mRNA

Target sequences of human Smad7-Antisense Oligonucleotides SEQ ID No: 16-29 are underlined, one partially overlapping sequence, corresponding to SEQ ID NO: 21, is shown in italics.

FIG. 24:

SEQ ID NO:2, human Smad7 nucleotide sequence
CDS 296 . . . 1576
/gene="SMAD7"
/codon_start=1
/product="MAD-related gene SMAD7"

FIG. 25:

SEQ ID NO:3, Mouse Smad7 mRNA

Target sequences of mouse Smad7-Antisense Oligonucleotides SEQ ID No: 7-15 are underlined, one partially overlapping sequence, corresponding to SEQ ID NO: 11, is shown in italics.

FIG. 26:

SEQ ID NO:4, mouse Smad7 Amino Acid sequence
CDS 1437 . . . 2717
/gene="Madh7"
/codon_start=1

FIG. 27

SEQ ID NO:5, Rat Smad7 mRNA

Target sequences of rat Smad7-Antisense Oligonucleotides SEQ ID No: 30-38 are underlined, one partially overlapping sequence, corresponding to SEQ ID NO: 34, is shown in italics.

FIG. 28

SEQ ID NO:6, rat Smad7 Amino Acid sequence
CDS 1422 . . . 2702
/gene="Madh7"
/codon_start=1

FIG. 29

Treatment with Smad7-as2-ODN, but not Smad7-mut4-as-ODN, suppresses TGFbeta induced Smad7 mRNA expression in Jurkat T-cells. Jurkat T-Cells were treated with Smad7-as2-ODN, Smad7-mut4-AS-ODN or PBS for 4 hours and then incubated with or without TGFbeta for 30 minutes. Normalized relative amounts of Smad7 mRNA expression were estimated as described in Materials and Methods (Example 19).

The Examples illustrate the invention.

EXAMPLE 1

Methological Part of the Further Examples

Materials and Methods

Animals

Female SJL/J mice were obtained from Harlan Winkelmann (Borchen, Germany) and from Charles River (Sulzfeld, Germany). Mice were 8-20 weeks of age when experiments were started. All procedures were conducted according to protocols approved by the commission of animal protection at the University of Regensburg. Mice were housed in normal cages with free access to food and water; paralyzed mice were afforded easier access to food and water.

Antigens

A serine-substituted peptide 139-151 from proteolipid protein (PLP), $PLP_{139-151}$, was prepared by continuous flow solid phase synthesis according to the sequence for murine PLP (HSLGKVVLGHPDKF SEQ ID NO: 40) by the Institute of Microbiology, University of Regensburg, Germany. Amino acid composition of the peptide was verified by amino acid analysis and purity was confirmed by mass spectroscopy.

Induction of Adoptive Transfer EAE

Each recipient mouse was injected i.v. with 5 to $30 \times 10^6$ activated $PLP_{139-151}$-specific lymph node cells (LNC) as indicated for the individual experiments. Short term $PLP_{139-151}$-specific T-cell lines were generated by immunizing SJL/J mice s.c. at four sites across the flank with 200 μg of $PLP_{139-151}$, emusified 1:1 with CFA containing 800 μg of Mycobacterium tuberculosis H37Ra (Difco Laboratories, Detroit, Mich., USA) in a total volume of 200 μl/animal. After ten to eleven days lymph node cells (LNC) derived from draining axillary and inguinal lymph nodes were harvested and cultured with 10 μg/ml of $PLP_{139-151}$ in 24 well plates. The culture medium was based on RPMI 1640 (Life Technologies Inc.), supplemented with 10% heat-inactivated fetal calf serum (Biochrom KG, Berlin, Germany), 2 mM L-glutamine, 100 U/ml penicillin, 100 μg/ml streptomycin, $5 \times 10^{-5}$ M 2-ME, 1 mM sodium-pyruvate, 12.5 mM HEPES, and 1% non-essential amino acids (all Life Technologies Inc.) according to a protocol previously described [Rajan, 2000]. After 96 hours the LNC were harvested and injected into naive SJL/J recipients.

Clinical Evaluation

Mice were examined daily for signs of disease and graded on a scale of increasing severity from 0 to 5 as follows: 0 no signs; 0.5 partial tail weakness; 1 limp tail or slight slowing of righting from supine position; 1.5 limp tail and slight slowing of righting; 2 partial hindlimb weakness or marked slowing of righting; 2.5 dragging of hindlimb(s) without complete paralysis; 3 complete paralysis of at least one hindlimb; 3.5 hindlimb paralysis and slight weakness of forelimbs; 4 severe forelimb weakness; 5 moribund or dead. Mice reaching a score of 5 were sacrificed. A relapse was defined as a sustained increase of at least one full point for 2 or more days after the animal had improved previously at least one point and had stabilized for at least 2 days. The day of onset of clinical signs, the mean maximal score in each treatment group averaging the maximal score each animal reached at any time and the cumulative scores of all animals of each treatment group over defined periods of time were determined as measurements of disease severity. The number of relapses in a group divided by the number of the mice of that group was determined as the relapse rate.

Antisense PTO-Oligonucleotides and Treatment

The following single-stranded Smad7-antisense phosphorothioate (PTO)-Oligonucleotides (ODN) derived from human Smad-7-mRNA, GenBank AF010193 starting at position 404 from the mRNA-5'end were used: Smad-7-as-ODN, 5'-gtc gcc cct tct ccc ccg cag-3' (SEQ ID NO: 39), Smad7-antisense2 ODN 5'-gtc gcc, cct tct ccc cgc ag-3' (SEQ ID NO: 20), and the control Smad7-mut4-antisense ODN 5'-gtc gca ccg tct cac ag cag-3' (SEQ ID NO: 41) were synthesized by MWG-Biotech (Ebersberg, Germany) and provided in lyophilized form. PTO-ODN were HPSF®-purified. The amino acid composition and purity were confirmed by MALDI-TOF (Matrix Assisted Laser Desorption Ionization—Time of Flight)-Mass spectrometry. For the experiments described, the PTO-Oligonucleotides were dissolved in PBS at 0.4 µg/µl and adjusted to neutral pH. In treatment experiments 100 µg Smad7-antisense PTO-Oligonucleotides were injected i.p. daily (5 mg/kg/d), every other day or twice per week as indicated in the experiments. Distribution to treatment groups was performed by randomization. Mice injected with equal amounts of PBS or Smad7-mut4-antisense PTO-Oligonucleotide served as controls.

Transfer of in Vitro PTO-Oligonucleotide-Treated LNC

Mice were immunized with 200 µg PLP s.c. as described above. On day 10 lymph nodes were harvested and LNC cultured with 20 µM of Smad7-antisense PTO-Oligonucleotide and 10 µg/ml PLP as indicated above. After 96 hours the LNC were harvested and injected into naive SJL/J recipients.

In Vitro T-Cell Proliferation Assays

Spleen and draining lymph nodes cells were dissected from animals immunized with 200 µg of $PLP_{139-151}$ emusified in 200 µl CFA containing 250 µg Mycobacterium tuberculosis H37Ra 10-11 days previously. LNC were cultured in 96-well plates (Corning-Costar, Cambridge, Mass., USA) at $4 \times 10^5$ viable cells/well in a total volume of 200 µl RPMI 1640-based medium, as described above. Cells were cultured at 37° C. in 100% humidity and 5% $CO_2$ in the presence or absence of $PLP_{139-151}$ at a concentration of 10 µg/ml. Concanavalin A (Sigma Chemical Co.) was used at a concentration of 0.2-0.5 µg/ml. To determine the effect of the antisense PTO-Oligonucleotides, varying concentrations were added at a fixed antigenic concentration. Wells without antisense PTO-Oligonucleotides or antigenic peptide, respectively, were used as controls. LNC were pulsed with 1 µCi of $^3$H-thymidine (NEN Life Science Products, Boston, Mass., USA) after 72 hours, harvested at 96 hours, and $^3$H-thymidine uptake was detected using a Packard Topcount microplate scintillation counter (Packard instrument Co., Meriden, Conn., USA). Results are given as arithmetic means±standard error from cultures set up at least in triplicate.

Priming Studies

Mice were immunized with 200 µg PLP s.c. as described above. On days 7, 8, and 9 after immunization the mice were treated i.p. with either 100 µg Smad7-as-ODN or Smad7-as2-ODN in PBS, 100 µg of a control random PTO-Oligonucleotide 5'-atg gac aat atg tct a-3' (SEQ ID NO: 42) in PBS, or an equal~volume of PBS. Lymph nodes of treated mice were harvested on day 10 and proliferation from LNC cultures was determined as described above.

Toxicity Assays and Flow-Cytometric Analysis $PLP_{139-151}$-primed LNC were derived as described above and cultured with or without 10 µg/ml PLP-peptide in 96-well microtiter plates at 4 or $8 \times 10^5$ viable cells/well in 200 µl RPMI 1640 medium, as described above. Smad7-antisense PTO-Oligonucleotides were added in increasing concentrations. After 96 hours the viability of cells was measured both by trypan blue exclusion and by flow-cytometry using propidium iodide ($10^4$ cells/sample) respectively. Data collection and analysis were performed on a FACSCalibur flow cytometer (Becton Dickinson, Franklin Lakes, N.J., USA). Results are given as arithmetic means±standard error from cultures set up at least in triplicate.

Histology

Selected mice were killed with $CO_2$. Brain, spinal cord, lymph node, spleen, liver, kidney, colon, heart, lung and skin tissues were fixed in PFA 4%. Paraffin sections (4-6 µm) were made and stained with hematoxylin-eosine, luxol fast blue, and by the Bielschofsky and Masson-Goldner stainings, according to standard protocols. At least 2 coronal sections from three rostro-caudal brain-levels and at least 2 longitudinal and coronal sections from cervical, thoracic and lumbosacral levels of the spinal cord were evaluated in a blinded fashion. To screen for treatment toxicity at least 2 coronal sections from all other tissues were evaluated in in a blinded fashion by an experienced veterinarian.

Statistical Analysis

Differences in clinical scores of mice and cellular proliferation between groups were analyzed by Student's t test for unpaired samples. P values less than 0.05 were considered significant. For the plots mean value and standard error of the mean (SE) were calculated.

EXAMPLE 2

Preventive Smad7 Antisense-Treatment Delays Onset and Alleviates Clinical Course in at-EAE Adoptive-transfer EAE was induced in SJL mice by injection of activated $PLP_{139-151}$-specific LNC. Clinical disease started after 8-15 days, followed by partial recovery and one or more relapses (FIG. 1-4). In three consecutive experiments the effect of Smad7-as PTO-Oligonucleotides (Smad7-as-ODN) in vivo on the development of at-EAE was tested. Following LNC-transfer, mice were initially treated with 100 µg Smad7-as-ODN daily from day 0 (5 mg/kg/d) until the onset of clinical signs in the control group each (FIG. 1). Interestingly, the onset of disease was delayed by almost two weeks (Table 1). Subsequently, although there was no difference in EAE-incidence, maximal score per animal and relapse rate, the clinical course was mitigated, as documented by the cumulative disease scores, in particular during the chronic stage of EAE (days 61-90, Table 1, FIG. 1).

TABLE 1

| | Smad7-as | PBS |
|---|---|---|
| group size | n = 7 | n = 7 |
| EAE-incidence | 7/7 | 7/7 |
| EAE-prevalence (day 16) | 1/7 | 6/7 |
| EAE-prevalence (day 43) | 5/7 | 7/7 |
| EAE-prevalence (day 90) | 1/7 | 4/7 |
| day of onset (mean ± SE) | 27.43 ± 4.28 | 14.29 ± 1.10 |
| max. score (mean ± SE) | 2.86 ± 0.24 | 3.0 ± 0.59 |
| cumulative score (d 1-30) | 101.5 | 209 |
| cumulative score (d 31-60) | 220 | 307.5 |
| cumulative score (d 61-90) | 103.5 | 300.5 |
| relapse rate (mean ± SE) | 0.71 ± 0.33 | 0.57 ± 0.19 |
| relapse (number/animals) | 5/3 | 4/4 |

Effects of preventive Smad7-as-ODN treatment on clinical course of EAE (I). Groups of seven mice were treated with 100 µg Smad7-as-ODN (5 mg/kg/d) in PBS or an equal volume of PBS i.p. daily from the day of transfer until the onset of clinical signs in the control group. The clinical course was mitigated by Smad7-as-ODN, as indicated by the EAE-score (see FIG. 1), the cumulative disease scores and the EAE-prevalence on days 16, 43 and 90. There was no difference in EAE-incidence, mean maximal score and relapse rate.

Figure 2:
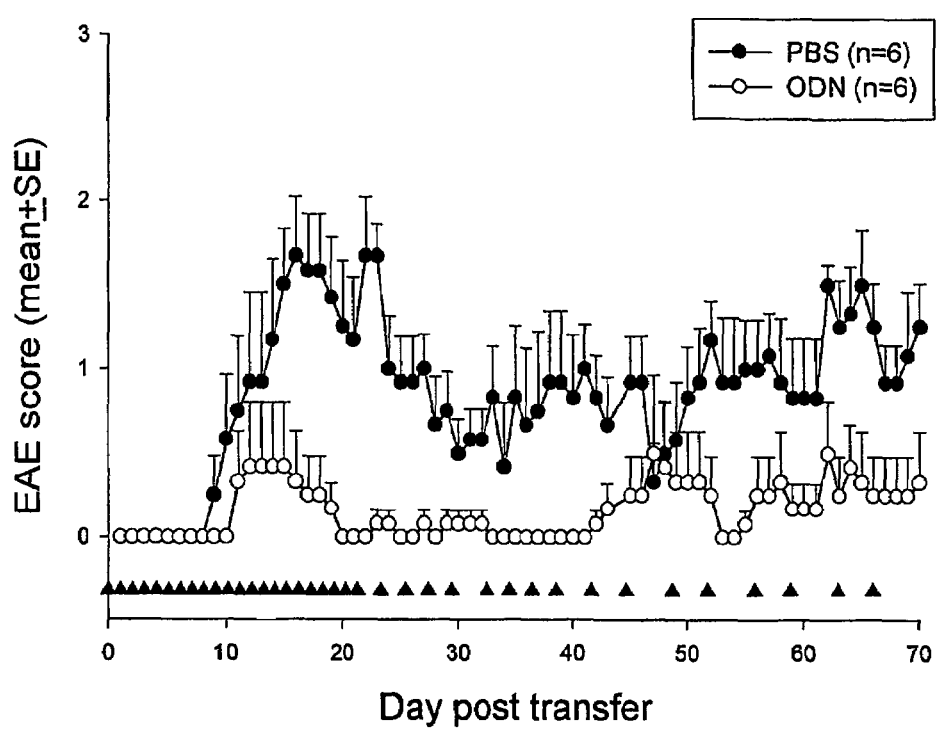

Initiating treatment at the day of transfer but extending the treatment period across the chronic disease stage as indicated in FIG. 2 revealed that the treatment effect is potentially long lasting and may be dependent on the dose or the frequency of application, respectively (FIG. 2, Table 2). Only when the administrations were tapered from initially daily to ultimately twice weekly for the last 6 weeks of observation there appeared to be a slight increase in disease activity (FIG. 2) with the initially diseased mouse having 2 relapses and another one a first exacerbation. Altogether a remarkable reduction in EAE-incidence, mean maximal score, absolute number of relapses (2 vs. 10) and relapse rate (0.33±0.30 vs. 1.67±0.30) was observed (Table 2).

TABLE 2

|  | Smad7-as | PBS |
| --- | --- | --- |
| group size | n = 6 | n = 6 |
| EAE-incidence | 2/6 | 6/6 |
| EAE-prevalence (day 14) | 1/6 | 5/6 |
| EAE-prevalence (day 35) | 0/6 | 2/6 |
| EAE-prevalence (day 60) | 2/6 | 6/6 |
| max. score (mean ± SE) | 0.67 ± 0.45 | 2.42 ± 0.14 |
| relapse rate (mean ± SE) | 0.33 ± 0.30 | 1.67 ± 0.30 |
| relapse (number/animals) | 2/1 | 10/6 |

Effects of preventive Smad7-as-ODN treatment on clinical course of EAE (II). Groups of six mice were treated with 100 μg Smad7-as-ODN (5 mg/kg/d) or PBS daily and then tapered to ultimately twice weekly as indicated in FIG. 2. Significant differences between groups were noted for mean maximal score (p=0.015) and relapse rate (p=0.018).

This experiment suggested a treatment regimen of 5 mg/kg three times weekly to be sufficient to obtain long-lasting suppression of clinical signs.

Figure 3:
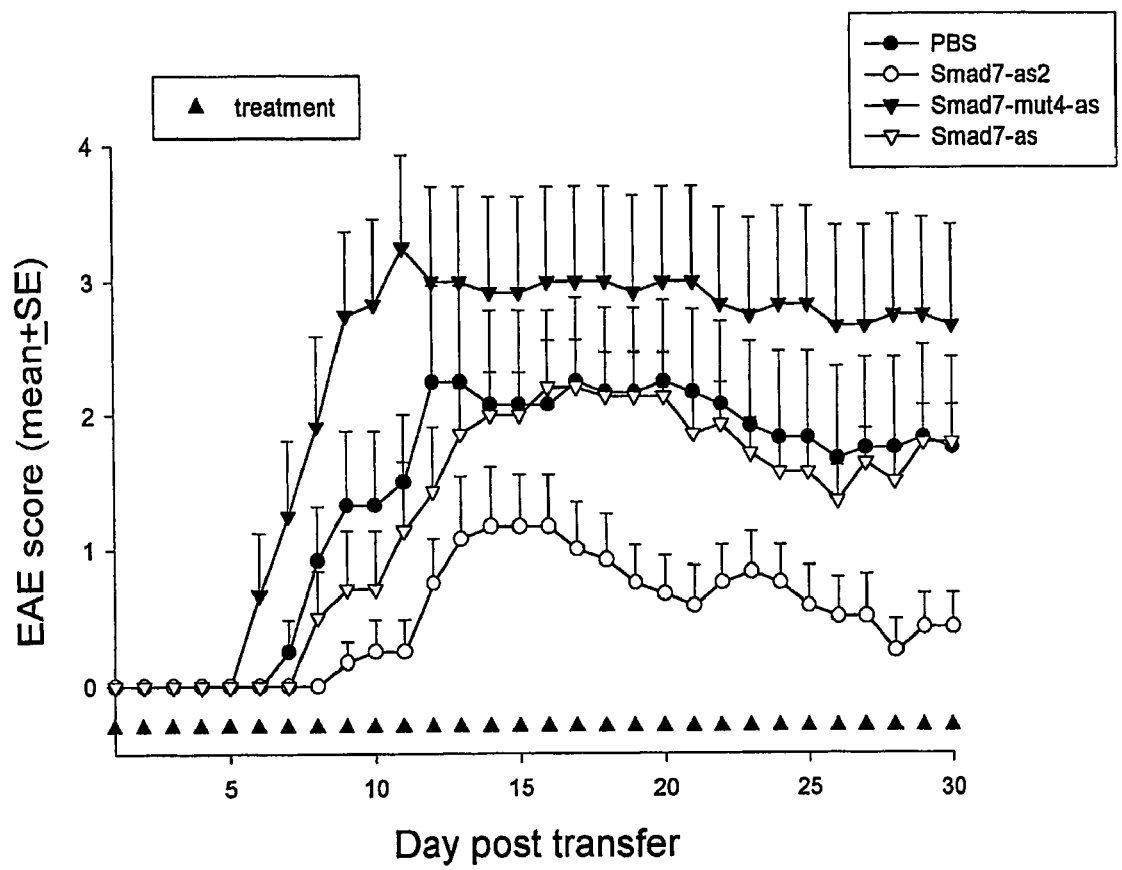

While Smad7-as-ODN contained an extra cytidine between position 124 and 125 of human Smad7-mRNA, the 20mer Smad7-as2-ODN lacks this cytidine. Treatment with the fully complementary Smad7-as2-ODN molecule appeared to be much more effective in later time points compared to Smad7-as-ODN. However, the antisense molecule comprising an additional nucleotide still appeared to be a valuable reagent during earlier time points; see FIG. 3. Yet, the documented Smad7-as2-ODN proved to have a more powerful treatment effect with regard to EAE-incidence, day of onset and mean maximal score than vehicle or Smad7-as-ODN (Table 3). Yet, appended Table 3 clearly documents the powerful effect of mutated as well as "wildtype" antisense molecules. The control PTO-Oligonucleotide Smad7-mut4-as, which is altered in 4 nucleotides compared to Smad7-as2-ODN did not have a protective effect on the development of acute disease (FIG. 3). The administration of 100 μg Smad7-mut4-as daily rather resulted in an earlier, more severe and prolonged first exacerbation compared to the groups receiving Smad7-as2-ODN, Smad7-as-ODN or PBS (Table 3).

Effects of preventive Smad7-as-ODN treatment on clinical course of EAE (III). Groups of six to seven mice were treated with 100 μg Smad7-as-ODN, Smad7-as2-ODN, the mutated control Smad7-mut4-as-ODN (5 mg/kg/d each) or PBS daily from the day of transfer as shown in FIG. 3. Mean maximal score and EAE-prevalence on days 12 and 30 were remarkably reduced in the Smad7-as2-ODN group. Smad7-as-ODN treatment resulted in a slightly reduced mean maximal score with no EAE-related deaths occurring.

Histology

Brain and spinal cord of representative mice of the experiment depicted in FIG. 3 were evaluated histologically. PBS-treated mice showed typical monocuclar infiltrates in spinal cord and brain. The extent of CNS inflammation correlated with the clinical scores with high scores associated with many dense infiltrates extending from submeningeally deep into the white matter. Smad7-as2-ODN treated mice showed less CNS inflammation than mice treated with Smad7-mut4-as-ODN or PBS.

Smad7as-Treatment at Peak of Disease Alleviates Clinical Course in at-EAE

Figure 4:
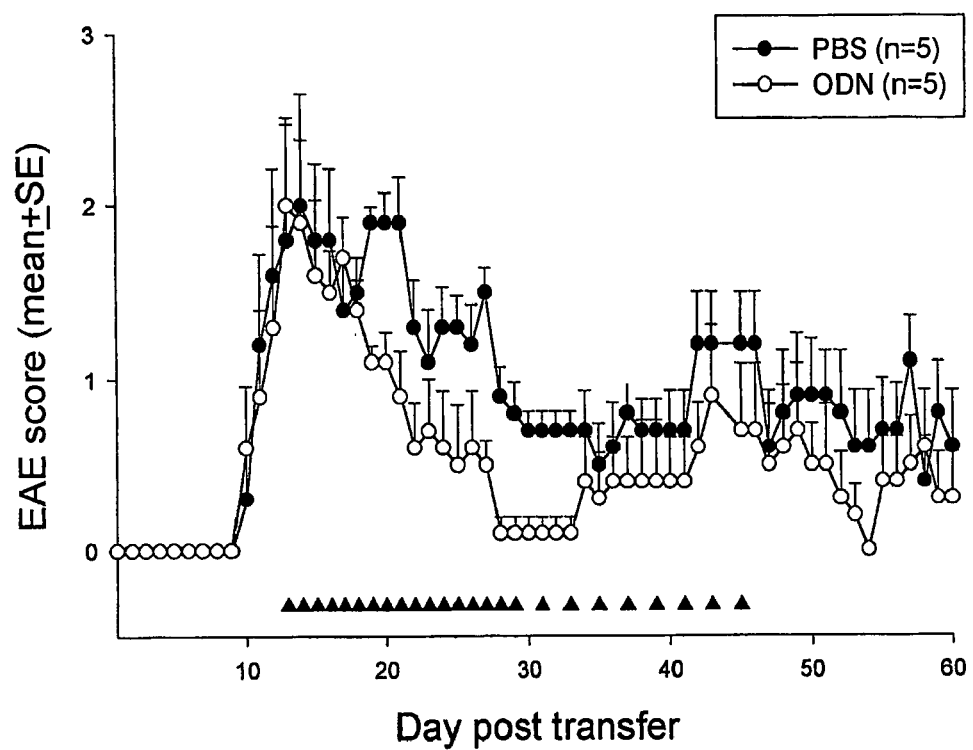

An additional experiment was performed to examine whether Smad7-antisense ODN administration is therapeutically effective (FIG. 4). Treatment with 100 μg Smad7-as-ODN initiated at the peak of acute disease and administered once daily for 17 days and then every other day for 17 days partially diminished the clinical disease severity. After 18 days of treatment three out of four mice had recovered completely from clinical disease (Table 4). The EAE-score was decreased significantly between days 18-20 (i.e. approximately 1 week after treatment initiation) and days 26-32 post transfer. The better outcome of mice treated with Smad7-as-ODN is confirmed by comparing the cumulative disease scores from days 12-60, i.e. the end of the observation period (Table 4). This documents the therapeutic potential of Smad7-as-PTO-Oligonucleotides for ongoing autoimmune CNS disease.

TABLE 4

|  | Smad7-as | PBS |
| --- | --- | --- |
| group size | n = 5 | n = 5 |
| EAE-incidence | 5/5 | 5/5 |
| EAE-prevalence (day 12) | 4/5 | 3/5 |
| EAE-prevalence (day 30) | 1/5 | 5/5 |
| EAE-prevalence (day 50) | 1/5 | 3/5 |
| cumulative score (d 1-12) | 24 | 24.5 |
| cumulative score (d 12-60) | 137.5 | 239.5 |
| relapse rate (mean ± SE) | 0.4 ± 0.22 | 0.4 ± 0.22 |
| relapse (number/animals) | 2/2 | 2/2 |

TABLE 3

|  | Smad7-as | Smad7-as2 | PBS | Smad7-mut4-as |
| --- | --- | --- | --- | --- |
| group size | n = 7 | n = 6 | n = 6 | n = 6 |
| EAE-incidence | 6/7 | 5/6 | 5/6 | 5/6 |
| EAE-prevalence (day 12) | 5/7 | 3/6 | 4/6 | 5/6 |
| EAE-prevalence (day 30) | 6/7 | 2/6 | 4/6 | 5/6 |
| day of onset (mean ± SE)* | 10.67 ± 0.81 | 15.80 ± 3.69 | 10.40 ± 1.66 | 8.33 ± 1.12 |
| max. score (mean ± SE) | 2.36 ± 0.37 | 1.67 ± 0.35 | 2.58 ± 0.61 | 3.25 ± 0.68 |
| deaths | 0 | 0 | 1 | 2 |

*sick animals only

Effects of therapeutic Smad7-as-ODN treatment on clinical course of EAE. Groups of five mice were treated with 100 µg of Smad7-as-ODN or PBS starting at the peak of disease (FIG. 4). After 18 days of treatment 3 out of 4 diseased mice had clinically recovered completely. The cumulative disease score showed a remarkable reduction in the Smad7-as-ODN group.

EXAMPLE 3

Transfer of in Vitro Smad7-Antisense-Treated LNC Fails to Induce at-EAE

Figure 5:
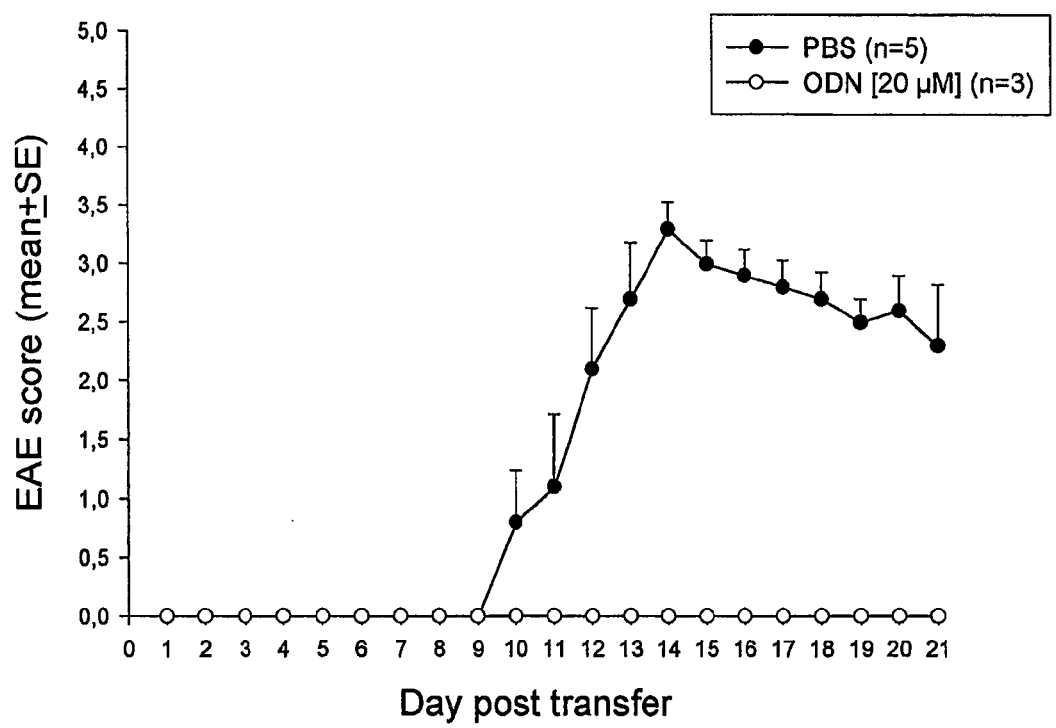
Figure 6:
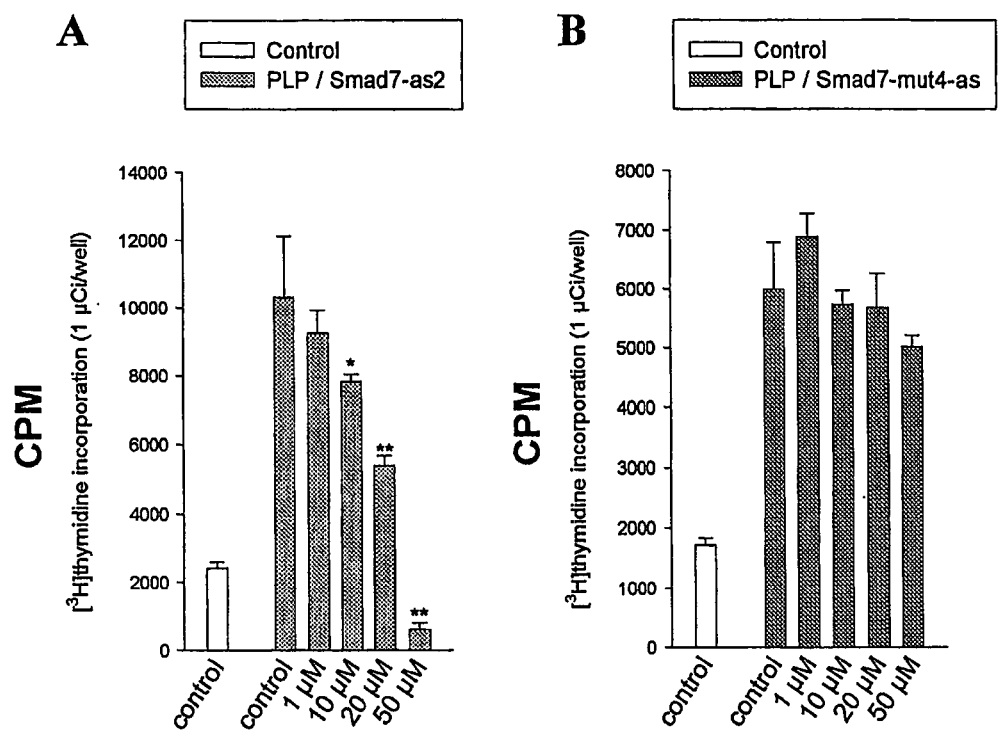

It was also investigated wether Smad7-as-ODN-treatment interferes with reactivation of PLP-specific T-cells in vitro and alters the encephalitogenicity of these cells. Therefore freshly isolated LNC from PLP-immunised SJL mice were restimulated with PLP(139-151) for 96 hours adding 20 µM of Smad7-as-ODN. The proliferation of cells cultured in the presence of Smad7-as-ODN was reduced by approximately 30% as compared to the PBS-treated cells (data not shown). While the injection of $5 \times 10^6$ PBS-treated LNC in naive recipients induced typical EAE-signs starting at day 9, the transfer-of-Smad7-as-ODN-treated LNC -failed to induce clinical signs during the observation period of 3 weeks (FIG. 5). This suggests that Smad7-as-ODN-treatment can prevent the reactivation of primed autoreactive T cells and block their disease-inducing properties.

EXAMPLE 4

Figure 7:
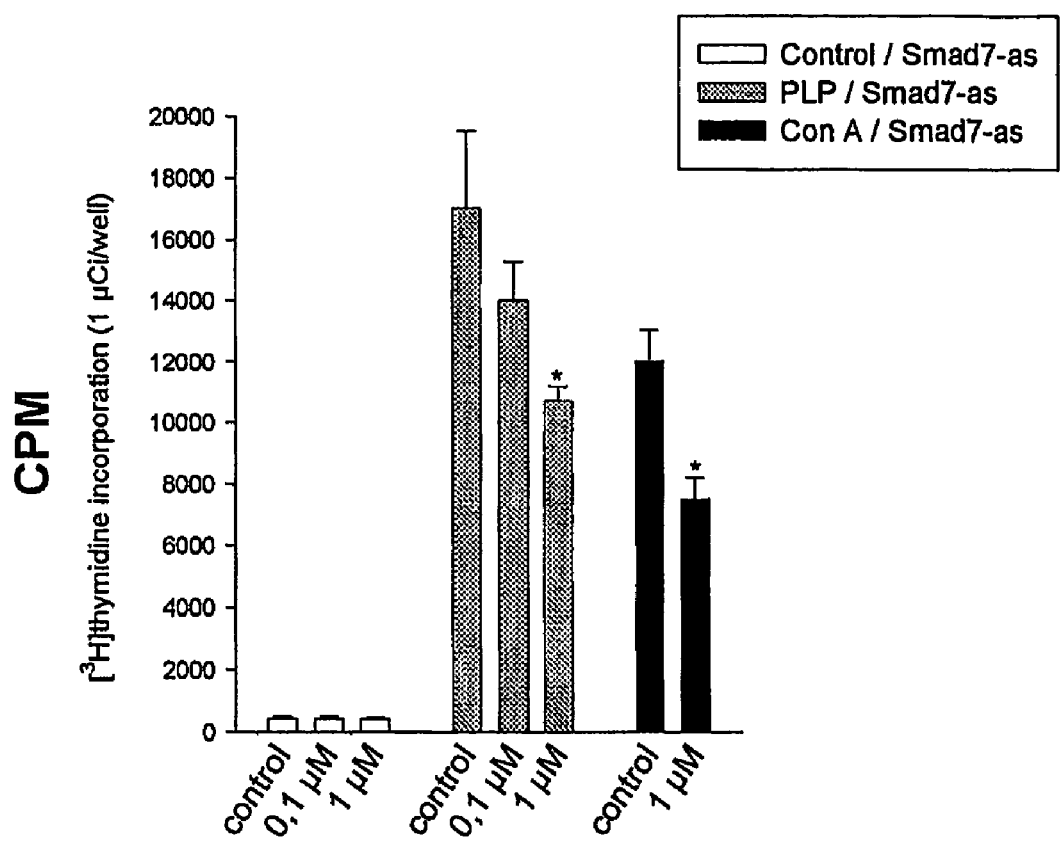

Smad7-Antisense-Treatment Diminishes the Proliferation of Activated LNC in Vitro To analyze the potential mechanisms of the treatment effect, we examined the effect of Smad7-as-ODN on antigen-restimulation of PLP-primed LNC in vitro. Coincubation of primed LNC and antigen with Smad7-as2-ODN for 96 hours dose-dependently suppressed proliferation (FIG. 6a), whereas the presence of Smad7-mut4-as-ODN which has only 80% complementarity to the Smad7 mRNA did not have an effect on LNC-proliferation at all (FIG. 6b). The reduction of proliferation by Smad7-as2-ODN was statistically highly significant ($p<0.005$) at concentrations of 20 µM. Smad7-as-ODN also potently inhibited proliferation of PLP-restimulated as well as ConA-stimulated LNC at a concentration as low as 1 µM (FIG. 7). Smad7-as-ODN did not have pro- or antiproliferative effects on resting LNC in low concentrations (FIG. 7).

EXAMPLE 5

Figure 8:
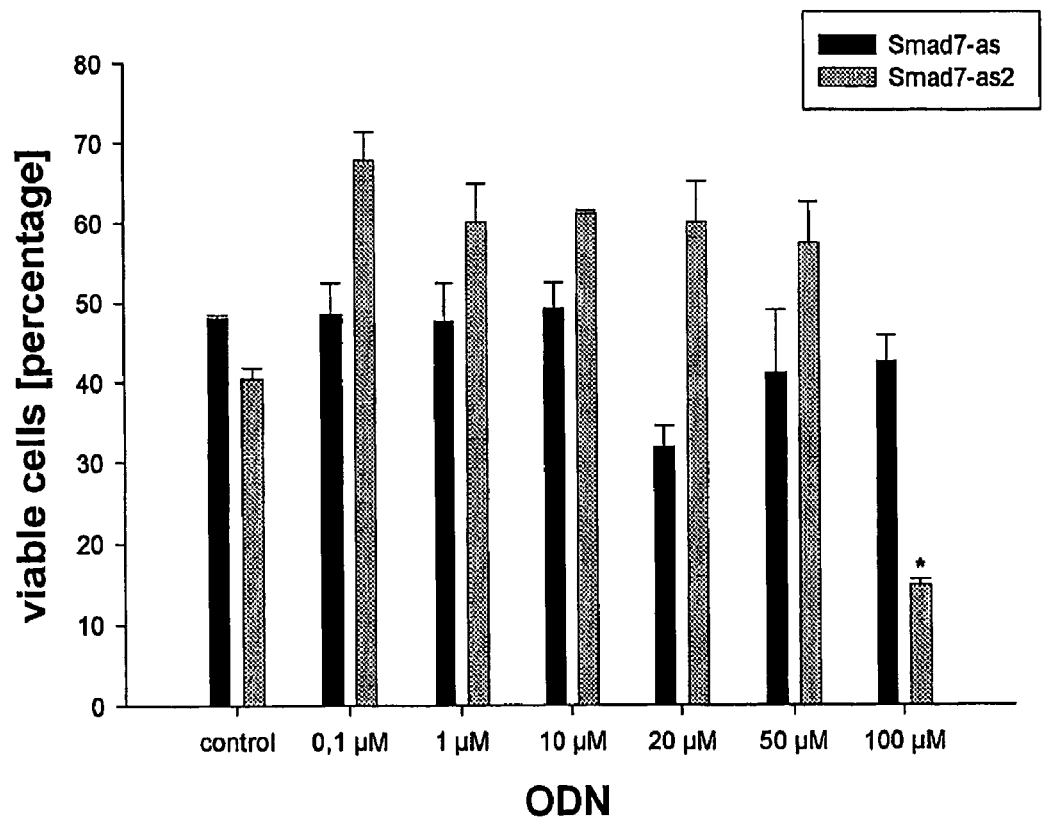
Figure 9:
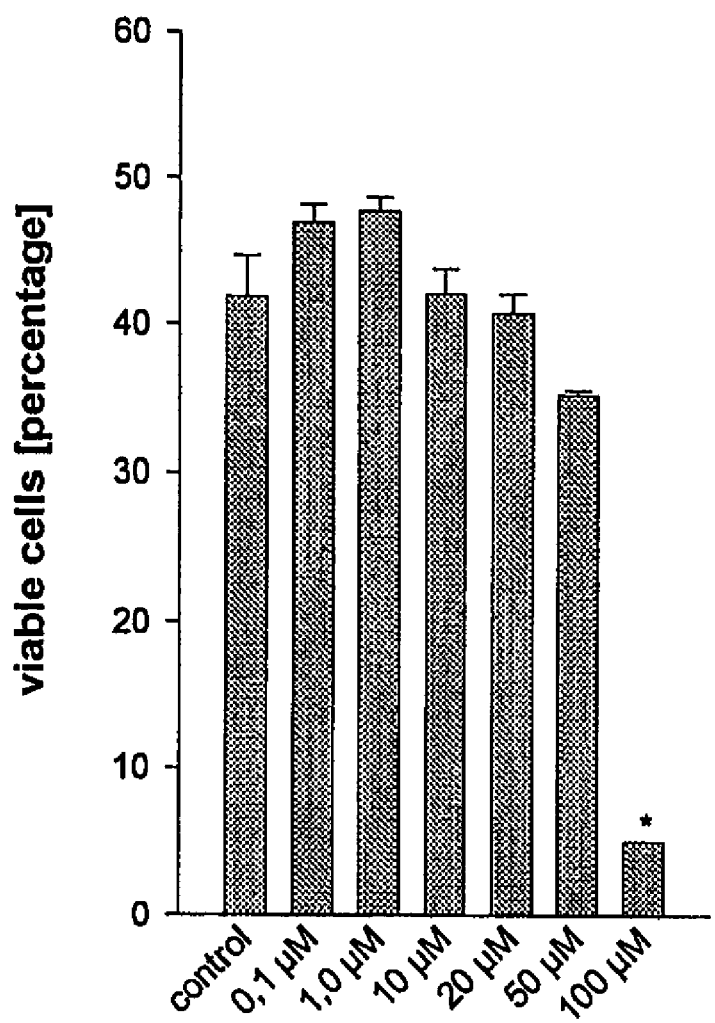

Absence of Toxicity of Smad7-Antisense Oligonucleotides Against Activated LNC in Vitro To exclude a toxic effect of Smad7-as-ODN against LNC as a possible explanation for the highly reduced proliferation rate in vitro toxicity assays with trypane blue staining were performed. Comparing 20 µM Smad7-as-ODN with PBS added to LNC cultures restimulated with peptide, no decrease in the proportion of viable cells was observed. When PLP-primed LNC were restimulated with PLP and coincubated with Smad7-as-ODN in increasing concentrations for 96 hours no significant loss of cell viability was observed in concentrations up to 100 µM (FIGS. 8 and 9). Using Smad7-as2-ODN a reduction of viable cells was only seen at >50 µM (100 µM). This result was confirmed by FACS-analysis and propidium iodide staining. Even at concentrations of 50 µM Smad7-as2-ODN which potently suppress T cell proliferation the viability of the LNC was not significantly affected.

EXAMPLE 6

Long Term Smad7-Antisense-Treatment Leads not to Adverse Side Effects Locally or Systemically Mice treated with Smad7-as- or Smad7-as2-ODN did not show obvious changes of behavior and did not look different from control mice except for signs produced by EAE itself. Autopsy of the animals immediately after cervical dislocation showed no signs of pathologic changes. Histological evaluation including HE and Masson-Goldner staining gave no hints of increased production of connective tissue in all organs examined (brain, spinal cord, liver, kidney, spleen, lung, heart, skin). A dilatation of the proximal renal tubules and a widening of the glomerular capsular space was observed in kidneys of animals of all treatment groups, including mice treated with PBS. In addition, prominent multinucleated macrophages were detected in spleens, as typical for EAE, with no difference between treatment groups.

EXAMPLE 7

Priming

Figure 10:
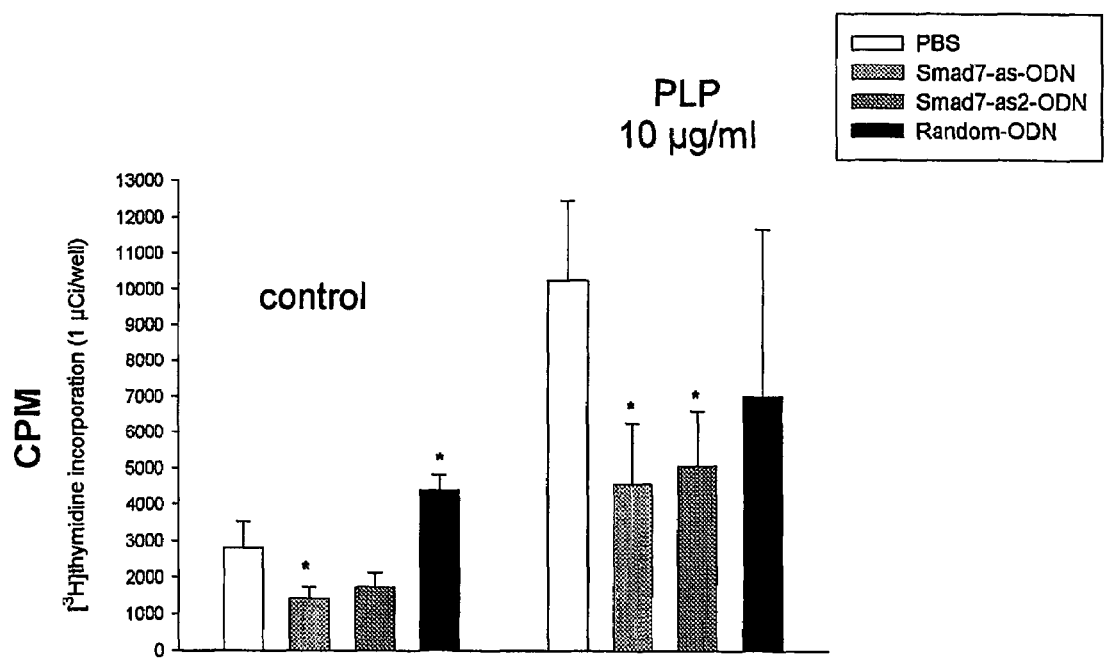

Treatment with Smad7-as-ODN in vivo inhibits the induction of an autoreactive T cell response. Cells from PBS-treated mice show a strong antigen-specific proliferation in contrast to the blunted proliferative response of cells from mice treated with antisense molecules (FIG. 10). The cells from the mice treated with random-ODN proliferated in culture even without adding peptide antigen.

EXAMPLE 8

Smad7-Antisense-Treatment Attenuates Ischemic Injury in a Model of Focal Cerebral Ischemia (Stroke)

The biological effects of Smad-7-antisense oligonucleotide application were also tested in a rodent model of focal cerebral ischemia. After 90-minutes intraluminal filament occlusion of the right middle cerebral artery in adult rats, either 400 pmol Smad7-as2-ODN (SEQ ID NO: 20) antisense oligonucleotides per kg body weight or the same amount of the respective Smad7-sense oligonucleotide 5'-ctgcggg-gagaaggggcgac-3' (SEQ ID NO: 43) as a treatment control, respectively, were infused into the right internal carotid artery continuously during the first 60 minutes of reperfusion. Rats underwent Magnetic Resonance Imaging (MRI) after 7 days and 4 weeks for in-vivo infarct volumetry. Afterwards, animals were sacrificed for histological evaluation of the ischemic brain injury.

Data from a series of experiments showed a reduction of infarct volume in Smad7-antisense-treated rats as compared to controls. The ischemic infarction in Smad7-antisense-treated rats predominantly was restricted to the basal ganglia, whereas, the overlying cerebral cortex was well preserved (FIG. 11). Since this pattern of ischemic lesion is very similar to that observed in recent experiments, using anti-apoptotic compounds, tentative interpretation of these results with Smad7-antisense application in focal cerebral ischemia strongly support the idea that inhibition of Smad7, i.e. reinforcement of the effects of tumor growth factor-beta (TGFbeta), features anti-inflammatory and anti-apoptotic neuroprotective effects in the ischemic penumbra.

EXAMPLE 9

Methodological Part of the Further Examples Related to EAE Experiments in Mice

Material and Methods are described for the examples 10 to 14 and only if they have not been detailed within example 1. All procedures were conducted according to protocols approved by the commission of animal protection at the University of Regensburg.

Smad7-Antisense-ODN

In addition to Smad7-as2-ODN (SEQ ID NO: 20 ) and Smad7-as-ODN (SEQ ID NO: 39) used in the examples 2-8, Smad7-as3-ODN (SEQ ID NO:21) and Smad7-as4-ODN (SEQ ID NO: 9) were used for treatment experiments and/or T cell proliferation assays.

T Cell Proliferation Assays:

Spleens were dissected and lymphocytes isolated by Ficoll-Paque Plus (Amersham Biosciences, Uppsala, Sweden). CD4$^+$ and CD8$^+$ T cells were positively selected on MS-columns using magnetic microbeads coupled to anti-mouse-CD4 or anti-mouse- CD8, respectively (all Miltenyi Biotec, Bergisch Gladbach, Germany). The resulting enriched T cells (FIG. 17a), CD4$^+$ (FIG. 17b) and CD8$^+$ T cell (FIG. 17c) populations were stimulated on microtiter plates coated with anti-mouse-CD3-antibodies (Becton Dickinson, Two Oak Park, Bedford Mass., USA) for 72 hours in the presence of varying concentrations of Smad7-as2-ODN or Smad7-mut4-as-ODN as described in Materials and Methods. Uncoated wells or wells without antisense PTO-ODN, respectively, served as controls. Proliferation was measured by $^3$H-thymidine uptake as described above. Results are given as arithmetic means±standard error from cultures set up at least in triplicate.

Priming Studies

The priming studies described in FIGS. 18 and 19 and example 17, respectively, were performed similarly to those described in FIG. 10/example 7. Treatment of immunized mice was performed between days 6 to 9 post immunization with 100 µg Smad7-as2-ODN or Smad7-mut4-as ODN or an equal amount of PBS, respectively. Mice were immunized with 200 µg PLP s.c. as described above. LNC cultures, adoptive transfer and proliferation assays were performed as described above.

Treatment with Smad7-Specific Short Interfering RNAs (siRNAs)

The following Smad7 (AF015260) RNA oligonucleotides were used:

annealing buffer for 1 min at 90° C. followed by 1 h at 37° C. (Elbashir, 2001a, Elbashir, 2001b). Starting with the day of transfer EAE-induced SJL mice were injected twice daily i.p. with 20 pmol annealed RNAi molecules solubilized in PBS (100 pmol/ml, pH 7.4).

EXAMPLE 10

Histopathology of Preventive Smad7 Antisense-Treatment in Vivo

Figure 13:
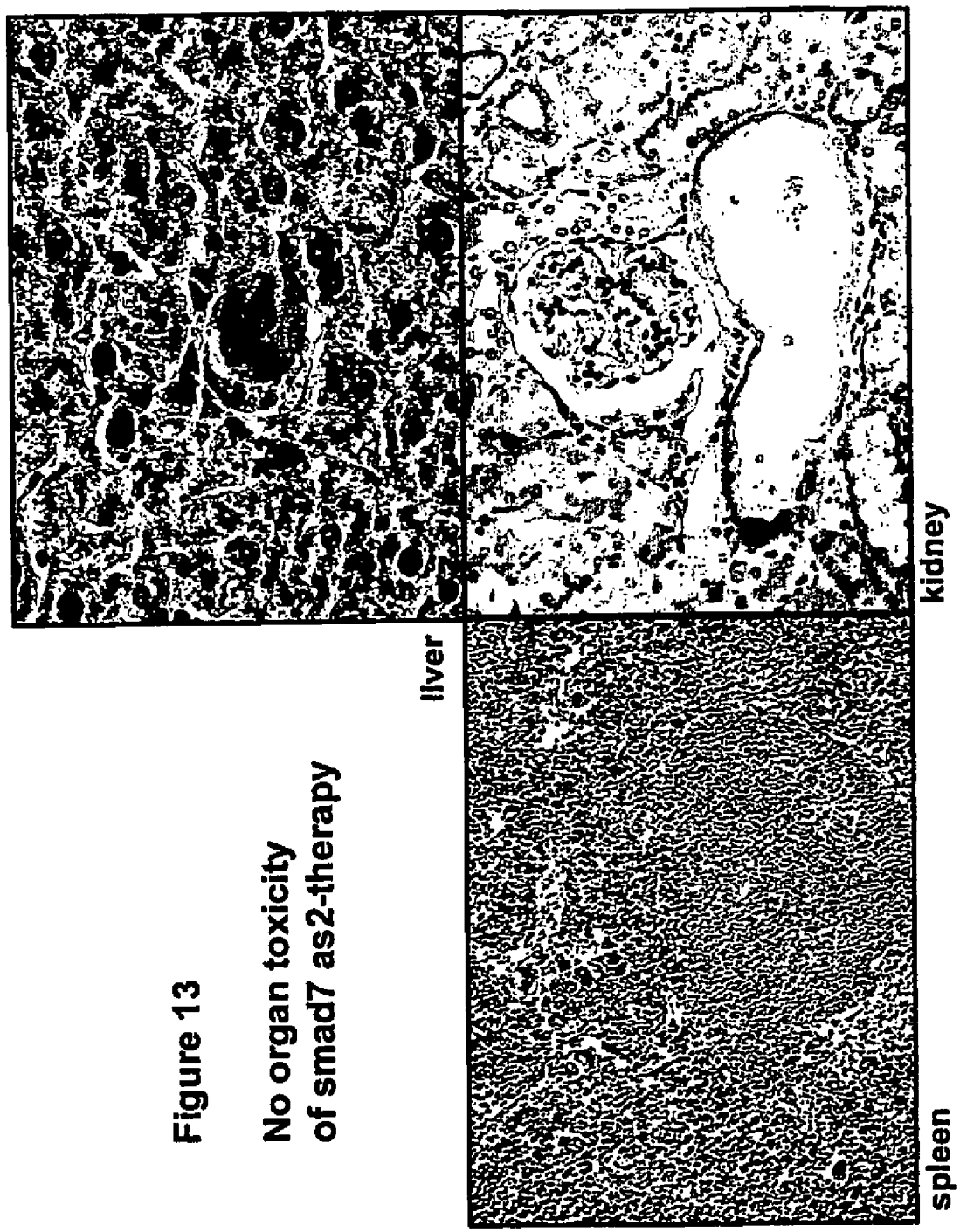

The histopathology of Smad7 antisense-treatment as seen in FIG. 13 in vivo is already described in example 2. The histopathological evaluation of organs outside of the CNS, as seen in FIG. 14, is described in example. 6. The figures illustrate that treatment with Smad7-as2-ODN suppresses inflammation within the CNS without inducing side-effects in non-CNS organs known to be affected by systemic administration of active TGF-beta.

EXAMPLE 11

Smad7 Antisense-Treatment Suppresses the Proliferation of Polyclonally Activated T Cells in Vitro This example provides evidence that antisense ODN specific for Smad7 dose-dependently inhibit the proliferative response associated with T cell activation mediated by the lectin Con A and plate-bound anti-CD3-antibodies.

In the first experiment whole spleen cell populations were stimulated over 96 hours with the lectin Con A (mediating polyclonal T cell activation) in the presence of varying concentrations of Smad7-as2-ODN (SEQ ID NO: 20) or Smad7-mut4-as-ODN (FIG. 14). Only Smad7-as2-ODN (SEQ ID NO: 20) significantly reduced proliferation. In the second experiment plate-bound anti-CD3 antibodies were used to stimulate T cells enriched over Ficoll, confirming this result (FIG. 15a). To determine whether this effect is limited to CD4+ or CD8+-T cells the respective subpopulations were isolated and stimulated with anti-CD3; the antiproliferative effect of Smad7-as2-ODN extends to both CD4+ or CD8+-T cells (FIGS. 15b and 15c).

EXAMPLE 12

Effects of Smad7 Antisense-Treatment in Vivo

To screen for further Smad7-specific antisense ODN potentially effective for treatment of autoimmune disease, Smad7-as3-ODN (SEQ ID NO: 21) and Smad7-as4-ODN (SEQ ID NO: 9) were tested in parallel with Smad7-as2-ODN (SEQ ID NO: 20) for their effect on PLP$_{139-151}$-specific LNC

```
RNAi1:  nt 3-23    5'-GUUCAGGACCAAACGAUCUGC-3',       (SEQ ID NO: 44)

nt 23-1    5'-GCAGAUCGUUUGGUCCUGAACAU-3'.    (SEQ ID NO: 45)

RNAi2:  nt 283-303 5'-CUCACGCACUCGGUGCUCAAG-3',      (SEQ ID NO: 46)

nt. 303-281 5'-CUUGAGCACCGAGUGCGUGAGCG-3'.   (SEQ ID NO: 47)
```

The RNA oligonucleotides were chemically synthesized on an Applied. Biosystems Synthesizer (Expedite 8909) using standard protocols by Ribopharma AG, Kulmbach. For annealing of siRNAs, 20 pM single strands were incubated in proliferation (FIG. 16a). All ODN tested dose-dependently suppressed proliferation, albeit with some variability between experiments (compare the effect of Smad7-as2-ODN in FIGS. 6, 14, 15, 16). Smad7-as3-ODN was somewhat less effective than Smad7-as2-ODN in preventing the development of EAE-signs when administered i.p. at a dose of 5 mg/kg daily from the day of adoptive transfer as described in Materials and Methods (FIG. 16b, table 5). This example supplements the results from example 2 (table 3) and example 4 in showing that various ODN specific for Smad7 suppress proliferation of T cells to a similar extent while the treatment effect on adoptive transfer EAE varies between ODN of different sequence.

TABLE 5

|  | Smad7-as2 | Smad7-as3 | Smad7-mut4-as | PBS |
| --- | --- | --- | --- | --- |
| group size | n = 7 | n = 7 | n = 7 | n = 7 |
| EAE-incidence | 7/7 | 7/7 | 7/7 | 7/7 |
| EAE-prevalence (day 11) | 2/7 | 3/7 | 7/7 | 7/7 |
| day of onset (mean ± SE) | 12.86 ± 0.84 | 11.86 ± 0.91 | 9.29 ± 0.60 | 9.29 ± 0.30 |
| max. score (mean ± SE) | 2.36 ± 0.17 | 2.5 ± 0.17 | 3.93 ± 0.36 | 2.71 ± 0.14 |
| cumulative score (d 1-28) | 167.0 | 234.0 | 467.5 | 280.0 |
| deaths | 0 | 0 | 3 (d7, 9, 11) | 0 |

Effects of preventive treatment with various Smad7-antisense-ODN. In the group treated with Smad7-mut4-as (an antisense molecule which is not capable of specifically interacting with or hybridizing to a Smad7 expression product (mRNA) or specifically interacting with/hybridizing to one or more nucleic acid molecules encoding Smad7) three mice died at early timepoints during the experiment. By convention they were given a grade 5 in the disease severity score until the end of the experiment.

EXAMPLE 13

Smad7 Antisense-Treatment Suppresses in Vivo Priming Responses

This examples add to data from example 7 in demonstrating that in vivo antigenic priming responses of autoreactive T cells are blunted during Smad7-as2-ODN-treatment and result in T cells of reduced encephalitogenicity.

Mice immunized with PLP peptide were treated with 100 µg (5 mg/kg) of Smad7-as2 or Smad7-mut4-as-ODN or an equal amount of PBS daily i.p. from day 6 to day 9 after immunization. LNC from these groups of mice were subsequently restimulated with antigen for 96 hours and used for proliferation assays (FIG. 17) and EAE-induction by adoptive transfer ($5 \times 10^6$ LNC per recipient mouse) (FIG. 18).

LNC from mice treated with Smad7-as2-ODN during antigenic priming proliferate less vigorously upon specific peptide restimulation as compared to LNC from untreated mice or from mice treated with Smad7-mut4-as-ODN (FIG. 17).

In FIG. 18, two separate experiments are shown. In contrast to LNC derived from mice treated with Smad7-mut4-as-ODN or PBS, LNC from mice treated with Smad7-as2-ODN either induced a highly attenuated clinical course (FIG. 18a, compare number of deaths) or did not induce EAE at all (FIG. 18b). The in vitro results from FIGS. 10 (example 7) and 17 suggest that this is due to partial inhibition of primary immune responses in Smad7-antisense-ODN-treated mice with the consequence that, upon antigenic stimulation, the disease-inducing capacity of the resulting T cells is considerably compromised.

EXAMPLE 14

Preventive Treatment with Smad7-Specific Short Interfering RNAs (siRNAs) Alleviates the Clinical Course in at-EAE The efficacy of Smad7-antisense-ODN treatment suggests that approaches targeting Smad7 mRNA or Smad7 protein, resulting in a reduction of mRNA and/or protein or their functional inhibition may be similarly effective for the in vivo treatment of disease. Therefore Smad7-specific short interfering RNAs (siRNAs) were synthesized and used for the treatment of adoptive transfer EAE (FIG. 19, table 6). Preventive treatment with two of these Smad7-specific siRNAs (RNAi1, RNAi2) resulted in an amelioration of clinical signs of EAE during the acute phase of the disease as compared to PBS-treated mice.

TABLE 6

|  | Smad7-RNAi1 | Smad7-RNAi2 | PBS |
| --- | --- | --- | --- |
| group size | n = 7 | n = 7 | n = 7 |
| EAE-incidence | 7/7 | 7/7 | 7/7 |
| EAE-prevalence (day 11) | 4/7 | 5/7 | 7/7 |
| day of onset (mean ± SE) | 11.29 ± 0.94 | 11.14 ± 0.87 | 9.29 ± 0.30 |
| max. score (mean ± SE) | 2.36 ± 0.19 | 2.5 ± 0.2 | 2.71 ± 0.14 |
| cumulative score (d 1-31) | 241.5 | 244.5 | 314.5 |
| Deaths | 0 | 0 | 0 |

Preventive treatment with Smad7-specific short interfering RNAs (siRNAs).

EXAMPLE 15

Methodological Part of the Examples Related to EAE Experiments in Rats

Animals:

Female Dark Agouti-rats (DA-rats) were obtained from Harlan Winkelmann (Borchen, Germany). Rats were 13 weeks old when used for immunization procedures. Rats were housed in normal cages with free access to food and water; paralyzed rats were afforded easier access to food and water.

Antigens:

The N-terminal fragment of rat myelin oligodendrocyte glycoprotein (MOG) containing the amino acids 1-125 (cDNA obtained as a kind gift from C. Linington, Munich) were expressed in *Escherichia coli* and purified to homiogeneity by chelate chromatography as described by Amor (Amor, 1994). The amino acid sequence of recombinant rat-MOG protein (AA 1-125) depicted in SEQ ID NO: 84 further comprises a 6×His peptide tag introduced for the ease of purification. The purified protein in 6M urea was dialyzed against PBS and the preparations obtained were stored at −20° C. For simplicity this MOG-fragment used is named "MOG" in the remainder of this application.

Induction, Treatment and Evaluation of MOG-Induced EAE:

An emulsion was prepared containing 65 µg MOG in PBS and an equal volume of incomplete Freund's adjuvant supplemented with 400 µg of Mycobacterium tuberculosis (H37RA, see example 1) in an inoculation volume of 200 µl per immunized rat. Immunizations were performed in anesthetized rats intradermally at the base of the tail.

Treatment with Smad7-as2-ODN or Smad7-mut4-as-ODN or an equal amount of PBS was performed as indicated in the examples I and 9. Rats were examined daily for signs of disease and graded on a scale of increasing severity from 0 to 5 as follows: 0 no signs; 0.5 partial tail weakness; 1 limp tail; 2 partial hindlimb weakness or hemiparesis; 3 complete paralysis of at least one hindlimb; 4 severe forelimb weakness; 5 moribund or dead.

EXAMPLE 16

Preventive Smad7 Antisense-Treatment Ameliorates the Clinical Course of Active MOG-Induced EAE in Rats Adoptive transfer EAE in SJL-mice is a model for the human autoimmune CNS disease multiple sclerosis. The treatment results as demonstrated in the previous examples therefore suggest that treatments functionally inhibiting Smad7 mRNA and/or protein such as Smad7-specific antisense ODN represent a promising approach to treat multiple sclerosis or related autoimmune inflammatory diseases of the CNS. To verify this hypothesis a second disease model relevant for multiple sclerosis was chosen. This model, EAE induced by immunization with the N-terminal fragment of MOG differs significantly from the adoptive transfer model. With the presence of significant demyelination and the putative contribution of antibodies during lesion pathogenesis it probably even more closely represents the human disease than murine EAE (Storch, 1998). Interestingly preventive Smad7 antisense-treatment ameliorated the clinical course of MOG-induced EAE in rats treated i.p. with 5 mg/kg Smad7-as2-ODN. The development of clinical signs was delayed as compared to rats treated with PBS (FIG. 20, table 7).

TABLE 7

|  | Smad7-as2 | Smad7-mut4-as | PBS |
| --- | --- | --- | --- |
| group size | n = 8 | n = 8 | n = 8 |
| EAE-incidence | 5/8 | 6/8 | 6/8 |
| EAE-prevalence (day 14) | 1/8 | 6/8 | 6/8 |
| EAE-prevalence (day 17) | 3/8 | 4/8 | 6/8 |
| day of onset (mean ± SE)* | 15.20 ± 1.66 | 10.20 ± 1.42 | 11.50 ± 0.61 |
| max. score (mean ± SE) | 1.44 ± 0.49 | 1.69 ± 0.54 | 2.25 ± 0.62 |
| cumulative score (d 1-17) | 23.5 | 57.0 | 80.5 |

*sick animals only
Treatment of MOG-induced active EAE

EXAMPLE 17

Methodological Part of the Examples Related to Experimental Stroke

The following experiments conformed with the guidelines of the German law governing animal care. Animal protocols were approved by the Animal Care Committee of the Bavarian government and the local ethics committee.

Animals

Adult male Wistar rats (body weight 250-270 g) were supplied by Charles River (Sulzfeld, GermanyF) and were maintained with food and water ad libitum at 23° C. and 50% relative humidity for at least 5 days prior to surgery.

Surgery and Induction of Focal Cerebral Ischemia

Anesthesia was induced with 4% isoflurane inhalation and then maintained with 1.5% isoflurane in a gas mixture of 70% nitrogen and 30% oxygen after endotracheal intubation and mechanical ventilation by a pressure-controlled small animal respirator. Rectal temperature was monitored continuously throughout the experiment and was maintained at 37.0° C. by use of a thermostatically feed-back-regulated heating lamp and stage. After cannulation of the tail artery providing monitoring of blood pressure and blood gases, rats were placed in a stereotactic frame. The skull was exposed by a midline incision and two burr holes measuring 2 mm in diameter were drilled for bilateral monitoring of local cortical blood flow (ICBF). Both MCA supply territories were continuously monitored by laser doppler flowmetry (MBF3D, Moor Instruments, U.K.), and cortical EEG was recorded on both sides. After a midline incision of the neck had been carried out, the right carotid bifurcation was exposed and the extracranial branches of the internal carotid artery (ICA) were ligated and electrocoagulated, assisted by an operating microscope (Zeiss, Oberkochen, GermanyF). Subsequently, the external carotid artery (ECA) was ligated and cut distally to the superior thyreoid artery, after the common carotid artery had been occluded by a microclip (Biemer FD 68, Tuttlingen, GermanyF). Then, a silicone-coated 4-0 nylon monofilament (Ethicon) was introduced in the ECA and gently advanced through the ICA until its tip occluded the origin of the right MCA (Schmid-Elsaesser et al. 1998). As a result, ICBF in the right MCA territory dropped down to approximately 20% of baseline values. The endovascular filament remained in place until reperfusion was enabled through withdrawal of the filament and removal of the microclip at the common carotid artery after 90 minutes of ischemia. Two sham-operated rats were processed identically including ligation and cutting of the external carotid artery except for intraluminal filament occlusion of the MCA. Physiological variables including arterial blood pressure, heart rate, arterial blood gases ($pO_2$, $pCO_2$, pH, base excess, $O_2$ saturation), plasma glucose, and hematocrit were recorded 15 min prior to surgery and subsequently every 15 min throughout the experiment until the animals were replaced to their cages.

Local Intra-Arterial Administration of Specific Antisense ODN

The following single-stranded phosphorothioate PTO-ODN were used: Smad7-as2-ODN (Seq ID NO: 10) and Smad7-sense-ODN (SEQ ID NO: 43). Infusion of ODN beginning with reperfusion after 90 min ischemia was performed through a PE-catheter introduced via the external carotid artery into the internal carotid artery and gently pushed forward until its tip was located directly at the beginning of the carotid channel. Rats either were treated with 400 pmol Smad7-as2-ODN per kg body weight dissolved in 0.9% NaCl at pH 7.4 (100 pmol/0.5 ml over 1 hr; treatment, n=8) or with 400 pmol Smad7-sense-ODN per kg body weight dissolved in 0.9% NaCl at pH 7.4 (100 pmol/0.5 ml over 1 hr; control, n=8).

Immediately after infusion, the catheter was removed, followed by ligation of the external carotid artery stump and closure of the wound by suture. After withdrawal of volative anesthetics and restitution of sponteaneous respiration, the animals were extubated and monitored continuously regarding vital signs, body temperature, and neurological performance, before being replaced to their cages.

Clinical Evaluation

Neurological deficits were scored according to Bederson et al. (1986): 0, asymptomatic; 1, failure to extend the contralateral forepaw (mild); 2, circling to the contralateral side (moderate); and 3, loss of walking or righting reflex (severe). Only animals with a neurological deficit score of 2 or higher when extubated and alert were included into the subsequent steps of the protocol.

Infarct Volume Measurement by in-Vivo MRI

Seven days and three months after ischemia, rats were reanesthetized for quantification of the ischemic lesion by in vivo MRI. Measurements were performed on a 1.5 T MR scanner (Siemens Magnetom Vision, Erlangen, Germany) similar to the approach described by (Guzman, 2000). The head of the rat was positioned into the bore of a small surface coil (ID 5 cm) acting as a volume coil. Two types of sequences were used for scanning the rat brain: a $T_2$-weighted TSE sequence $T_2$: TR 2500, TE 96, ETL 7, TA 6:04, Acq 8, SL 2 mm, Gap 0, Ma 128×256, 4/8 RecFOV, FOV 84 mm) and a heavily Ti-weighted inversion recovery sequence (IR: TR 3000, TE 60, TI 150, ETL 11, TA 5:33, Acq 10, SL 1.5 mm, Gap 0, Ma 121×256, 4/8 RecFOV, FOV 109 mm). Scanning included axial and coronal series of both sequence types $T_2$, IR). A complete study following this protocol durated for approximately 45 min total measuring time.

Quantitative morphometrical evaluation of the infarcted area in each MRI slice was performed by an experienced neuroradiologist who was blinded to the experimental data, using a semi-automatic image analysis software (Image Analysis, NIH, Bethesda, Md., U.S.A.) on a Macintosh G3 computer. Since the inversion recovery sequences allow the differentiation of infarcted tissue from vital brain tissue most clearly, IR sequences (axial and coronal sections) were used for infarct volumetry. Basically, infarct volumes were calculated in $cm^3$ by calculating the sum of the areas of infarcted tissue of each plane, multiplied by the slice thickness.

Histology

Infarct volumes were also assessed semiquantitatively by histological evaluation. Subsequent to the second MRI at three months survival after MCA occlusion rats were sacrificed in deep anesthesia. After decapitation and cryofixation, brains were entirely cut into 40 μm coronal sections. Representative sections of the MCA territory were mounted and stained with cresyl violet (Nissl stain) or immunostained to glial fibrillary acid protein (GFAP; donkey-anti-rabbit IgG 1:1000; DAB-detected) for assessment of the ischemic lesion by light microscopy.

Statistical Analysis

A comparison between groups (Smad7-as2-ODN, Smad7-sense-ODN) was made by a one-way analysis of variance (ANOVA) with a post hoc Bonferroni test for multiple comparisons. Calculations were performed by use of a software package (SigmaStat) on an IBM computer.

EXAMPLE 18

Figure 21:
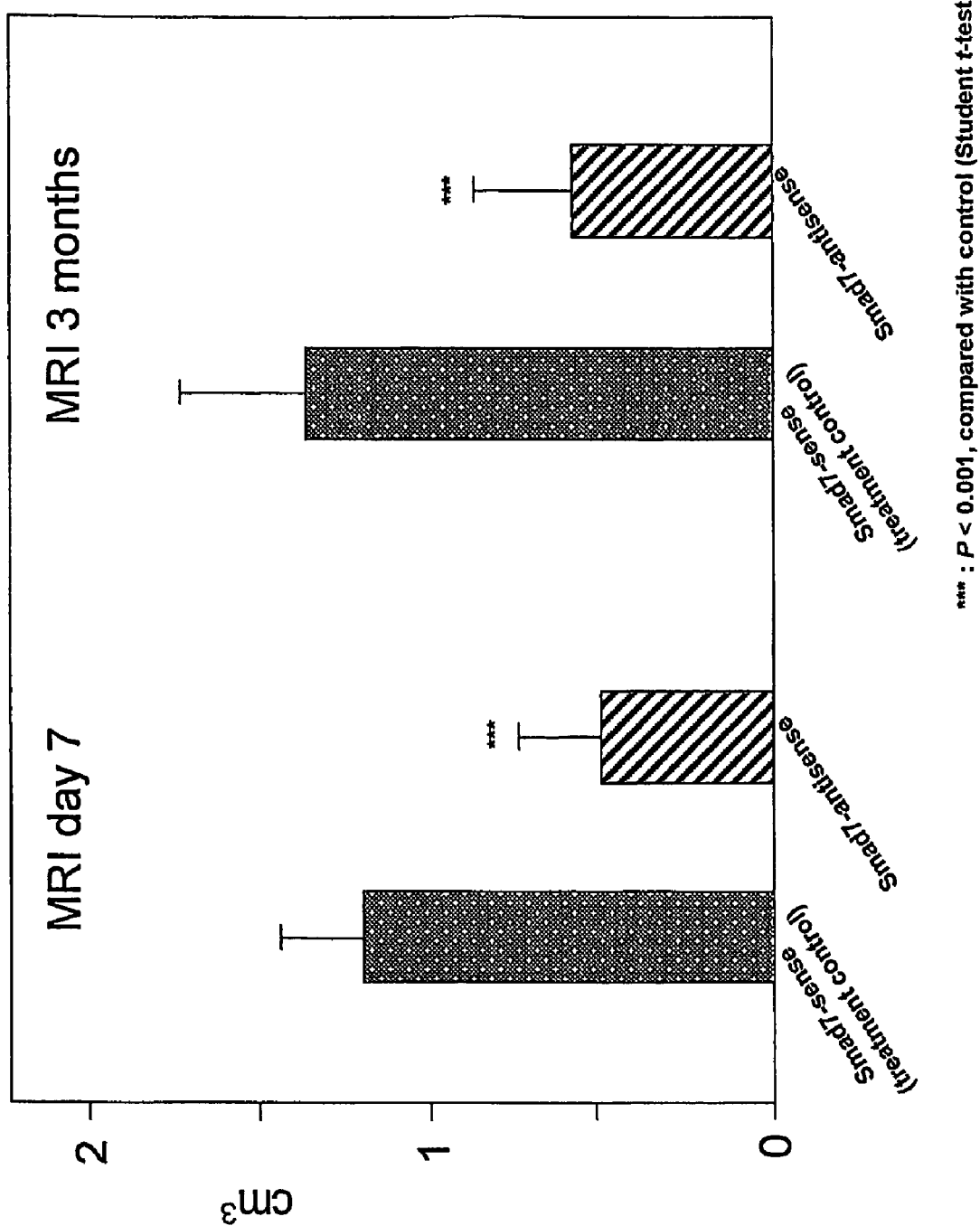
Figure 29:
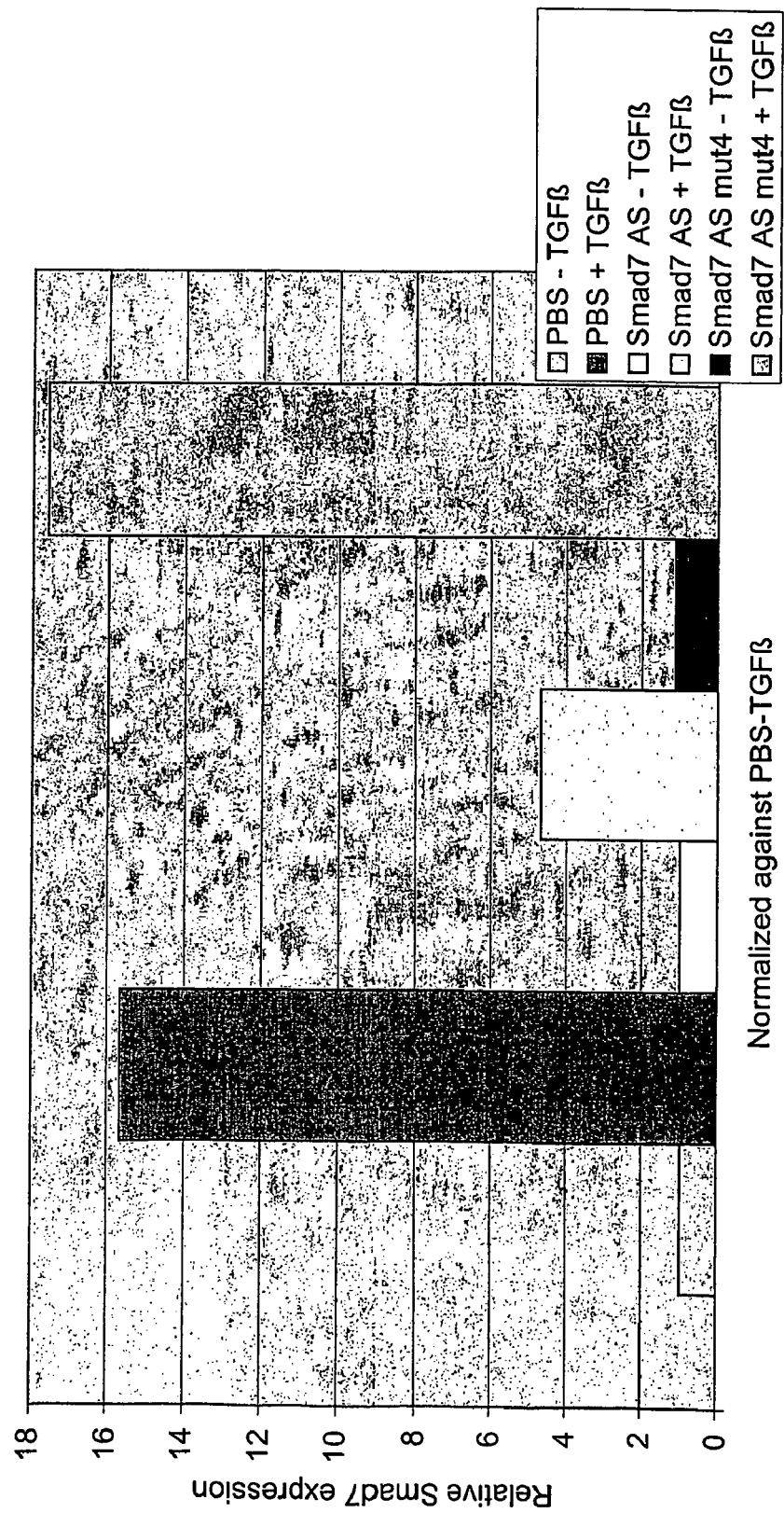

Local Smad7-Antisense-ODN Treatment Results in Reduced Infarct Volume on Day 7 and 3 Months After Focal Cerebral Ischemia In Vivo Magnetic Resonance Imaging Lesion sizes as measured by MRI infarct volumetry at day 7 (3 months) for rats treated by Smad7-sense-ODN or Smad7-as2-ODN were 1.32±0.33 $cm^3$ (1.55±0.35 $cm^3$) vs. 0.49×0.25 $cm^3$ (0.60×0.28 $cm^3$), respectively. Accordingly, the degree of neuroprotection in Smad7-as2 treated rats compared with control was 58.47% at day 7 and 55.88% at three months after ischemia ($p<0.001$). Thus, Smad7-as treatment was associated with a dramatic reduction of the ischemic injury in both the acute and the chronic stage of focal cerebral ischemia (FIG. 21).

Sequential in-vivo MRI findings from two representative animals either treated with Smad7-sense-ODN or Smad7-as2-ODN are illustrated in FIG. 22a-h. There was a close correlation between the extent of ischemic injury as demonstrated by the follow-up MRI and the histological appearance of the lesion. Strikingly, both basal ganglia and cerebral cortex were significantly more affected in Smad7-sense treated rats than in the Smad7-as2-ODN-treated group.

Histology

Semiquantitative histological assessment of the ischemic injury on specimen stained with cresyl violet or immunostained for the astrocyte marker glial fibrillary acidic protein (GFAP) confirmed the in-vivo MRI findings. Total infarct volumes were considerably smaller in Smad7-as2-ODN-treated rats as compared to rats treated with Smad7-sense-ODN. The protective effect of Smad7-as2-ODN included cerebral cortex and subcortical white matter, and basal ganglia (FIG. 22i-l). At the light microscopic level there was pronounced gliosis covering the lesion in specimen of both treatment groups, but no evidence for persisting inflammation at 3 months after stroke.

These data therefore indicate that local treatment with Smad7-specific antisense-ODN mediates significant neuroprotection and reduces infarct volumes after focal cerebral ischemia. This protection is already seen after administration of a single dose of antisense-ODN.

EXAMPLE 19

Jurkat T-cells (ECACC N° 88042803) were grown in RPMI medium with 10% FCS, Penicillin 1 U/ml, Streptomicin 10 μg/ml and Glutamine 20 mM. Before treatment, cells were changed to starvation medium without FCS. After 3 days cells were counted using the Neubauer chamber and plated in 24 well plates at 2×10⁶ cells/well, and then treated with Smad7-as2-ODN (10 μM), Smad7-mut-AS-ODN (10 μM) or PBS for 4 hours. Then cells were incubated with or without TGFbeta (5 ng/μl) for 30 minutes. The cells were centrifugated, washed, and the amount of 1×10⁷ cells was lysed with 600 μl RLT buffer according to the QIAGEN RNeasy mini (Catalog N° 74104) protocol. 90 ng total RNA was used for the one step RT PCR, using QuantiTect SYBR Green PCR Kit from QIAGEN (Catalog N° 204143) using Smad 7 primers and as standard the rRNA primer pair QuantumRNA Classic 18S from Ambion (Catalog N° 1716). Smad7 primers were sense: 5'-ATG TTC AGG ACC AAA CGA TCT GCG-3' (SEQ ID NO: 85) and antisense: 5'-AGC TGC CGC TCC TTC AGT TTC TT-3' (SEQ ID NO: 86). For amplification, the RotorGene Real Time PCR System (Corbett Research) was used, with the one step temperature profile: reverse transcriptase temperature 50°, 30 minutes;-activation of, polymerase, 95°, 1.5 minutes; 45 cycles of: denaturating temperature 94°, 20 secs, annealing temperature 59°, 30 secs, elongation temperature 72°, 120 secs. Fluorescense messure was done after each cycle. At the end, a melting curve (80°-950), hold 10 secs and messure of fluorescense was done to verify amplification of the expected PCR product. To measure the concentration of the produced DNA, we used a standard curve produced by amplification of given amounts of a Smad7 plasmid produced by cloning of the complete coding region of the human Smad7 mRNA into the pCR'4 Blunt TOPO cloning vector from Invitrogen (Catalog N° K2875-J10). To estimate the concentration of rRNA we used the standard RNA delivered with the primers (Qiagen).

REFERENCES

Agrawal S (1998) *Antisense Nucleic Acid Drug Dev.* 8, 135-139
Ali D (2001) *J Cereb Blood Flow Metab* 21, 820-827.
Amor S 1994 *J. Immunol.* 153, 4349-4356.
An H (2001) *J Org Chem,* 66, 2789-2801.
Ata A K 1997 *Acta Neuropathol (Berl)* 93, 326-33.
Baker J C (1996) *Genes Dev.* 10, 1880-1889.
Beck J (1991) *Acta Neurol Scand,* 84, 452-455.
Benveniste E N 1998 *Cytokine Growth Factor Rev* 9, 259-75.
Bitzer M (1998) *Kidney Blood Press Res,* 21, 1-12.
Bitzer M (2000) *Genes Dev.* 14,187-197.
Blind M (1999). *Proc Natl Acad Sci USA* 96, 3606-3610.
Blobe G C (2000) *N Engl J Med* 342, 1350-1358.
Border W A (1994) *N Engl J Med* 331, 1286-1292.
Brocke S (1996) *Methods* 9, 458-462.
Brummelkamp T R (2002) *Science* 296, 550-553
Buisson A 1998 *Faseb J* 12, 1683-91.
Calabresi P A (1998) *Neurology* 51, 289-92.
Chalaux E 1999 *FEBS Lett* 457, 478-82.
Chen Y (1996 *Proc Natl Acad Sci USA* 93, 388-391.
Chen L Z (1998) *Proc. Natl. Acad. Sci. U.S.A.* 95, 12516-12521.
Chen W (2001) *J Exp Med* 194, 439-453.
Chen Y (1996) *Proc. Natl. Acad. Sci. U.S.A.,* 93, 388-391.
Choi D W 1996 *Curr Opin Neurobiol* 6, 667-72.
Croxford J L (1998) *J Immunol,* 160, 5181-5187.
Datta P K (2000) *Mol Cell Biol* 20, 3157-3167.
De Groot C J (1999) *J Neuropathol Exp Neurol* 58, 174-187.
De Jong E S (2002) *Curr Trop Med Chem* 2, 289-302
Derynck R (1986) *J Biol Chem* 261, 4377-4379.
Derynck R (1987) *Nucleic Acids Res* 15, 3188-3189.
De Oliveira M C (2000) *Life Sci* 67, 1625-1637.
Diab A (1998) *J Neuroimmunol* 85, 146-154.
Dixon C E 1991 *J Neurosci Methods* 39, 253-62.
Donze O (2002) *Nucleic Acids Res* 30, e46.
Dorner (1996) *Bioorg Med Chem* 4, 709-715.
Ebisawa T (2001). *J Biol Chem* 276, 12477-12480.
Elbashi S M (2002), *Methods* 26:199-213.
Elbashir S M (2001a) *Nature* 411, 494-498.
Elbashir S M (2001b) *Genes Dev.* 15, 188-200.
Faden A I 1993 *Crit Rev Neurobiol* 7, 175-86.
Famulok M (1998) *Curr Opin Chem Biol* 2, 320-327
Ferrigno O 2002 *Oncogene* 21, 4879-84.
Fiocchi C (1998) *Gastroenterology* 115, 182-205.
Francis G (1997) *Ann Neurol* 42, 467
Friedman S L (1993) *N Engl J Med* 328, 1828-1835.
Garside P (2001) *Semin Immunol* 13, 177-185
Gayo A (2000) *J Neurol Sci* 179, 43-49.
Gold L (1995) *Annu Rev Biochem* 64, 763-797.
Gonnella P A (1998) *J Immunol* 160, 4708-4718
Grishok A (2001) *Cel.* 106, 23-34.
Gross C E 1993 *Stroke* 24, 558-62.
Gross C E (1994) *Neurol Res.* 16:465-470.
Guzman R 2000 *J Neurosci Methods* 97, 77-85.
Hammond S M (2001) *Science* 293, 1146-1150.
Hailer N P (2001) *Eur J Neurosci* 14, 315-326.
Han J (1994). *Antisense Res Dev* 4, 53-65.
Hayashi H (1997) *Cell* 89, 1165-1173.
Hefferan T E 2000 *J Biol Chem* 275, 20255-9.
Henrich-Noack P 1996 *Stroke* 27, 1609-14; discussion 1615.
Hermann T (2000) *Angew Chem Int Ed Engl* 39, 1890-1904.
Hoffman L M (1998) *Res. Immunol* 149, 790-794.
Hughes D (1980) *Clin Exp Immunol,* 40, 523-531.
Hutvagner G (2001) *Science* 293, 834-838.
Imamura T (1997) *Nature* 389, 622-626.
Inoue H (1998) *Mol Biol Cell* 9, 2145-2156.
Ishisaki (1999) *J Biol Chem* 274, 13637-13642.
Issazadeh S (1998) *J Immunol.* 161, 1104-1112.
Issazadeh S (1995) *J Neuroimmunol.* 61, 205-212.
Itoh F (2001) *EMBO J* 15, 4132-4142.
Itoh S (2000) *Eur J Biochem* 267, 6954-6967.
Itoh S (1998) *J Biol Chem.* 273, 29195-29201.
Johns L D (1991) *J. Immunol* 147, 1792-1796.
Johns L D (1993) *J Neuroimmunol* 1993; 47, 1-7.
Johnsen S A 2002a *Oncogene* 21, 5783-90.
Johnsen S A 2002b *J Cell Biochem* 87, 233-41.
Johnsen S A 2002c *J Biol Chem* 277, 30754-9.
Kanamaru C (2001) *J Biol Chem* 276, 45636-45641
Kandimalla E (1994) *Gene* 149, 115-121.
Karpus W J (1999) *J Neurovirol* 5, 1-2.
Kasus-Jacobi A (2000) *Oncogene.* 19, 2052-2059.
Kavsak P (2000) *Mol Cell* 6, 1365-1375.
Khanna A K (1999) *Transplantation* 67, 882-889.
Khoury S J (1992) *J Exp Med.* 176, 1355-1364.
Kiefer R (1998) *J Neuropathol Exp Neurol* 57, 385-395.
Kim J S 1996 *Stroke* 27, 1553-7.
Kriegistein K 1998 *J Neurosci* 18, 9822-34.
Krupinski J 1996 *Stroke* 27, 852-7.
Kulkarni A B 1993 *Am J Pathol* 143, 3-9.
Kulkarni A B (1993) *Proc Natl Acad Sci USA,* 90, 770-774.
Kuruvilla A P (1991) *Proc Natl Acad Sci USA* 88, 2918-2921.
Lagna G (1996) *Nature* 383, 832-836
Leaman D W (1999) *Meth Enzymol* 18, 252-265.
Lehrmann E 1998 *Glia* 24, 437-48.
Lehrmann E 1995 *Exp Neurol* 131, 114-23.
Letterio J J (2000) *Cytokine Growth Factor Rev* 11, 81-87.
Letterio J L (1998) *Annu. Rev. Immunol.* 16, 137-161.
Li J H 2002 *J Am Soc Nephrol* 13, 1464-72.
Liblau R S (1995) *Immunol. Today* 16, 34-38.
Lindholm D 1992 *J Cell Biol* 117, 395-400.
Liu F (1996). *Nature* 381, 620-623.
Logan A 1994 *Eur J Neurosci* 6, 355-63.
Logan A 1992 *Brain Res* 587, 216-25.
Martin R (1992) *Annu. Rev. Immunol* 10, 153-187.
Massague J (1987) *Cell* 49, 437-438.
Mathisen P M (1997) *J Exp Med* 186, 159-164.
Mattson M P 1997 *Brain Res Brain Res Rev* 23, 47-61.
Mayer G (2001) *Proc Natl Acad Sci USA* 98, 4961-4965.
McNeill H 1994 *Neuroreport* 5, 901-4.
Miller A (1992) *Proc. Natl. Acad. Sci. U.S.A.,* 89, 421-425.
Miller S D (1994) *Immunol Today* 15, 356-361.
Miyazono K (2001) *J Cell Physiol* 187, 265-276.
Mokhtarian F (1994) *J Immunol* 152, 6003-10.
Monteleone G (2001) *J Clin Invest* 108, 601-609.
Monroe R J (1999) *Immunity* 11, 201-212.
Morganti-Kossmann M C (1999) *J Neurotrauma.* 16, 617-622.
Nagarajan R P (1999) *J Biol Chem* 274, 33412-33418.
Nakao A (2000) *J Exp Med* 192, 151-158.
Nicholson L B (1995) *Immunity* 3, 397-405.
O'Garra A (1997) *Curr Opin Immunol* 9, 872-883.
Okuda Y (1995) *J Neuroimmunol* 62, 103-112.
Ostresh J M (1996) *Methods Enzymol.* 267, 220-324.
Ostendorf T (2001) *J Am Soc Nephrol.* 12, 909-918.

Pabo C O (1996) *Bioorg Med Chem.* 4, 1545-1558.
Pang L 2001 *Stroke* 32, 544-52.
Panitch H (1997) *Ann Neurol* 42, 459-463.
Peterziel H 2002 *J Cell Biol.* 159, 157-167
Prakash T P (2001) *Nucleosides Nucleotides Nucleic Acids,* 20, 829-832.
Pratt B M 1997 *Cytokine Growth Factor Rev* 8, 267-92.
Prehn J H 1993 *J Cereb Blood Flow Metab* 13, 521-5.
Pulaski L (2001) *J Biol Chem* 276, 14344-14349.
Racke M K (1994) *J Exp Med* 180, 1961-1966.
Racke M K (1991) *J. Immunol.,* 146, 3012-3017.
Racke M K (1992). *Int Immunol* 4, 615-620.
Racke M K (1993) *J Neuroimmunol* 46, 175-183.
Raine C S (1995) *Nature Medicine* 1, 211-214.
Ribeiro A 1999 *Hepatology* 30, 1490-7.
Rimaniol A C 1995 *Neuroreport* 7, 133-6.
Rose R B (1996) *Biochemistry* 35, 12933-12944
Ruocco A (1999) *J Cereb Blood Flow Metab* 19, 1345-1353
Sandrock B (2001) *J Biol Chem* 276, 35328-35333.
Santambrogio L (1993) *J. Immunol* 151, 1116-1127.
Santambrogio L (1998) *J Neuroimmunol* 81, 1-13.
Samani T D (2001) *Antisense Nucleic Acid Drug Dev,* 11, 129-136.
Schwope I (1999) *J Org Chem,* 64:4749-4761.
Semple S C (2001) *Biochim Biophys Acta,* 10, 152-166.
Sharma K (2000) *Cytokine Growth Factor Rev* 11, 115-23.
Slevin M (2000) *Stroke* 31, 1863-1870.
Smith L (2000) *Eur J Pharmacol Sci* 11, 191-198.
Souchelnytskyi S (1998) *J Biol Chem.* 273, 25364-25370.
Sporn M B (1989) *Jama* 262, 938-941.
Sporn M B (1987). *J Cell Biol* 105, 1039-45.
Stanzani L 2001 *Cerebrovasc Dis* 12, 240-4.
Steinman L (1997) *J Exp Med* 185, 2039-2041.
Storch M K 1998 *Brain Pathol* 8, 681-94.
Subramaniam M 1995 *Nucleic Acids Res* 23, 4907-12.
Subramaniam M 1998 *J Cell Biochem* 68, 226-36.
Suchanek E G (1986) *Biochemistry* 25, 5987-5991.
Sudol M 1994 *Oncogene* 9, 2145-52.
Sullivan P 2002 *Brain Res* 949, 88-96.
Sun S (2000) *Curr Opin Mol Ther* 2, 100-105.
Suzuki C 2002 *J Biol Chem.* 29, 1621-1625
Tachibana I 1997 *J Clin Invest* 99, 2365-74.
Tanaka M (1999) *J Neurobiol* 41, 524-539.
Tanuma N (2000) *J Neuroimmunol* 108, 171-180.
Teillaud J L (1999) *Pathol Biol* 47, 771-775.
Terrell T G (1993) *Int Rev Exp Pathol* 34 Pt B, 43-67.
Thorbecke G J (2000) *Cytokine Growth Factor Rev* 11, 89-96.
Tsukazaki T (1998) *Cell* 95:779-791.
Ulloa L (1999) *Nature* 397, 710-713.
Verschueren K (2000) *J Biol Chem* 275, 11320-11326.
Vorobjev P E (2001) *Antisense Nucleic Acid Drug Dev,* 11, 77-85.
Walton P S (1999) *Biotechnol Bioeng,* 65, 1-9.
Wang X 1995 *Brain Res Bull* 36, 607-9.
Weinberg A D (1992) *J Immunol* 148, 2109-2117.
Weiner H L (1994) *Annu. Rev. Immunol* 12, 809-837.
Wekerle H (1986) *Trends Neurosci* 9, 271-277.
Wiendl H (2000) *Nervenarzt* 71, 597-610.
Winer S (2001) *J Immunol* 166, 2831-2841.
Winer S (2001) *J Immunol* 166, 4751-4756.
Wodak S J (1987) *Ann NY Acad Sci.* 501, 1-13.
Wolinsky J S (2000) *Neurology,* 54, 1734-41.
Woodroofe M N (1993) *Cytokine* 5, 583-588.
Wyss-Coray T (1997). *J Neuroimmunol,* 77, 45-50.
Wyss-Coray T (1995) *Am J Pathol,* 147, 53-67.
Wyss-Coray T (2000). *Am J Pathol,* 156, 139-150.
Xu L Y (2000) *Clin Immunol* 95, 70-78.
Yamashita K 1999 *Brain Res* 836, 139-45.
Yang D (2002) *Proc Natl Acad Sci USA* 99, 9942-9947.
Zhang Y (1996) *Nature* 383:168-172.
Zhang Y (1997) *Curr Biol.* 7, 270-276.
Zhu H (1999) *J Biol Chem* 274, 32258-32264.
Zhu Y 2000 *Brain Res* 866, 286-98.
Zhu Y (2002) *J Neurosci* 22, 3898-3909.
Zamvil S S (1990) *Annu. Rev. Immunol* 8, 579-621.
Ziyadeh F N (2000) *Proc Natl Acad Sci USA* 97, 8015-8020.

The invention claimed is:

1. A method for ameliorating and/or treating multiple sclerosis in a subject comprising administering to said subject a therapeutically effective amount of an anti-Smad7 antisense oligonucleotide molecule comprising the nucleic acid molecule gtcgcccttctccccgcag (SEQ ID NO. 20).

2. The method of claim 1, wherein said subject is a mammal.

3. The method of claim 2, wherein said mammal is a human.

4. The method of claim 1, wherein said multiple sclerosis is selected from the group consisting of relapsing-remitting multiple sclerosis, secondary progressive multiple sclerosis, primary chronic progressive multiple sclerosis, neuromyelitis optica (Devic's syndrome), acute disseminated encephalomyelitis, fulminant multiple sclerosis (Marburg's variant), isolated autoimmune optic neuritis, isolated autoimmune transverse myelitis and flab's concentric sclerosis.

* * * * *

SEQUENCE LISTING

```
<160> NUMBER OF SEQ ID NOS: 91

<210> SEQ ID NO 1
<211> LENGTH: 3111
<212> TYPE: DNA
<213> ORGANISM: Homo sapiens

<400> SEQUENCE: 1
ggcacgagcg gagagccgcg cagggcgcgg gccgcgcggg gtggggcagc cggagcgcag      60
gcccccgatc cccggcgggc gccccgggc ccccgcgcgc gccccggcct ccgggagact      120
ggcgcatgcc acggagcgcc cctcgggccg ccgccgctcc tgcccgggcc cctgctgctg      180
ctgctgtcgc ctgcgcctgc tgccccaact cggcgcccga cttcttcatg gtgtgcggag      240
gtcatgttcg ctccttagca ggcaaacgac ttttctcctc gcctcctcgc cccgcatgtt      300
caggaccaaa cgatctgcgc tcgtccggcg tctctggagg agccgtgcgc ccggcggcga      360
ggacgaggag gagggcgcag ggggaggtgg aggaggaggc gagctgcggg gagaaggggc      420
gacggacagc cgagcgcatg gggccggtgg cggcggcccg ggcagggctg gatgctgcct      480
gggcaaggcg gtgcgaggtg ccaaaggtca ccaccatccc cacccgccag ccgcgggcgc      540
```

```
cggcgcggcc gggggcgccg aggcggatct gaaggcgctc acgcactcgg tgctcaagaa    600
actgaaggag cggcagctgg agctgctgct ccaggccgtg gagtcccgcg gcgggacgcg    660
caccgcgtgc ctcctgctgc ccggccgcct ggactgcagg ctgggcccgg ggcgccccgc    720
cggcgcgcag cctgcgcagc cgccctcgtc ctactcgctc ccctcctgc tgtgcaaagt     780 gttcaggtgg ccggatctca ggcattcctc ggaagtcaag aggctgtgtt gctgtgaatc    840
ttacgggaag atcaacccg agctggtgtg ctgcaacccc catcacctta gccgactctg     900
cgaactagag tctccccccc ctccttactc cagatacccg atggattttc tcaaaccaac    960
tgcagactgt ccagatgctg tgccttcctc cgctgaaaca gggggaacga attatctggc   1020
ccctgggggg ctttcagatt cccaacttct tctggagcct ggggatcggt cacactggtg   1080
cgtggtggca tactgggagg agaagacgag agtggggagg ctctactgtg tccaggagcc   1140
ctctctggat atcttctatg atctacctca ggggaatggc ttttgcctcg acagctcaa    1200 ttcggacaac aagagtcagc tggtgcagaa ggtgcggagc aaaatcggct gcggcatcca   1260
gctgacgcgg gaggtggatg tgtgtgtgggt gtacaaccgc agcagttacc ccatcttcat   1320
caagtccgcc acactggaca acccggactc caggacgctg ttggtacaca aggtgttccc   1380
cggtttctcc atcaaggctt tcgactacga aaggcgtac agcctgcagc ggcccaatga    1440
ccacgagttt atgcagcagc cgtggacggg ctttaccgtg cagatcagct tgtgaaggg    1500 ctggggtcag tgctacaccc gccagttcat cagcagctgc ccgtgctggc tagaggtcat   1560
cttcaacagc cggtagccgc gtgcggaggg acagagcgt gagctgagca ggccacactt    1620
caaactactt tgctgctaat attttcctcc tgagtgcttg cttttcatgc aaactctttg   1680
gtcgtttttt ttttgtttgt tggttggttt tcttcttctc gtcctcgttt tgttctgtt     1740 ttgtttcgct ctttgagaaa tagcttatga aaagaattgt tgggggtttt tttggaagaa    1800
ggggcaggta tgatcggcag gacaccctga taggaagagg ggaagcagaa atccaagcac    1860
caccaaacac agtgtatgaa gggggcggt catcatttca cttgtcagga gtgtgtgtga    1920
gtgtgagtgt gcggctgtgt gtgcacgcgt gtgcaggagc ggcagatggg gagacaacgt   1980
gctctttgtt ttgtgtctct tatggatgtc cccagcagag aggtttgcag tcccaagcgg   2040
tgtctctcct gccccttgga cacgctcagt ggggcagagg cagtacctgg gcaagctggc   2100
ggctggggtc ccagcagctg ccaggagcac ggctctgtcc ccagcctggg aaagcccctg    2160
cccctcctct ccctcatcaa ggacacgggc ctgtccacag gcttctgagc agcgagcctg    2220
ctagtggccg aaccagaacc aattattttc atccttgtct tattcccttc ctgccagccc    2280
ctgccattgt agcgtctttc tttttggcc atctgctcct ggatctccct gagatgggct     2340
tcccaagggc tgccggggca gcccccctcac agtattgctc acccagtgcc ctctcccctc    2400
agcctctccc ctgcctgccc tggtgacatc aggttttcc cggacttaga aaaccagctc     2460
agcactgcct gctcccatcc tgtgtgttaa gctctgctat taggccagca agcggggatg    2520
tccctgggag ggacatgctt agcagtcccc ttccctccaa gaaggatttg gtccgtcata    2580
acccaaggta ccatcctagg ctgacaccta actcttcttt catttcttct acaactcata    2640
cactcgtatg atacttcgac actgttctta gctcaatgag catgtttaga ctttaacata    2700 agctatttt ctaactacaa aggtttaaat gaacaagaga agcattctca ttggaaattt     2760
agcattgtag tgctttgaga gagaaaggac tcctgaaaaa aaacctgaga tttattaaag    2820
aaaaaaatgt attttatgtt atatataaat atattattac ttgtaaatat aaagacgttt    2880
tataagcatc attatttatg tattgtgcaa tgtgtataaa caagaaaaat aaagaaaaga    2940
```

-continued

```
tgcactttgc tttaatataa atgcaaataa caaatgccaa attaaaaaag ataaacacaa    3000
gattggtgtt ttttcctatg ggtgttatca cctagctgaa tgttttttcta aaggagttta   3060 tgttccatta aacgattttt aaaatgtaca cttgaaaaaa aaaaaaaaaa a             3111

<210> SEQ ID NO 2
<211> LENGTH: 426
<212> TYPE: PRT
<213> ORGANISM: Homo sapiens

<400> SEQUENCE: 2

Met Phe Arg Thr Lys Arg Ser Ala Leu Val Arg Arg Leu Trp Arg Ser
 1               5                  10                  15

Arg Ala Pro Gly Gly Glu Asp Glu Glu Gly Ala Gly Gly Gly
            20                  25                  30

Gly Gly Gly Glu Leu Arg Gly Glu Gly Ala Thr Asp Ser Arg Ala His
        35                  40                  45

Gly Ala Gly Gly Gly Pro Gly Arg Ala Gly Cys Cys Leu Gly Lys
    50                  55                  60

Ala Val Arg Gly Ala Lys Gly His His Pro His Pro Ala Ala
65                  70                  75                  80

Gly Ala Gly Ala Ala Gly Gly Ala Glu Ala Asp Leu Lys Ala Leu Thr
                85                  90                  95

His Ser Val Leu Lys Lys Leu Lys Glu Arg Gln Leu Glu Leu Leu Leu
            100                 105                 110

Gln Ala Val Glu Ser Arg Gly Gly Thr Arg Thr Ala Cys Leu Leu Leu
        115                 120                 125

Pro Gly Arg Leu Asp Cys Arg Leu Gly Pro Gly Ala Pro Ala Gly Ala
    130                 135                 140

Gln Pro Ala Gln Pro Ser Ser Tyr Ser Leu Pro Leu Leu Leu Cys
145                 150                 155                 160

Lys Val Phe Arg Trp Pro Asp Leu Arg His Ser Ser Glu Val Lys Arg
                165                 170                 175

Leu Cys Cys Cys Glu Ser Tyr Gly Lys Ile Asn Pro Glu Leu Val Cys
            180                 185                 190

Cys Asn Pro His His Leu Ser Arg Leu Cys Glu Leu Glu Ser Pro Pro
        195                 200                 205

Pro Pro Tyr Ser Arg Tyr Pro Met Asp Phe Leu Lys Pro Thr Ala Asp
    210                 215                 220

Cys Pro Asp Ala Val Pro Ser Ser Ala Glu Thr Gly Gly Thr Asn Tyr
225                 230                 235                 240

Leu Ala Pro Gly Gly Leu Ser Asp Ser Gln Leu Leu Leu Glu Pro Gly
                245                 250                 255

Asp Arg Ser His Trp Cys Val Val Ala Tyr Trp Glu Glu Lys Thr Arg
            260                 265                 270

Val Gly Arg Leu Tyr Cys Val Gln Glu Pro Ser Leu Asp Ile Phe Tyr
        275                 280                 285

Asp Leu Pro Gln Gly Asn Gly Phe Cys Leu Gly Gln Leu Asn Ser Asp
    290                 295                 300

Asn Lys Ser Gln Leu Val Gln Lys Val Arg Ser Lys Ile Gly Cys Gly
305                 310                 315                 320

Ile Gln Leu Thr Arg Glu Val Asp Gly Val Trp Val Tyr Asn Arg Ser
                325                 330                 335

Ser Tyr Pro Ile Phe Ile Lys Ser Ala Thr Leu Asp Asn Pro Asp Ser
```

-continued

```
                 340                 345                 350
Arg Thr Leu Leu Val His Lys Val Phe Pro Gly Phe Ser Ile Lys Ala
            355                 360                 365
Phe Asp Tyr Glu Lys Ala Tyr Ser Leu Gln Arg Pro Asn Asp His Glu
    370                 375                 380
Phe Met Gln Gln Pro Trp Thr Gly Phe Thr Val Gln Ile Ser Phe Val
385                 390                 395                 400
Lys Gly Trp Gly Gln Cys Tyr Thr Arg Gln Phe Ile Ser Ser Cys Pro
                405                 410                 415
Cys Trp Leu Glu Val Ile Phe Asn Ser Arg
            420                 425

<210> SEQ ID NO 3
<211> LENGTH: 3681
<212> TYPE: DNA
<213> ORGANISM: Mus musculus

<400> SEQUENCE: 3
cgagtgcggc gcggcgagcc cccagcggcg gcagaaggac tcgagcgcca ggagagggcg    60
gacggggggac gaggaggctc cggggcgcga cgaagagagt ctccgaggaa gaggctgcga   120
gaggacaccc gggcctcctg ccgccactgt cgggtcgggg ccagcagctc atgagagcag   180
cccccggcggc caccccgcggc caggagaagg agcaccggag gccccacac tagcctgtgc    240
cctcggggggc gagagcttgc gacccgccgg agcccgccgc cgcgccgccc tccccgcgc    300
tgacagcccc ccggggcgca gccgccgccg cagcatcttc tgtccctgct tccccagcgc   360
ggaggaagtc cccgccgagg acctgagccc ccgggaacgc aggaggaaag accagagact   420
ctaaaacacc cagatacgca agattgaagc agcctagcca gacctttctg tggattaaaa   480
gaaatacgat tttttttttt tttttttggc agaagaaaag gaaaggaaga ccggctgggt   540
tcagcaagga aaaaagggg gatgtaactc gtggatacgt tttttttccc ccacccttcc    600
aacatcttgt tttatttgt aaacattttc tcttttaaac ccgggctcca tccggtgccc    660
tccagacctc cgaggtgcga ggaggtggtg tgttttttca ttgggggctt tgcatatttt   720
ggttttgggg gttttgagag accctccaga catctcacga ggggtgaagt ctactcggtc    780
ccctcccgca agtcttcgcg tgcacagaat tcgaggagat ccggttacta aggatataga   840
agaaaaaaaa taaatcgtgc ctgccttttt tttttaattg cctgcttctc cccaccccca   900
aattaagttg cttagcaagg gggaaagagg ctttttcctc cctttagtag ctcagcctaa   960
cgtctttcgt tttttttttt ttttttttt ttttgccccc gaggatcttc catgtaggaa  1020
gccgaggctg gcgagcccga cactcgggag ccactgtagg ggggccttt ttggggggagg   1080
cgtctaccgg ggttgcctcg gccgccccca gggaagcggc ggccgcgttc ctccagggca  1140
cgccggggcc cgaaagccgc gcagggcgcg ggccgcgccg ggtggggcag ccgaagcgca  1200
gcccccgat ccccggcagg cgccccgggg cccccgcgcg cgccccggcc tctgggagac   1260
tggcgcatgc cacggagcgc ccctcgggcc gccgccgctt ctgccgggc ccctgctgtt   1320
gctgctgtcg cctgcgcctg ctgccccaac tcggcgcccg acttcttcat ggtgtgcgga  1380
ggtcatgttc gctccttagc cggcaaacga ctttttctcct cgcctcctcg ccccgcatgt  1440
tcaggaccaa acgatctgcg ctcgtccggc gtctctggag gagccgtgcg cccggcggcg  1500
aggacgagga gggaggcgtg gggggtggc gcggaggagg cgagctgcgg ggagaagggg   1560
cgacggacgg ccgggcttat ggggctggtg gcggcggtgc gggcagggct ggctgctgcc   1620
```

-continued

```
tgggcaaggc agtccgaggt gccaaaggtc accaccatcc ccatccccca acctcgggtg      1680
ccggggcggc cggggcgcc gaggcggatc tgaaggcgct cacgcactcg gtgctcaaga       1740
aactcaagga gcggcagctg gagctgctgc ttcaggccgt ggagtcccgc ggcggtacgc      1800
gcaccgcgtg cctcctgctg cccggccgcc tggactgcag gctgggcccg ggggcgcccg      1860
ccagcgcgca gcccgcgcag ccgccctcgt cctactcgct cccctcctg ctgtgcaaag       1920 tgttcaggtg gccggatctc aggcattcct cggaagtcaa gaggctgtgt tgctgtgaat     1980
cttacgggaa gatcaacccc gagctggtgt gctgcaaccc ccatcacctt agtcgactct      2040
gtgaactaga gtctccccct cctccttact ccagatacc aatggatttt ctcaaaccaa      2100
ctgcaggctg tccagatgct gtaccttcct ccgcggaaac cggggaacg aattatctgg       2160 cccctggggg gctttcagat tcccaacttc ttctggagcc tggggatcgg tcacactggt     2220
gcgtggtggc atactgggag gagaagactc gcgtggggag gctctactgt gtccaagagc     2280
cctccctgga tatcttctat gatctacctc aggggaatgg cttttgcctc ggacagctca     2340
attcggacaa caagagtcag ctggtacaga aagtgcggag caagatcggc tgtggcatcc     2400
agctgacgcg ggaagtggat ggcgtgtggg tttacaaccg cagcagttac cccatcttca     2460
tcaagtccgc cacactggac aacccggact ccaggacgct gttggtgcac aaagtgttcc     2520
ctggtttctc catcaaggct tttgactatg agaaagccta cagcctgcag cggcccaatg     2580
accacgagtt catgcagcaa ccatggacgg gtttcaccgt gcagatcagc tttgtgaagg     2640
gctgggccca gtgctacacc cgccagttca tcagcagctg cccgtgctgg ctggaggtca     2700
tcttcaacag ccggtagtcg gtcgtgtggt ggggagaaga ggacagggcg gatcgtgagc     2760
cgagcaggcc accgttcaaa ctacttgctg ctaatctttc ccgagtgatt gcttttcatg     2820
caaactcttt ggttggtgtt gttattgcca ttcattgttg gttttgtttt gttctgttct     2880
ggtttgtttt ttttttttttt cctccccaag ggctgccggg acagcccag tcacagtatt      2940 gctaccccag taccctctca ggcccttcca ccgggtccca gccgtggtgg ttttttcatc     3000
aggtttctcc cagatgtgga aagtcagctc agcatcccat cccccatcct gtgtgctgag     3060
ctctgtagac cagcgagggg catcagggag ggacctgcgc agtgccccccc cttcctgctg     3120 agaagggtgt agccccgtca caacaaaggt accatccctt ggctggctcc agcccttct      3180 ctcagctcat acgctcgctc gtatgatact ttgacactgt tcttagctca atgagcatgt     3240
ttagaattta acataagcta ttttttctaac tacaaaggtt taaatgaaca agagaagcat     3300
tctcattgga aatttagcat tgtagtgctt tgagagagga aaggactcct taaaagaaaa     3360
aaaaagctga gatttattaa agaaaaatgt attttatgtt atatataaat atattattac     3420
ttgtaaatat aaagacgttt tataagcatc attatttatg tattgtgcaa tgtgtataaa     3480
cgagaagaat aaagaaaaga tgcactttgc tttaatataa atgtaaataa catgccaaat     3540
taaaaaaaaa aagataaaca caagattggt gttttttct atgggtgtta tcacctagct      3600
gaatgttttt ctaaaggagt ttatgttcca ttaaacaatt tttaaaatgt taaaaaaaaa     3660
aaaaaaaaaa aaaaaaaaaa a                                                3681
```

<210> SEQ ID NO 4
<211> LENGTH: 426
<212> TYPE: PRT
<213> ORGANISM: Mus musculus

<400> SEQUENCE: 4

Met Phe Arg Thr Lys Arg Ser Ala Leu Val Arg Arg Leu Trp Arg Ser

-continued

```
  1               5                10               15
Arg Ala Pro Gly Gly Glu Asp Glu Glu Gly Val Gly Gly Gly
              20               25               30

Gly Gly Gly Glu Leu Arg Gly Glu Gly Ala Thr Asp Gly Arg Ala Tyr
              35               40               45

Gly Ala Gly Gly Gly Ala Gly Arg Ala Gly Cys Cys Leu Gly Lys
              50               55               60

Ala Val Arg Gly Ala Lys Gly His His His Pro His Pro Pro Thr Ser
 65               70               75               80

Gly Ala Gly Ala Ala Gly Gly Ala Glu Ala Asp Leu Lys Ala Leu Thr
              85               90               95

His Ser Val Leu Lys Lys Leu Lys Glu Arg Gln Leu Glu Leu Leu
              100              105              110

Gln Ala Val Glu Ser Arg Gly Gly Thr Arg Thr Ala Cys Leu Leu Leu
              115              120              125

Pro Gly Arg Leu Asp Cys Arg Leu Gly Pro Gly Ala Pro Ala Ser Ala
              130              135              140

Gln Pro Ala Gln Pro Pro Ser Ser Tyr Ser Leu Pro Leu Leu Leu Cys
145              150              155              160

Lys Val Phe Arg Trp Pro Asp Leu Arg His Ser Ser Glu Val Lys Arg
              165              170              175

Leu Cys Cys Cys Glu Ser Tyr Gly Lys Ile Asn Pro Glu Leu Val Cys
              180              185              190

Cys Asn Pro His His Leu Ser Arg Leu Cys Glu Leu Glu Ser Pro Pro
              195              200              205

Pro Pro Tyr Ser Arg Tyr Pro Met Asp Phe Leu Lys Pro Thr Ala Gly
              210              215              220

Cys Pro Asp Ala Val Pro Ser Ser Ala Glu Thr Gly Gly Thr Asn Tyr
225              230              235              240

Leu Ala Pro Gly Gly Leu Ser Asp Ser Gln Leu Leu Leu Glu Pro Gly
              245              250              255

Asp Arg Ser His Trp Cys Val Val Ala Tyr Trp Glu Glu Lys Thr Arg
              260              265              270

Val Gly Arg Leu Tyr Cys Val Gln Glu Pro Ser Leu Asp Ile Phe Tyr
              275              280              285

Asp Leu Pro Gln Gly Asn Gly Phe Cys Leu Gly Gln Leu Asn Ser Asp
              290              295              300

Asn Lys Ser Gln Leu Val Gln Lys Val Arg Ser Lys Ile Gly Cys Gly
305              310              315              320

Ile Gln Leu Thr Arg Glu Val Asp Gly Val Trp Val Tyr Asn Arg Ser
              325              330              335

Ser Tyr Pro Ile Phe Ile Lys Ser Ala Thr Leu Asp Asn Pro Asp Ser
              340              345              350

Arg Thr Leu Leu Val His Lys Val Phe Pro Gly Phe Ser Ile Lys Ala
              355              360              365

Phe Asp Tyr Glu Lys Ala Tyr Ser Leu Gln Arg Pro Asn Asp His Glu
              370              375              380

Phe Met Gln Gln Pro Trp Thr Gly Phe Thr Val Gln Ile Ser Phe Val
385              390              395              400

Lys Gly Trp Gly Gln Cys Tyr Thr Arg Gln Phe Ile Ser Ser Cys Pro
              405              410              415

Cys Trp Leu Glu Val Ile Phe Asn Ser Arg
              420              425
```

<210> SEQ ID NO 5
<211> LENGTH: 4311
<212> TYPE: DNA
<213> ORGANISM: Rattus norvegicus

<400> SEQUENCE: 5

| | | | | | |
|---|---|---|---|---|---|
| tgagtgcggc | gcggcgagcc | cccagcggcg | gcagaaggac | tcgagcgcca | ggagagggcg | 60 |
| gacgggggac | gaggaggctc | ccgggcgcga | cgaagagagt | ctcggaggaa | gaggctgcga | 120 |
| gaggacaccc | gggcctcctg | ccgccactgt | cgggtcgggg | ccagcagctt | atgcgagcag | 180 |
| ccccagcgac | caccctcggc | caggagaagg | ggcaccggca | gccccacgc | tagctagcct | 240 |
| gccgcctgtg | ccctcggggg | cgagagcttg | cgacccgccg | gagcccgccg | ccgcgccgcc | 300 |
| ctcccccgcg | ctgacagccc | ccggggcgc | agccgccgcc | gcagcatctt | ctgtccctgc | 360 |
| ttccccagcg | cggaggaagt | ccccgccgag | gacctgggcc | ccggggagcg | caggaggaaa | 420 |
| gaccagagac | tctaaaacac | ccagatacgc | aagattgaag | cagcctaacc | agacctttct | 480 |
| gtggattaaa | agaaatacga | tttttttttt | gacagaagaa | aaggaaagga | agaccggcgg | 540 |
| ggttcagcaa | ggaaaaaaag | gggatgtaac | tcgtggatac | ggttttttccc | cccacccttc | 600 |
| caacatcttg | ttctactttg | taaacatttt | ctcttttttaa | accccggctc | catccggtgc | 660 |
| cctccagacc | tccgaggtgc | gagaaggtgg | tgtgtttttt | cactgggggc | tttgcatatt | 720 |
| tggttttggg | gttttgaga | gaccctccag | acatctcacg | agggtgaag | tctactcggc | 780 |
| cccctcccctc | aagtcttcgc | gtgcacagaa | ttcgaggaga | tccggttact | aaggatatag | 840 |
| aagaaaaaaa | taaatcgtgt | gcctgccttt | ttttttttta | attgcctgct | tctcccacc | 900 |
| cccaaattaa | gttgcttagc | aagggggaaa | gaggcttttt | cctcccttca | gtagctcagc | 960 |
| ctaacgtctt | tcgttttttg | ccctgagga | tcttccatgt | aggaagccga | ggctggcgag | 1020 |
| cccgacactc | gggagccact | gtaggggggc | ctttttgggg | agaggcgtcg | accgggggctg | 1080 |
| cctcggccgc | ccccagggaa | gcggcggccg | cgttcctcag | gggcacgccg | gggcccgaga | 1140 |
| gccgcgcagg | gcgcgggccg | cgccgggtgg | ggcagccgaa | gcgcaggccc | ccgatccccg | 1200 |
| gcgggcgccc | ctgggccccc | gcgcgcgccc | cggcctccgg | gagactggcg | catgccacgg | 1260 |
| agcgcccctc | gggccgccgc | cgcttctgcc | cgggcccctg | ctgttgttgc | tgtcgcctgc | 1320 |
| gcctgctgcc | ccaactcggc | gcccgacttc | ttcatggtgt | gcggaggtca | tgttcgctcc | 1380 |
| ttagccggca | aacgactttt | ctcctcgcct | cctcgcccg | catgttcagg | accaaacgat | 1440 |
| ctgcgctcgt | ccggcgtctc | tggaggagcc | gtgcgcccgg | cggcgaggac | gaggaggagg | 1500 |
| gcgtgggggg | tggcggcggc | ggaggcgacc | tgcggggaga | agggcgacg | gacgccgggg | 1560 |
| cttatggggc | tggtggcggc | ggtgcgggca | gggctggctg | ctgcctgggt | aaggcagtcc | 1620 |
| gaggtgccaa | aggtcaccac | catccccatc | ccccatcctc | gggtgccggg | gcggccgggg | 1680 |
| gcgccgaggc | ggatctgaag | gcgctcacgc | actcggtgct | caagaaactc | aaggagcggc | 1740 |
| agctggagct | gctgcttcag | gccgtggagt | cccgcggcgg | tacgcgcacc | gcgtgcctcc | 1800 |
| tgctgcccgg | ccgcctggac | tgcaggctgg | gcccggggc | gcccgccagc | gcgcagcccg | 1860 |
| cgcagccgcc | ctcgtcctac | tcgctccccc | tcctgctgtg | caaagtgttc | aggtggccgg | 1920 |
| atctcaggca | ttcctcggaa | gtcaagaggc | tgtgttgctg | tgaatcttac | gggaagatca | 1980 |
| accccgagct | ggtgtgctgc | aaccccccatc | accttagtcg | actctgtgaa | ctagagtctc | 2040 |
| cccctcctcc | ttactccaga | tacccgatgg | attttctcaa | accaactgca | gactgtccag | 2100 |

-continued

| | |
|---|---|
| acgctgtacc ttcctccgat gaaaccgggg gaacgaatta tctggcccct gggggctttt | 2160 |
| cagattccca acttcttctg gagcctgggg atcggtcaca ctggtgcgtg gtggcatact | 2220 |
| gggaggagaa gactcgagtg gggaggctct actgtgtcca agagccctcc ctggatatct | 2280 |
| tctatgatct acctcagggg aatggctttt gcctcggaca gctcaattcg gacaacaaga | 2340 |
| gtcagctggt acagaaagtg aggagcaaga tcggctgtgg catccagctg acaagggaag | 2400 |
| tggatggcgt gtgggtttac aaccgcagca gttaccccat cttcatcaag tccgccacac | 2460 |
| tggacaaccc ggactccagg acgctgttgg tgcacaaagt gttccctggt ttctccatca | 2520 |
| aggcttttga ctatgaaaag gcctacagcc tgcagcggcc caatgaccac gagttcatgc | 2580 |
| agcagccatg gacgggcttc accgtgcaga ttagcttcgt gaagggctgg ggccagtgct | 2640 |
| acacccgcca gttcatcagc agttgcccgt gctggctgga ggtcatcttc aacagccggt | 2700 |
| agtctcccgg tgtggggaga agaggacagg acggaggggt gagccgagca ggccaccgtt | 2760 |
| caaactactt gctgctaatc tttcatgcaa aactctttcg gtcggttttg ttgtttgcca | 2820 |
| ttcattgttg gttctgtttt gttttgtttt cctttttttt ttttcttcct tcttcttttt | 2880 |
| cctcctttct tgtcactctt gtgtcctgtg tgtctcgttc tttgagaaaa tatgatgcgg | 2940 |
| attttttggtt gtgtgttttt tttttcgtt tgtttgtttg ttgttgttgt ttgtgttttg | 3000 |
| aggtggtggt gggtgcggtt ggcaggacac cccgatacaa aaacgggaag caagagtcag | 3060 |
| cactgccaag cgtggtgtgc gaaagtgggt accaccttcc cctttggatc agcatttcag | 3120 |
| ttgtcagtgt gtgtgtgtga gggggtgta cgtgaatgac agatggggga atggcgtgct | 3180 |
| ttttttgtgt tctttatgga tgtccccagc tgagaggctt gcagttccaa gctgtgtgtc | 3240 |
| tctcactgtg tgtctctctc atgagccttt cggacatgct cggtggggca gaggctgtac | 3300 |
| ctgggcagac tggcagcagg tgtcccagca ggtgccgagc tctgctccgc tgaagctccc | 3360 |
| ccgcccccgc ccccttcccc acaggacacg ggcctatcca caggcttctg agaagccagc | 3420 |
| ctgctagaag gctgaaccag aaccaattgt tttcatccct gtcttactgc ctcctgtcac | 3480 |
| ccgctgccat tgtcgaaggc tgtcttttttt ggccatctgc tcctggatct ctcttgagat | 3540 |
| gggcttccca agggctgccg ggacagcccc agtcacagta ttgctacccc agtaccttct | 3600 |
| caggcccttc caccggtccc agccgtggtt ttttcatcag gtttctccca gatctggaaa | 3660 |
| gtcagctcag cacccccatcc cccagcctgt gtgctgagct ctgtagacca gcgaggggca | 3720 |
| tcagggaggg acctgctcag tgcccaccca ccccccttc ccgctgagaa gggtgtagcc | 3780 |
| ccgtcataac aaaggtacca tcgtaggctg gctcccagcc cttctctcgg ctcatacact | 3840 |
| cgtatgatac tctgacactg ttcttggctc aatgagcatg ctcacacttt aatataagct | 3900 |
| attttctaa ctacaaaggt ttaaatgaac aagagaggcg ttctcatcgg aaatttagca | 3960 |
| tcgtagtgct ttgagagagg aaaggactcc ttaaaagaga aaaaaaaag ctgagattta | 4020 |
| ttaaagaaaa aaatgtattt tatgttatat ataaatatat tattacttgt aaatataaag | 4080 |
| acgttttata agcatcatta tttatgtatt gtgcaatgtg tataaacgag aataaagaaa | 4140 |
| agatgcactt tgctttaata taaacgcaaa taacatgcca aattaaaaaa aaaaaagata | 4200 |
| aacacaagat tggtgttttt ttctatgggt gttatcacct agctgaatgt ttttctaaag | 4260 |
| gagtttatgt tccattaaac aatttttaaa atgtataaaa aaaaaaaaaa a | 4311 |

<210> SEQ ID NO 6
<211> LENGTH: 426
<212> TYPE: PRT
<213> ORGANISM: Rattus norvegicus

```
<400> SEQUENCE: 6

Met Phe Arg Thr Lys Arg Ser Ala Leu Val Arg Arg Leu Trp Arg Ser
  1               5                  10                  15

Arg Ala Pro Gly Gly Glu Asp Glu Glu Glu Gly Val Gly Gly Gly Gly
             20                  25                  30

Gly Gly Gly Asp Leu Arg Gly Glu Gly Ala Thr Asp Gly Arg Ala Tyr
         35                  40                  45

Gly Ala Gly Gly Gly Gly Ala Gly Arg Ala Gly Cys Cys Leu Gly Lys
     50                  55                  60

Ala Val Arg Gly Ala Lys Gly His His His Pro His Pro Pro Ser Ser
 65                  70                  75                  80

Gly Ala Gly Ala Ala Gly Gly Ala Glu Ala Asp Leu Lys Ala Leu Thr
             85                  90                  95

His Ser Val Leu Lys Lys Leu Lys Glu Arg Gln Leu Glu Leu Leu Leu
            100                 105                 110

Gln Ala Val Glu Ser Arg Gly Gly Thr Arg Thr Ala Cys Leu Leu Leu
            115                 120                 125

Pro Gly Arg Leu Asp Cys Arg Leu Gly Pro Gly Ala Pro Ala Ser Ala
            130                 135                 140

Gln Pro Ala Gln Pro Pro Ser Ser Tyr Ser Leu Pro Leu Leu Leu Cys
145                 150                 155                 160

Lys Val Phe Arg Trp Pro Asp Leu Arg His Ser Ser Glu Val Lys Arg
                165                 170                 175

Leu Cys Cys Cys Glu Ser Tyr Gly Lys Ile Asn Pro Glu Leu Val Cys
            180                 185                 190

Cys Asn Pro His His Leu Ser Arg Leu Cys Glu Leu Glu Ser Pro Pro
            195                 200                 205

Pro Pro Tyr Ser Arg Tyr Pro Met Asp Phe Leu Lys Pro Thr Ala Asp
            210                 215                 220

Cys Pro Asp Ala Val Pro Ser Ser Asp Glu Thr Gly Gly Thr Asn Tyr
225                 230                 235                 240

Leu Ala Pro Gly Gly Leu Ser Asp Ser Gln Leu Leu Leu Glu Pro Gly
                245                 250                 255

Asp Arg Ser His Trp Cys Val Val Ala Tyr Trp Glu Glu Lys Thr Arg
            260                 265                 270

Val Gly Arg Leu Tyr Cys Val Gln Glu Pro Ser Leu Asp Ile Phe Tyr
            275                 280                 285

Asp Leu Pro Gln Gly Asn Gly Phe Cys Leu Gly Gln Leu Asn Ser Asp
            290                 295                 300

Asn Lys Ser Gln Leu Val Gln Lys Val Arg Ser Lys Ile Gly Cys Gly
305                 310                 315                 320

Ile Gln Leu Thr Arg Glu Val Asp Gly Val Trp Val Tyr Asn Arg Ser
                325                 330                 335

Ser Tyr Pro Ile Phe Ile Lys Ser Ala Thr Leu Asp Asn Pro Asp Ser
            340                 345                 350

Arg Thr Leu Leu Val His Lys Val Phe Pro Gly Phe Ser Ile Lys Ala
            355                 360                 365

Phe Asp Tyr Glu Lys Ala Tyr Ser Leu Gln Arg Pro Asn Asp His Glu
            370                 375                 380

Phe Met Gln Gln Pro Trp Thr Gly Phe Thr Val Gln Ile Ser Phe Val
385                 390                 395                 400

Lys Gly Trp Gly Gln Cys Tyr Thr Arg Gln Phe Ile Ser Ser Cys Pro
```

```
                  405                 410                 415
     Cys Trp Leu Glu Val Ile Phe Asn Ser Arg
                 420                 425

<210> SEQ ID NO 7
<211> LENGTH: 18
<212> TYPE: DNA
<213> ORGANISM: Mus musculus

<400> SEQUENCE: 7
cttcggctgc cccacccg                                                   18

<210> SEQ ID NO 8
<211> LENGTH: 19
<212> TYPE: DNA
<213> ORGANISM: Mus musculus

<400> SEQUENCE: 8
atcgtttggt cctgaacat                                                  19

<210> SEQ ID NO 9
<211> LENGTH: 18
<212> TYPE: DNA
<213> ORGANISM: Mus musculus

<400> SEQUENCE: 9
ccctcctcct cgtcctcg                                                   18

<210> SEQ ID NO 10
<211> LENGTH: 20
<212> TYPE: DNA
<213> ORGANISM: Mus musculus

<400> SEQUENCE: 10
gtcgcccctt ctccccgcag                                                 20

<210> SEQ ID NO 11
<211> LENGTH: 18
<212> TYPE: DNA
<213> ORGANISM: Mus musculus

<400> SEQUENCE: 11
gccgtccgtc gcccctcc                                                   18

<210> SEQ ID NO 12
<211> LENGTH: 18
<212> TYPE: DNA
<213> ORGANISM: Mus musculus

<400> SEQUENCE: 12
agcaccgagt gcgtgagc                                                   18

<210> SEQ ID NO 13
<211> LENGTH: 18
<212> TYPE: DNA
<213> ORGANISM: Mus musculus

<400> SEQUENCE: 13
agttcacaga gtcgacta                                                   18

<210> SEQ ID NO 14
<211> LENGTH: 18
<212> TYPE: DNA
```

```
<213> ORGANISM: Mus musculus

<400> SEQUENCE: 14
ggcaaaagcc attcccct                                                 18

<210> SEQ ID NO 15
<211> LENGTH: 18
<212> TYPE: DNA
<213> ORGANISM: Mus musculus

<400> SEQUENCE: 15
gccgatcttg ctccgcac                                                 18

<210> SEQ ID NO 16
<211> LENGTH: 18
<212> TYPE: DNA
<213> ORGANISM: Homo sapiens

<400> SEQUENCE: 16
ctccggctgc cccacccc                                                 18

<210> SEQ ID NO 17
<211> LENGTH: 18
<212> TYPE: DNA
<213> ORGANISM: Homo sapiens

<400> SEQUENCE: 17
cgaacatgac ctccgcac                                                 18

<210> SEQ ID NO 18
<211> LENGTH: 19
<212> TYPE: DNA
<213> ORGANISM: Homo sapiens

<400> SEQUENCE: 18
atcgtttggt cctgaacat                                                19

<210> SEQ ID NO 19
<211> LENGTH: 18
<212> TYPE: DNA
<213> ORGANISM: Homo sapiens

<400> SEQUENCE: 19
ccctcctcct cgtcctcg                                                 18

<210> SEQ ID NO 20
<211> LENGTH: 20
<212> TYPE: DNA
<213> ORGANISM: Homo sapiens

<400> SEQUENCE: 20
gtcgccccct tctcccgcag                                               20

<210> SEQ ID NO 21
<211> LENGTH: 18
<212> TYPE: DNA
<213> ORGANISM: Homo sapiens

<400> SEQUENCE: 21
gctgtccgtc gccccttc                                                 18

<210> SEQ ID NO 22
<211> LENGTH: 18
```

```
<212> TYPE: DNA
<213> ORGANISM: Homo sapiens

<400> SEQUENCE: 22
agcaccgagt gcgtgagc                                                 18

<210> SEQ ID NO 23
<211> LENGTH: 18
<212> TYPE: DNA
<213> ORGANISM: Homo sapiens

<400> SEQUENCE: 23
agttcgcaga gtcggcta                                                 18

<210> SEQ ID NO 24
<211> LENGTH: 18
<212> TYPE: DNA
<213> ORGANISM: Homo sapiens

<400> SEQUENCE: 24
ggcaaaagcc attcccct                                                 18

<210> SEQ ID NO 25
<211> LENGTH: 18
<212> TYPE: DNA
<213> ORGANISM: Homo sapiens

<400> SEQUENCE: 25
gccgattttg ctccgcac                                                 18

<210> SEQ ID NO 26
<211> LENGTH: 18
<212> TYPE: DNA
<213> ORGANISM: Homo sapiens

<400> SEQUENCE: 26
ctgccccttc ttccaaaa                                                 18

<210> SEQ ID NO 27
<211> LENGTH: 18
<212> TYPE: DNA
<213> ORGANISM: Homo sapiens

<400> SEQUENCE: 27
actcacacac actcctga                                                 18

<210> SEQ ID NO 28
<211> LENGTH: 18
<212> TYPE: DNA
<213> ORGANISM: Homo sapiens

<400> SEQUENCE: 28
tgcccaggta ctgcctct                                                 18

<210> SEQ ID NO 29
<211> LENGTH: 18
<212> TYPE: DNA
<213> ORGANISM: Homo sapiens

<400> SEQUENCE: 29
gagatccagg agcagatg                                                 18

<210> SEQ ID NO 30
```

-continued

```
<211> LENGTH: 18
<212> TYPE: DNA
<213> ORGANISM: Rattus norvegicus

<400> SEQUENCE: 30
cttcggctgc cccacccg                                                 18

<210> SEQ ID NO 31
<211> LENGTH: 19
<212> TYPE: DNA
<213> ORGANISM: Rattus norvegicus

<400> SEQUENCE: 31
atcgtttggt cctgaacat                                                19

<210> SEQ ID NO 32
<211> LENGTH: 18
<212> TYPE: DNA
<213> ORGANISM: Rattus norvegicus

<400> SEQUENCE: 32
ccctcctcct cgtcctcg                                                 18

<210> SEQ ID NO 33
<211> LENGTH: 20
<212> TYPE: DNA
<213> ORGANISM: Rattus norvegicus

<400> SEQUENCE: 33
gtcgcccctt ctccccgcag                                               20

<210> SEQ ID NO 34
<211> LENGTH: 18
<212> TYPE: DNA
<213> ORGANISM: Rattus norvegicus

<400> SEQUENCE: 34
gccgtccgtc gcccttc                                                  18

<210> SEQ ID NO 35
<211> LENGTH: 18
<212> TYPE: DNA
<213> ORGANISM: Rattus norvegicus

<400> SEQUENCE: 35
agcaccgagt gcgtgagc                                                 18

<210> SEQ ID NO 36
<211> LENGTH: 18
<212> TYPE: DNA
<213> ORGANISM: Rattus norvegicus

<400> SEQUENCE: 36
agttcacaga gtcgacta                                                 18

<210> SEQ ID NO 37
<211> LENGTH: 18
<212> TYPE: DNA
<213> ORGANISM: Rattus norvegicus

<400> SEQUENCE: 37
ggcaaaagcc attccct                                                  18
```

```
<210> SEQ ID NO 38
<211> LENGTH: 18
<212> TYPE: DNA
<213> ORGANISM: Rattus norvegicus

<400> SEQUENCE: 38
gccgatcttg ctcctcac                                                       18

<210> SEQ ID NO 39
<211> LENGTH: 21
<212> TYPE: DNA
<213> ORGANISM: Homo sapiens

<400> SEQUENCE: 39
gtcgcccctt ctcccccgca g                                                   21

<210> SEQ ID NO 40
<211> LENGTH: 12
<212> TYPE: PRT
<213> ORGANISM: Mus musculus

<400> SEQUENCE: 40

His Ser Leu Gly Lys Trp Leu His Pro Asp Lys Phe
 1               5                  10

<210> SEQ ID NO 41
<211> LENGTH: 20
<212> TYPE: DNA
<213> ORGANISM: Mus musculus

<400> SEQUENCE: 41
gtcgcaccgt ctcacagcag                                                     20

<210> SEQ ID NO 42
<211> LENGTH: 15
<212> TYPE: DNA
<213> ORGANISM: Mus musculus

<400> SEQUENCE: 42
atggacaata tgtct                                                          15

<210> SEQ ID NO 43
<211> LENGTH: 20
<212> TYPE: DNA
<213> ORGANISM: Rattus norvegicus

<400> SEQUENCE: 43
ctgcggggag aagggcgac                                                      20

<210> SEQ ID NO 44
<211> LENGTH: 21
<212> TYPE: RNA
<213> ORGANISM: Homo sapiens

<400> SEQUENCE: 44
guucaggacc aaacgaucug c                                                   21

<210> SEQ ID NO 45
<211> LENGTH: 23
<212> TYPE: RNA
<213> ORGANISM: Homo sapiens

<400> SEQUENCE: 45
gcagaucguu uggccugaa cau                                                  23
```

```
<210> SEQ ID NO 46
<211> LENGTH: 21
<212> TYPE: RNA
<213> ORGANISM: Homo sapiens

<400> SEQUENCE: 46
cucacgcacu cggugcucaa g                                              21

<210> SEQ ID NO 47
<211> LENGTH: 23
<212> TYPE: RNA
<213> ORGANISM: Homo sapiens

<400> SEQUENCE: 47
cuugagcacc gagugcguga gcg                                            23

<210> SEQ ID NO 48
<211> LENGTH: 21
<212> TYPE: RNA
<213> ORGANISM: Homo sapiens

<400> SEQUENCE: 48
cucggcgccc gacuucuucu u                                              21

<210> SEQ ID NO 49
<211> LENGTH: 21
<212> TYPE: RNA
<213> ORGANISM: Homo sapiens

<400> SEQUENCE: 49
gaagaagucg ggcgccgagu u                                              21

<210> SEQ ID NO 50
<211> LENGTH: 21
<212> TYPE: RNA
<213> ORGANISM: Homo sapiens

<400> SEQUENCE: 50
acgacuuuuc uccucgccuu u                                              21

<210> SEQ ID NO 51
<211> LENGTH: 21
<212> TYPE: RNA
<213> ORGANISM: Homo sapiens

<400> SEQUENCE: 51
aggcgaggag aaaagucguu u                                              21

<210> SEQ ID NO 52
<211> LENGTH: 21
<212> TYPE: RNA
<213> ORGANISM: Homo sapiens

<400> SEQUENCE: 52
acgaucugcg cucguccggu u                                              21

<210> SEQ ID NO 53
<211> LENGTH: 21
<212> TYPE: RNA
<213> ORGANISM: Homo sapiens

<400> SEQUENCE: 53
```

-continued ccggacgagc gcagaucguu u                                              21

<210> SEQ ID NO 54
<211> LENGTH: 21
<212> TYPE: RNA
<213> ORGANISM: Homo sapiens

<400> SEQUENCE: 54
ggcgcucacg cacucggugu u                                              21

<210> SEQ ID NO 55
<211> LENGTH: 21
<212> TYPE: RNA
<213> ORGANISM: Homo sapiens

<400> SEQUENCE: 55
caccgagugc gugagcgccu u                                              21

<210> SEQ ID NO 56
<211> LENGTH: 21
<212> TYPE: RNA
<213> ORGANISM: Homo sapiens

<400> SEQUENCE: 56
ggagcggcag cuggagcugu u                                              21

<210> SEQ ID NO 57
<211> LENGTH: 21
<212> TYPE: RNA
<213> ORGANISM: Homo sapiens

<400> SEQUENCE: 57
cagcuccagc ugccgcuccu u                                              21

<210> SEQ ID NO 58
<211> LENGTH: 21
<212> TYPE: RNA
<213> ORGANISM: Homo sapiens

<400> SEQUENCE: 58
aguguucagg uggccggauu u                                              21

<210> SEQ ID NO 59
<211> LENGTH: 21
<212> TYPE: RNA
<213> ORGANISM: Homo sapiens

<400> SEQUENCE: 59
auccggccac cugaacacuu u                                              21

<210> SEQ ID NO 60
<211> LENGTH: 21
<212> TYPE: RNA
<213> ORGANISM: Homo sapiens

<400> SEQUENCE: 60
gucaagaggc uguguugcuu u                                              21

<210> SEQ ID NO 61
<211> LENGTH: 21
<212> TYPE: RNA
<213> ORGANISM: Homo sapiens

<400> SEQUENCE: 61
agcaacacag ccucuugacu u                                                 21

<210> SEQ ID NO 62
<211> LENGTH: 21
<212> TYPE: RNA
<213> ORGANISM: Homo sapiens

<400> SEQUENCE: 62
gaggcugugu ugcugugaau u                                                 21

<210> SEQ ID NO 63
<211> LENGTH: 21
<212> TYPE: RNA
<213> ORGANISM: Homo sapiens

<400> SEQUENCE: 63
uucacagaca cacagccucu u                                                 21

<210> SEQ ID NO 64
<211> LENGTH: 21
<212> TYPE: RNA
<213> ORGANISM: Homo sapiens

<400> SEQUENCE: 64
ucuuacggga agaucaaccu u                                                 21

<210> SEQ ID NO 65
<211> LENGTH: 21
<212> TYPE: RNA
<213> ORGANISM: Homo sapiens

<400> SEQUENCE: 65
gguugaucuu cccguaagau u                                                 21

<210> SEQ ID NO 66
<211> LENGTH: 21
<212> TYPE: RNA
<213> ORGANISM: Homo sapiens

<400> SEQUENCE: 66
gaucaacccc gagcuggugu u                                                 21

<210> SEQ ID NO 67
<211> LENGTH: 21
<212> TYPE: RNA
<213> ORGANISM: Homo sapiens

<400> SEQUENCE: 67
caccagcucg ggguugaucu u                                                 21

<210> SEQ ID NO 68
<211> LENGTH: 21
<212> TYPE: RNA
<213> ORGANISM: Homo sapiens

<400> SEQUENCE: 68
ccccgagcug gugugcugcu u                                                 21

<210> SEQ ID NO 69
<211> LENGTH: 21
<212> TYPE: RNA
<213> ORGANISM: Homo sapiens

```
<400> SEQUENCE: 69
gcagcacacc agcucggggu u                                              21

<210> SEQ ID NO 70
<211> LENGTH: 21
<212> TYPE: RNA
<213> ORGANISM: Homo sapiens

<400> SEQUENCE: 70
cgaauuaucu ggccccuggu u                                              21

<210> SEQ ID NO 71
<211> LENGTH: 21
<212> TYPE: RNA
<213> ORGANISM: Homo sapiens

<400> SEQUENCE: 71
ccaggggcca gauaauucgu u                                              21

<210> SEQ ID NO 72
<211> LENGTH: 21
<212> TYPE: RNA
<213> ORGANISM: Homo sapiens

<400> SEQUENCE: 72
cuucuucugg agccuggggu u                                              21

<210> SEQ ID NO 73
<211> LENGTH: 21
<212> TYPE: RNA
<213> ORGANISM: Homo sapiens

<400> SEQUENCE: 73
ccccaggcuc cagaagaagu u                                              21

<210> SEQ ID NO 74
<211> LENGTH: 21
<212> TYPE: RNA
<213> ORGANISM: Homo sapiens

<400> SEQUENCE: 74
uggcuuuugc cucggacagu u                                              21

<210> SEQ ID NO 75
<211> LENGTH: 21
<212> TYPE: RNA
<213> ORGANISM: Homo sapiens

<400> SEQUENCE: 75
cuguccgagg caaaagccau u                                              21

<210> SEQ ID NO 76
<211> LENGTH: 21
<212> TYPE: RNA
<213> ORGANISM: Homo sapiens

<400> SEQUENCE: 76
uucggacaac aagagucagu u                                              21

<210> SEQ ID NO 77
<211> LENGTH: 21
<212> TYPE: RNA
<213> ORGANISM: Homo sapiens
```

-continued

```
<400> SEQUENCE: 77
cugacucuug uuguccgaau u                                              21

<210> SEQ ID NO 78
<211> LENGTH: 21
<212> TYPE: RNA
<213> ORGANISM: Homo sapiens

<400> SEQUENCE: 78
ccgcagcagu uaccccaucu u                                              21

<210> SEQ ID NO 79
<211> LENGTH: 21
<212> TYPE: RNA
<213> ORGANISM: Homo sapiens

<400> SEQUENCE: 79 gauggguaa cugcugcggu u                                               21

<210> SEQ ID NO 80
<211> LENGTH: 21
<212> TYPE: RNA
<213> ORGANISM: Homo sapiens

<400> SEQUENCE: 80
guccgccaca cuggacaacu u                                              21

<210> SEQ ID NO 81
<211> LENGTH: 21
<212> TYPE: RNA
<213> ORGANISM: Homo sapiens

<400> SEQUENCE: 81
guuguccagu guggcggacu u                                              21

<210> SEQ ID NO 82
<211> LENGTH: 21
<212> TYPE: RNA
<213> ORGANISM: Homo sapiens

<400> SEQUENCE: 82
cccggacucc aggacgcugu u                                              21

<210> SEQ ID NO 83
<211> LENGTH: 21
<212> TYPE: RNA
<213> ORGANISM: Homo sapiens

<400> SEQUENCE: 83
cagcguccug gaguccgggu u                                              21

<210> SEQ ID NO 84
<211> LENGTH: 131
<212> TYPE: PRT
<213> ORGANISM: Rattus norvegicus

<400> SEQUENCE: 84

Gly Gln Phe Arg Val Ile Gly Pro Gly His Pro Ile Arg Ala Leu Val
 1               5                  10                  15

Gly Asp Glu Ala Glu Leu Pro Cys Arg Ile Ser Pro Gly Lys Asn Ala
            20                  25                  30
```

```
Thr Gly Met Glu Val Gly Trp Tyr Arg Ser Pro Phe Ser Arg Val Val
         35                  40                  45

His Leu Tyr Arg Asn Gly Lys Asp Gln Asp Ala Glu Gln Ala Pro Glu
 50                  55                  60

Tyr Arg Gly Arg Thr Glu Leu Leu Lys Glu Ser Ile Gly Glu Gly Lys
 65                  70                  75                  80

Val Ala Leu Arg Ile Gln Asn Val Arg Phe Ser Asp Glu Gly Gly Tyr
                 85                  90                  95

Thr Cys Phe Phe Arg Asp His Ser Tyr Gln Glu Glu Ala Ala Val Glu
                100                 105                 110

Leu Lys Val Glu Asp Pro Phe Tyr Trp Ile Asn Pro Gly His His His
            115                 120                 125

His His His
    130

<210> SEQ ID NO 85
<211> LENGTH: 24
<212> TYPE: DNA
<213> ORGANISM: Artificial Sequence
<220> FEATURE:
<223> OTHER INFORMATION: Primer

<400> SEQUENCE: 85
atgttcagga ccaaacgatc tgcg                                          24

<210> SEQ ID NO 86
<211> LENGTH: 23
<212> TYPE: DNA
<213> ORGANISM: Artificial Sequence
<220> FEATURE:
<223> OTHER INFORMATION: Primer

<400> SEQUENCE: 86
agctgccgct ccttcagttt ctt                                           23

<210> SEQ ID NO 87
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 87
atggacaata tgtcta                                                   16

<210> SEQ ID NO 88
<211> LENGTH: 1282
<212> TYPE: DNA
<213> ORGANISM: Homo Sapiens

<400> SEQUENCE: 88
atgttcagga ccaaacgatc tgcgctcgtc cggcgtctct ggaggagccg tgcgcccggc    60
ggcgaggacg aggaggaggg cgcagggggda ggtggaggag gaggcgagct gcggggagaa   120
ggggcgacgg acagccgagc gcatggggcc ggtggcggcg gcccgggcag ggctggatgc   180
tgcctgggca aggcggtgcg aggtgccaaa ggtcaccacc atccccaccc gccagccgcg   240
ggcgccggcg cggccggggg cgccgaggcg gatctgaagg cgctcacgca tcggtgctc    300 aagaaactga aggagcggca gctggagctg ctgctccagg ccgtggagtc ccgcggcggg   360
acgcgcaccg cgtgcctcct gctgcccggc cgcctggact gcaggctggg cccgggggcg   420
```

```
cccgccggcg cgcagcctgc gcagccgccc tcgtcctact cgctcccct cctgctgtgc      480 aaagtgttca ggtggccgga tctcaggcat tcctcggaag tcaagaggct gtgttgctgt      540
gaatcttacg ggaagatcaa ccccgagctg gtgtgctgca accccatca ccttagccga      600 ctctgcgaac tagagtctcc ccccctcct tactccagat acccgatgga ttttctcaaa      660
ccaactgcag actgtccaga tgctgtgcct tcctccgctg aaacaggggg aacgaattat      720
ctggcccctg gggggctttc aggattccca acttcttctg gagcctgggg atcggtcaca      780
ctggtgcgtg gtggcatact gggaggagaa gacgagagtg gggaggctct actgtgtcca      840
ggagccctct ctggatatct tctatgatct acctcagggg aatggctttt gcctcggaca      900
gctcaattcg gacaacaaga gtcagctggt gcagaaggtg cggagcaaaa tcggctgcgg      960
catccagctg acgcgggagg tggatggtgt gtgggtgtac aaccgcagca gttaccccat     1020
cttcatcaag tccgccacac tggacaaccc ggactccagg acgctgttgg tacacaaggt     1080
gttccccggt ttctccatca aggctttcga ctacgagaag gcgtacagcc tgcagcggcc     1140
caatgaccac gagtttatgc agcagccgtg gacgggcttt accgtgcaga tcagcttgtgt     1200 gaagggctgg ggccagtgct acacccgcca gttcatcagc agctgcccgt gctggctaga     1260
ggtcatcttc aacagccggt ag                                               1282

<210> SEQ ID NO 89
<211> LENGTH: 3087
<212> TYPE: DNA
<213> ORGANISM: Homo Sapiens

<400> SEQUENCE: 89
cggagagccg cgcagggcgc gggccgcgcg gggtggggca gccggagcgc aggcccccga       60
tccccggcgg gcgcccccgg gccccgcgc gcgcccccggc ctccgggaga ctggcgcatg      120
ccacggagcg cccctcgggc cgccgccgct cctgccgggg ccctgctgc tgctgctgtc      180 gcctgcgcct gctgccccaa ctcggcgccc gacttcttca tggtgtgcgg aggtcatgtt      240
cgctccttag caggcaaacg acttttctcc tcgcctcctc gccccgcatg ttcaggacca      300
aacgatctgc gctcgtccgg cgtctctgga ggagccgtgc gcccggcggc gaggacgagg      360
aggagggcgc agggggaggt ggaggaggag gcgagctgcg gggagaaggg gcgacggaca      420
gccgagcgca tggggccggt ggcggcggcc cgggcagggc tggatgctgc ctgggcaagg      480
cggtgcgagg tgccaaaggt caccaccatc cccacccgcc agccgcgggc gccggcgcgg      540 ccggggggcgc cgaggcggat ctgaaggcgc tcacgcactc ggtgctcaag aaactgaagg      600
agcggcagct ggagctgctg ctccaggccg tggagtcccg cggcgggacg cgcaccgcgt      660
gcctcctgct gcccggccgc ctggactgca ggctgggccc gggggcgccc gccggcgcgc      720
agcctgcgca gccgccctcg tcctactcgc tccccctcct gctgtgcaaa gtgttcaggt      780
ggccggatct caggcattcc tcggaagtca agaggctgtg ttgctgtgaa tcttacggga      840
agatcaaccc cgagctggtg tgctgcaacc ccatcaccct tagccgactc tgcgaactag      900
agtctccccc ccctccttac tccagatacc cgatggattt tctcaaacca actgcagact      960
gtccagatgc tgtgccttcc tccgctgaaa caggggaac gaattatctg gcccctgggg     1020
ggctttcagg attcccaact tcttctggag cctggggatc ggtcacactg gtgcgtggtg     1080
gcatactggg aggagaagac gagagtgggg aggctctact gtgtccagga gccctctctg     1140
gatatcttct atgatctacc tcaggggaat ggcttttgcc tcggacagct caattcggac     1200
aacaagagtc agctggtgca gaaggtgcgg agcaaaatcg gctgcggcat ccagctgacg     1260
```

```
cgggaggtgg atggtgtgtg ggtgtacaac cgcagcagtt accccatctt catcaagtcc    1320
gccacactgg acaacccgga ctccaggacg ctgttggtac acaaggtgtt ccccggtttc    1380
tccatcaagg ctttcgacta cgagaaggcg tacagcctgc agcggcccaa tgaccacgag    1440
tttatgcagc agccgtggac gggctttacc gtgcagatca gctttgtgaa gggctggggc    1500
cagtgctaca cccgccagtt catcagcagc tgcccgtgct ggctagaggt catcttcaac    1560
agccggtagc cgcgtgcgga ggggacagag cgtgagctga gcaggccaca cttcaaacta    1620
ctttgctgct aatattttcc tcctgagtgc ttgcttttca tgcaaactct ttggtcgttt    1680 ttttttttgtt tgttggttgg ttttcttctt ctcgtcctcg tttgtgttct gttttgtttc    1740
gctctttgag aaatagctta tgaaaagaat tgttgggggt ttttttggaa gaaggggcag    1800
gtatgatcgg caggacaccc tgataggaag aggggaagca gaaatccaag caccaccaaa    1860
cacagtgtat gaagggggc ggtcatcatt tcacttgtca ggagtgtgtg tgagtgtgag    1920
tgtgcggctg tgtgtgcacg cgtgtgcagg agcggcagat ggggagacaa cgtgctcttt    1980
gttttgtgtc tcttatggat gtccccagca gagaggtttg cagtcccaag cggtgtctct    2040 cctgccccttg gacacgctc agtggggcag aggcagtacc tgggcaagct ggcggctggg    2100
gtcccagcag ctgccaggag cacggctctg tccccagcct gggaaagccc ctgccctcc    2160 tctccctcat caaggacacg ggcctgtcca caggcttctg agcagcgagc ctgctagtgg    2220
ccgaaccaga accaattatt ttcatccttg tcttattccc ttcctgccag ccctgccat     2280 tgtagcgtct ttcttttttg gccatctgct cctggatctc cctgagatgg gcttcccaag    2340
ggctgccggg gcagcccct cacagtattg ctcacccagt gccctctccc ctcagcctct    2400
cccctgcctg ccctggtgac atcaggtttt tcccggactt agaaaaccag ctcagcactg    2460
cctgctccca gcctgtgtgt taagctctgc tattaggcca gcaagcgggg atgtccctgg    2520
gagggacatg cttagcagtc cccttccctc caagaaggat ttggtccgtc ataacccaag    2580
gtaccatcct aggctgacac ctaactcttc tttcatttct tctacaactc atacactcgt    2640
atgatacttc gacactgttc ttagctcaat gagcatgttt agactttaac ataagctatt    2700
tttctaacta caaaggttta aatgaacaag agaagcattc tcattggaaa tttagcattg    2760
tagtgctttg agagagaaag gactcctgaa aaaaaacctg agatttatta aagaaaaaaa    2820
tgtattttat gttatatata aatatattat tacttgtaaa tataaagacg ttttataagc    2880
atcattattt atgtattgtg caatgtgtat aaacaagaaa aataaagaaa agatgcactt    2940
tgctttaata taaatgcaaa taacaaatgc caaattaaaa aagataaaca caagattggt    3000 gttttttttct atgggtgtta tcacctagct gaatgttttt ctaaaggagt ttatgttcca    3060
ttaaacgatt tttaaaatgt acacttg                                       3087
```

<210> SEQ ID NO 90
<211> LENGTH: 1281
<212> TYPE: DNA
<213> ORGANISM: Homo Sapiens

<400> SEQUENCE: 90

```
atgttcagga ccaaacgatc tgcgctcgtc cggcgtctct ggaggagccg tgcgcccggc      60
ggcgaggacg aggaggaggg cgcaggggga ggtgaggag gaggcgagct gcggggagaa     120
ggggcgacgg acagccgagc gcatgggcc ggtggcggcg gcccgggcag ggctggatgc     180
tgcctgggca aggcggtgcg aggtgccaaa tgtcaccacc atccccaccc gccagccgcg    240
```

| | |
|---|---|
| ggcgccggcg cggccggggg cgccgaggcg gatctgaagg cgctcacgca ctcggtgctc | 300 |
| aagaaactga aggagcggca gctggagctg ctgctccagg ccgtggagtc ccgcggcggg | 360 |
| acgcgcaccg cgtgcctcct gctgcccggc cgcctggact gcaggctggg cccgggggcg | 420 |
| cccgccggcg cgcagcctgc gcagccgccc tcgtcctact cgctcccccct cctgctgtgc | 480 |
| aaagtgttca ggtggccgga tctcaggcat tcctcggaag tcaagaggct gtgttgctgt | 540 |
| gaatcttacg ggaagatcaa ccccgagctg gtgtgctgca accccatca ccttagccga | 600 |
| ctctgcgaac tagagtctcc cccccctcct tactccagat acccgatgga ttttctcaaa | 660 |
| ccaactgcag actgtccaga tgctgtgcct tcctccgctg aaacaggggg aacgaattat | 720 |
| ctggcccctg gggggctttc agattcccaa cttcttctgg agcctgggga tcggtcacac | 780 |
| tggtgcgtgg tggcatactg ggaggagaag acgagagtgg ggaggctcta ctgtgtccag | 840 |
| gagccctctc tggatatctt ctatgatcta cctcagggga atggcttttg cctcggacag | 900 |
| ctcaattcgg acaacaagag tcagctggtg cagaaggtgc ggagcaaaat cggctgcggc | 960 |
| atccagctga cgcgggaggt ggatggtgtg tgggtgtaca accgcagcag ttaccccatc | 1020 |
| ttcatcaagt ccgccacact ggacaacccg gactccagga cgctgttggt acacaaggtg | 1080 |
| ttccccggtt tctccatcaa ggctttcgac tacgagaagg cgtacagcct gcagcggccc | 1140 |
| aatgaccacg agtttatgca gcagccgtgg acgggcttta ccgtgcagat cagctttgtg | 1200 |
| aagggctggg gccagtgcta cacccgccag ttcatcagca gctgcccgtg ctggctagag | 1260 |
| gtcatcttca acagccggta g | 1281 |

<210> SEQ ID NO 91
<211> LENGTH: 3111
<212> TYPE: DNA
<213> ORGANISM: Homo Sapiens

<400> SEQUENCE: 91

| | |
|---|---|
| ggcacgagcg gagagccgcg cagggcgcgg gccgcgcggg gtggggcagc cggagcgcag | 60 |
| gcccccgatc cccggcgggc gccccggggc cccgcgcgc gccccggcct ccgggagact | 120 |
| ggcgcatgcc acggagcgcc cctcgggccg ccgccgctcc tgcccgggcc cctgctgctg | 180 |
| ctgctgtcgc ctgcgcctgc tgccccaact cggcgcccga cttcttcatg gtgtgcggag | 240 |
| gtcatgttcg ctccttagca ggcaaacgac ttttctcctc gcctcctcgc cccgcatgtt | 300 |
| caggaccaaa cgatctgcgc tcgtccggcg tctctggagg agccgtgcgc ccggcggcga | 360 |
| ggacgaggag gagggcgcag ggggaggtgg aggaggaggc gagctgcggg gagaaggggc | 420 |
| gacggacagc cgagcgcatg gggccggtgg cggcggcccg ggcagggctg gatgctgcct | 480 |
| gggcaaggcg gtgcgaggtg ccaaaggtca ccaccatccc caccgccag ccgcgggcgc | 540 |
| cggcgcggcc gggggcgccg aggcggatct gaaggcgctc acgcactcgg tgctcaagaa | 600 |
| actgaaggag cggcagctgg agctgctgct ccaggccgtg gagtcccgcg cgggacgcg | 660 |
| caccgcgtgc ctcctgctgc ccggccgcct ggactgcagg ctgggccgg ggcgcccgc | 720 |
| cggcgcgcag cctgcgcagc cgccctcgtc ctactcgctc cccctcctgc tgtgcaaagt | 780 |
| gttcaggtgg ccggatctca ggcattcctc ggaagtcaag aggctgtgtt gctgtgaatc | 840 |
| ttacgggaag atcaacccccg agctggtgtg ctgcaaccc catcacctta gccgactctg | 900 |
| cgaactagag tctccccccc ctccttactc cagatacccg atggattttc tcaaaccaac | 960 |
| tgcagactgt ccagatgctg tgccttcctc cgctgaaaca gggggaacga attatctggc | 1020 |
| ccctgggggg ctttcagatt cccaacttct tctggagcct ggggatcggt cacactggtg | 1080 |

-continued

```
cgtggtggca tactgggagg agaagacgag agtggggagg ctctactgtg tccaggagcc    1140
ctctctggat atcttctatg atctacctca ggggaatggc ttttgcctcg acagctcaa    1200 ttcggacaac aagagtcagc tggtgcagaa ggtgcggagc aaaatcggct gcggcatcca    1260
gctgacgcgg gaggtggatg gtgtgtgggt gtacaaccgc agcagttacc ccatcttcat    1320
caagtccgcc acactggaca acccggactc caggacgctg ttggtacaca aggtgttccc    1380
cggtttctcc atcaaggctt tcgactacga aaggcgtac agcctgcagc ggcccaatga    1440
ccacgagttt atgcagcagc cgtggacggg ctttaccgtg cagatcagct tgtgaaggg    1500 ctggggtcag tgctacaccc gccagttcat cagcagctgc ccgtgctggc tagaggtcat    1560
cttcaacagc cggtagccgc gtgcggaggg acagagcgt gagctgagca ggccacactt    1620
caaactactt tgctgctaat attttcctcc tgagtgcttg cttttcatgc aaactctttg    1680 gtcgttttt tttgtttgt tggttggttt tcttcttctc gtcctcgttt gtgttctgtt    1740
ttgtttcgct ctttgagaaa tagcttatga aaagaattgt tgggggtttt tttggaagaa    1800
ggggcaggta tgatcggcag dacaccctga taggaagagg ggaagcagaa atccaagcac    1860
caccaaacac agtgtatgaa gggggcggt catcatttca cttgtcagga gtgtgtgtga    1920
gtgtgagtgt gcggctgtgt gtgcacgcgt gtgcaggagc ggcagatggg gagacaacgt    1980
gctctttgtt ttgtgtctct tatggatgtc cccagcagag aggtttgcag tcccaagcgg    2040
tgtctctcct gccccttgga cacgctcagt ggggcagagg cagtacctgg gcaagctggc    2100
ggctggggtc ccagcagctg ccaggagcac ggctctgtcc ccagcctggg aaagcccctg    2160
cccctcctct ccctcatcaa ggacacgggc ctgtccacag gcttctgagc agcgagcctg    2220
ctagtggccg aaccagaacc aattattttc atccttgtct tattcccttc ctgccagccc    2280
ctgccattgt agcgtctttc ttttttggcc atctgctcct ggatctccct gagatgggct    2340
tcccaagggc tgccggggca gcccctcac agtattgctc acccagtgcc ctctcccctc    2400
agcctctccc ctgcctgccc tggtgacatc aggttttcc cggacttaga aaaccagctc    2460
agcactgcct gctcccatcc tgtgtgttaa gctctgctat taggccagca agcggggatg    2520
tccctgggag ggacatgctt agcagtcccc ttccctccaa gaaggatttg gtccgtcata    2580
acccaaggta ccatcctagg ctgacaccta actcttcttt catttcttct acaactcata    2640
cactcgtatg atacttcgac actgttctta gctcaatgag catgtttaga ctttaacata    2700
agctattttt ctaactacaa aggtttaaat gaacaagaga agcattctca ttggaaattt    2760
agcattgtag tgctttgaga gagaaaggac tcctgaaaaa aaacctgaga tttattaaag    2820
aaaaaaatgt attttatgtt atatataaat atattattac ttgtaaatat aaagacgttt    2880
tataagcatc attatttatg tattgtgcaa tgtgtataaa caagaaaaat aaagaaaaga    2940
tgcactttgc tttaatataa atgcaaataa caaatgccaa attaaaaaag ataaacacaa    3000
gattggtgtt ttttcctatg ggtgttatca cctagctgaa tgttttcta aaggagttta    3060 tgttccatta aacgattttt aaaatgtaca cttgaaaaaa aaaaaaaaaa a            3111
```